US007465794B2

(12) United States Patent
Collins et al.

(10) Patent No.: US 7,465,794 B2
(45) Date of Patent: *Dec. 16, 2008

(54) POLYNUCLEOTIDES ENCODING RECOMBINANT RESPIRATORY SYNCYTIAL VIRUSES EXPRESSING IMMUNE MODULATORY MOLECULES

(75) Inventors: Peter L. Collins, Kensington, MD (US);
Alexander Bukreyev, Olney, MD (US);
Brian R. Murphy, Bethesda, MD (US);
Stephen S. Whitehead, Montgomery Village, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/754,895

(22) Filed: Jan. 8, 2004

(65) Prior Publication Data
US 2005/0147622 A1 Jul. 7, 2005

Related U.S. Application Data

(60) Division of application No. 09/614,285, filed on Jul. 12, 2000, now Pat. No. 6,699,476, and a continuation-in-part of application No. 09/291,894, filed on Apr. 13, 1999, now Pat. No. 6,689,367, which is a continuation-in-part of application No. 08/892,403, filed on Jul. 15, 1997, now Pat. No. 5,993,824.

(60) Provisional application No. 60/143,425, filed on Jul. 13, 1999, provisional application No. 60/047,634, filed on May 23, 1997, provisional application No. 60/046,141, filed on May 9, 1997, provisional application No. 60/021,773, filed on Jul. 15, 1996.

(51) Int. Cl.
*C07H 21/04* (2006.01)
*C12P 21/00* (2006.01)
*A61K 39/12* (2006.01)
*A61K 39/155* (2006.01)

(52) U.S. Cl. .............. 536/23.72; 435/69.1; 435/320.1; 424/199.1; 424/211.1

(58) Field of Classification Search ............... 536/23.1, 536/23.72; 424/211.1
See application file for complete search history.

(56) References Cited

U.S. PATENT DOCUMENTS

| 5,716,821 A | 2/1998 | Wertz et al. ............... 435/235.1 |
| 5,789,229 A | 8/1998 | Wertz et al. ............... 435/235.1 |
| 5,869,036 A | 2/1999 | Belshe et al. ............... 424/93.2 |
| 5,882,651 A | 3/1999 | Murphy et al. ............ 424/211.1 |
| 5,922,326 A | 7/1999 | Murphy et al. ............ 424/211.1 |
| 5,993,824 A | 11/1999 | Murphy et al. ............ 424/211.1 |
| 6,033,886 A | 3/2000 | Conzelmann ............ 435/172.3 |

FOREIGN PATENT DOCUMENTS

| EP | 0 440 219 A1 | 8/1991 |
| EP | 0 702 085 A1 | 3/1996 |
| WO | WO 93/14207 | 7/1993 |
| WO | WO 93/21310 | 10/1993 |
| WO | WO 97/06270 | 2/1997 |
| WO | WO 97/11093 | 3/1997 |
| WO | WO 97/12032 | 4/1997 |
| WO | WO 97/20468 | 6/1997 |
| WO | WO 98/02530 | 1/1998 |
| WO | WO 98/43668 | 10/1998 |
| WO | WO 98/53078 | 11/1998 |
| WO | WO 99/02657 | 1/1999 |
| WO | WO 99/15631 | 4/1999 |
| WO | WO 00/61611 | 10/2000 |
| WO | WO 00/61737 | 10/2000 |
| WO | WO 01/04271 | 1/2001 |
| WO | WO 01/04321 | 1/2001 |

OTHER PUBLICATIONS

Bukreyev et al. (Journal of Virology, 2005, 79(15):9515-9526).*
Bukreyev et al. (Journal of Virology, 2001, 75(24):12128-121240).*
Bukreyev et al. (PNAS USA, 2002, 99(26):16987-16991).*
Bailly et al., "A Recombinant Human Parainfluenza Virus Type 3 (PIV3) in Which the Nucleocapsid N Protein Has Been Replaced by That of Bovine PIV3 Is Attenuated in Primates," *J. Virol.* 74(7):3188-3195, 2000.
Baron et al., "Rescue of Rinderpest Virus from Cloned cDNA," *J. Virol.* 71:1265-1271, 1997.
Bembridge et al., "Recombinant Vaccinia Virus Coexpressing the F Protein of Respiratory Syncytial Virus (RSV) and Interleukin-4 (IL-4) Does Not Inhibit the Development of RSV-Specific Memory Cytotoxic T Lymphocytes, whereas Priming is Diminished in the Presence of High Levels of IL-2 or Gamma Interferon," *J. Virol.* 72:4080-4087, 1998.

(Continued)

*Primary Examiner*—Stacy B Chen
(74) *Attorney, Agent, or Firm*—Birch, Stewart, Kolasch & Birch, LLP

(57) ABSTRACT

Recombinant respiratory syncytial virus (RSV) are provided which express one or more immune modulatory molecules. The recombinant virus is modified by addition or substitution of a polynucleotide sequence encoding the immune modulatory molecule, which is preferably a cytokine. Introduction of the cytokine increase, decrease, or otherwise enhances aspects of viral biology and/or host immune responses to RSV to facilitate vaccine use of the virus. Cytokines for use within the invention include but are not limited to interleukin 2 (IL-2), interleukin 4 (IL-4), interleukin 5 (IL-5), interleukin 6 (IL6), or interleukin 18 (IL-18), tumor necrosis factor (TNF) alpha, interferon gamma (IFN), and granulocyte-macrophage colony stimulating factor (GM-CSF). The polynucleotide or immune modulatory molecule is preferably added or substituted into the recombinant viral genome or antigenome, typically at an intergenic or other non-coding site, as a separate gene but may be otherwise expressed, for example as a fusion protein.

63 Claims, 6 Drawing Sheets

OTHER PUBLICATIONS

Bermingham et al.; "The M2-2 Protein of Human Respiratory Syncytial Virus is a Regulatory Factor Involved in the Balance Between RNA Replication and Transcription," *Proc. Natl. Acad. Sci. USA* 96:11259-11264. 1999.

Buchholz et al., "Generation of Bovine Respiratory Syncytial Virus (BRSV) from Cdna: BRSV NS2 Is Not Essential for Virus Replication in Tissue Culture, and the Human RSV Leader Region Acts as a Functional BRSV Genome Promoter," *J. Virol.* 73:251-259, 1999.

Buchholz et al., "Chimeric Bovine Respiratory Syncytial Virus with Glycoprotein Gene Substitutions from human Respiratory Syncytial Virus (HRSV): Effects on Host Range and Evaluation as a Live-Attenuated HRSV Vaccine," *J. Virol.* 74:1187-1199, 2000.

Bukreyev, et al., "Recovery of Infectious Respiratory Syncytial Virus Expressing an Additional, Foreign Gene," *J. Virol.* 70:6634-41, 1996.

Bukreyev, et al., "Recombinant Respiratory Syncytial virus from which the Entire SH Gene has been Deleted Grows Efficiently in Cell Culture and Exhibits Site-Specific Attenuation in the Respiratory Tract of the Mouse," *J. Virol.* 71:8973-8982, 1997.

Bukreyev, et al., "Interferon γ Expressed by a Recombinant Respiratory Syncytial Virus Attenuates Virus Replication in Mice Without Compromising Immunogenicity," *Proc. Nat. Acad. Sci. USA* 96:2367-2372, 1999.

Collins et al., "Rescue of Synthetic Analogs of Respiratory Syncytial Virus Genomic RNA and Effect of Truncations and Mutations on the Expression of a Foreign Reporter Gene," *Proc. Natl. Acad. Sci. USA*, 88:9663-9667, 1991.

Collins, et al., "Rescue of a 7502-Nucleotide (49.3% of Full-Length) Synthetic Analog of Respiratory Syncytial Virus Genomic RNA," *Virology* 195:252-256, 1993.

Collins et al., "Production of Infectious Human Respiratory Syncytial Virus from Cloned cDNA Confirms an Essential Role of the Transcription Elongation Factor from the 5' Proximal Open Reading Frame of the M2 mRNA in Gene Expression and Provides a Capability for Vaccine Development," *Proc Nat. Acad. Sci. USA* 92:11563-11567, 1995.

Collins et al., "Support Plasmids and Support Proteins Required for Recovery of Recombinant Respiratory Syncytial Virus," *Virology* 259:251-255, 1999.

Conzelmann et al., "Rescue of Synthetic Genomic RNA Analogs of Rabies Virus by Plasmid-Encoded Proteins," *J. Virol.* 68:713-719, 1994.

Conzelmann, "Genetic Manipulation of Non-Segmented Negative-strand RNA Viruses," *J. Gen. Virol.* 77:381-389, 1996.

Crowe, et al., "A Further Attenuated Derivative of a Cold-Passaged Temperature-Sensitive Mutant of Human Respiratory Syncytial Virus Retains Immunogenicity and Protective Efficacy Against Wild-Type Challenge in Seronegative Chimpanzees," *Vaccine* 12:783-790, 1994.

Crowe, et al., "Acquisition of the *ts* Phenotype by a Chemically Mutagenized Cold-Passaged Human Respiratory Syncytial Virus Vaccine Candidate Results from the Acquisition of a Single Mutation in the Polymerase (L) Gene," *Virus Genes* 13:269-273, 1996.

Delenda, et al., "Normal Cellular Replication of Sendai Virus Without the *trans*-Frame, Nonstructural V Protein," *Virology* 228:55-62, 1997.

Durbin et al., "Recovery of Infectious Human Parainfluenza Virus Type 3 from cDNA," *Virology* 235:323-332, 1997.

Finke and Conzelmann, "Ambisense Gene Expression from Recombinant Rabies Virus: Random Packaging or Positive- and Negative-Strand Ribonucleoprotein Complexes into Rabies Virions," *J. Virol.* 71:7281-7288, 1997.

Flexner et al., "Prevention of Vaccinia Virus Infection in Immunodeficient Mice by Vector-Directed IL-2 Expression," *Nature* 330:259-262,1987.

Flexner et al., "Attenuation and Immunogenicity in Primates of Vaccinia Virus Recombinants Expressing Human Interleukin-2," *Vaccine* 8:17-21, 1990.

Garcia-Sastre et al., "Use of a Mammalian Internal Ribosomal Entry Site Element for Expression of a Foreign Protein by a Transfectant Influenza Virus," *J. Virol.* 68:6254-6261, 1994.

Garcin et al., "A Highly Recombinogenic System for the Recovery of Infectious Sendai Paramyxovirus from cDNA: Generation of Novel Copy-back Nondefective Interfering Virus," *EMBO J.* 14:6087-6094, 1995.

Giavedoni et al., "Expression of Gamma Interferon by Simian Immunodeficiency Virus Increases Attenuation and Reduces Postchallenge Virus Load in Vaccinated Rhesus Macaques," *J. Virol.* 71:866-872, 1997.

Grundlach et al., "Construction, Replication, and Immunogenic Properties of a Simian Immunodeficiency Virus Expressing Interleukin-2," *J. Virol.* 71:2225-2232, 1997.

He et al., "Recovery of Infectious SV5 from Cloned DNA and Expression of a Foreign Gene," *Virology* 237:249-260, 1997.

He et al., "The Paramyxovirus SV5 Small Hydrophobic (SH) Protein is not Essential for Virus Growth in Tissue Culture Cells," *Virology* 250:30-40, 1998.

Hendricks et al., "Further Characteristics of the Soluble Form of the G Glycoprotein of Respiratory Syncytial Virus," *J. Virol.* 62:2228-2233, 1988.

Hoffman et al., "An Infectious Clone of Human Parainfluenza Virus Type 3," *J. Virol.* 71:4272-4277, 1997.

Horvath et al., "Eukaryotic Coupled Translation of Tandem Cistrons: Identification of the Influenza B Virus BM2 Polypeptide," *EMBO J.* 9:2639-2647, 1990.

Jin et al., "Recombinant Human Respiratory Syncytial Virus (RSV) from cDNA and Construction of Subgroup A and B Chimeric RSV," *Virology* 251:206-214, 1998.

Jin et al., "Respiratory Syncytial Virus that Lacks Open Reading Frame 2 of the M2 Gene (M2-2) has Altered Growth Characteristics and is Attenuated in Rodents," *J. Virol.* 74:74-82, 2000.

Juhasz et al., "The Temperature-Sensitive (*ts*) Phenotype of a Cold-Passaged (*cp*)Live Attenuated Respiratory Syncytial Virus Vaccine Candidate, Designated *cpts*530, Results from a Single Amino Acid Substitution in the L Protein," *J. Virol.* 71:5814-5819, 1997.

Karaca et al., "Recombinant Fowlpox Viruses Coexpressing Chicken Type I IFN and Newcastle Disease Virus HN and F Genes: Influence of IFN on Protective Efficacy and Humoral Responses of Chickens Following in ovo or Post-hatch Administration of Recombinant Viruses," *Vaccine* 16:1469-1503, 1998.

Karupiah et al., "Interferon γ is Involved in the Recovery of Athymic Nude Mice from Recombinant Vaccinia Virus/Interleukin 2 Infection," *J. Ex. Med.* 172:1495-1503, 1990.

Karupiah et al., "Elevated Natural Killer Cell Responses in Mice Infected with Recombinant Vaccinia Virus Encoding Murine IL-2," *J. Immunol.* 144:290-298, 1990.

Karupiah et al., "Immunobiology of Infection with Recombinant Vaccinia Virus Encoding Murine IL-2," *J. Immunol.* 147:4327-4332, 1991.

Kato et al., "Initiation of Sendai Virus Multiplication from Transfected cDNA or RNA with Negative or Positive Sense," *Genes to Cells* 1:569-579, 1996.

Kato et al., "The Paramyxovirus, Sendai Virus, V Protein Encodes a Luxury Function Required for Viral Pathogenesis," *EMBO. J.* 16:578-587, 1997.

Kohonen-Corish, "Immunodeficient Mice Recover from Infection with Vaccinia Virus Expressing Interferon-γ," *Eur. J. Immunol.* 20:157-161, 1990.

Kuo et al., "Effect of Mutations in the Gene-Start and Gene-End Sequence Motifs on Transcription of Monocistronic and Dicistronic Minigenomes of Respiratory Syncytial Virus," *J. Virol.* 70:6892-6901, 1996.

Kurotani et al., "Sendai Virus C Proteins are Categorically Nonessential Gene Products but Silencing Their Expression Severely Impairs Viral Replication and Pathogenesis," *Genes to Cells.* 3:111-124, 1998.

Latorre et al., "The Various Sendai Virus C Proteins Are Not Functionally Equivalent and Exert both Positive and Negative Effects on Viral FNA Accumulation During the Course of Infection," *J. Virol.* 72:5984-5993, 1998.

Lawson et al., "Recombinant Vesicular Stomatitis Viruses from DNA," *Proc. Natl. Acad. Sci. USA* 92:4477-4481, 1995.

Leong et al., "Selective Induction of Immune Responses by Cytokines Coexpressed in Recombinant Fowlpox Virus," *J. Virol.* 68:8125-8130, 1994.

Mallipeddi, et al., "Sequence Comparison Between the Phosphoprotein mRNAs of Human and Bovine Respiratory Syncytial Viruses identifies a Divergent Domain in the Predicted Protein," *J. Gen. Virol.* 73:2441-2444, 1992.

Mallipeddi, et al., "Sequence Variability of the Glycoprotein Gene of Bovine Respiratory Syncytial Virus," *J. Gen. Virol.* 74:2001-2004, 1993.

Murphy et al., "Current Approaches to the Development of Vaccines Effective Against Parainfluenza and Respiratory Syncytial Viruses," *Virus Res* 11:1-15, 1988.

Palese et al., "Negative-Strand RNA Viruses: Genetic Engineering and Applications," *Proc. Natl. Acad. Sci. USA* 93:11354-11358, 1996.

Pastey et al., "Structure and Sequence Comparison of Bovine Respiratory Syncytial Virus Fusion Protein," *Virus. Res.* 29:195-202, 1993.

Pastey et al., "Nucleotide Sequence Analysis of the Non-Structural NS1(1C) and NS2 (1B) Protein Genes of Bovine Respiratory Syncytial Virus," *J. of Gen. Virol.* 76:193-197, 1995.

Peeters et al., "Rescue of Newcastle Disease Virus from Cloned cDNA: Evidence that Cleavability of the Fusion Protein is a Major Determinant for Virulence," *J. Virol.* 73:5001-5009, 1999.

Radecke et al., "Rescue of Measles Viruses from Cloned DNA," *EMBO J.* 14:5773-5784, 1995.

Radecke et al., "The Nonstructural C Protein is not Essential for Multiplication of Edmonston B Strain Measles Virus in Cultured Cells," *Virology* 217:418-21, 1996.

Ramsay et al., "Enhancement of Mucosal IgA Responses by Interleukins 5 and 6 Encoded in Recombinant Vaccine Vectors," *Reprod. Fertil. Dev.* 6:389-392, 1994.

Ramshaw et al., "Recovery of Immunodeficient Mice from a Vaccinia Virus/IL-2 Recombinant Infection," *Nature* 329:545-546, 1987.

Ramshaw et al., "Expression of Cytokines by Recombinant Vaccinia Viruses: A Model for Studying Cytokines in Virus Infections in vivo," *Immunol. Rev.* 127:157-182, 1992.

Ramshaw et al., "Cytokine Expression by Recombinant Viruses—a New Vaccine Strategy," *Trends Biotechnol.* 10:424-426, 1992.

Randhawa et al., "Nucleotide Sequences of the Genes Encoding the Putative Attachment Glycoprotein (G) of Mouse and Tissue Culture-Passaged Strains of Pneumonia Virus of Mice," *Virology* 207:240-245, 1995.

Roberts et al., "The Membrane-Associated and Secreted Forms of the Respiratory Syncytial Virus Attachment Glycoprotein G are Synthesized from Alternative Initiation Codons," *J. Virol.* 68:4538-4546, 1994.

Roberts et al., "Recovery of Negative-Strand RNA Viruses from Plasmid DNAs: A Positive Approach Revitalizes a Negative Field," *Virology* 247:1-6, 1998.

Rolph et al., "Recombinant Viruses as Vaccines and Immunological Tools," *Curr. Opin. Immunol.* 9:517-524, 1997.

Rolph et al., "A Recombinant Vaccinia Virus Encoding Inducible Nitric Oxide Synthase is Attenuated in vivo," *J. Virol.* 70:7678-7685, 1996.

Sakai et al., "Accommodation Of Foreign Genes Into The Sendai Virus Genome: Sizes Of Inserted Genes And Viral Replication," *FEBS Letters* 456:221-226, 1999.

Sambhi et al., "Local Production of Tumor Necrosis Factor Encoded by Recombinant Vaccinia Virus is Effective in Controlling Viral Replication in vivo," *Proc. Natl. Acad. Sci. USA* 88:4025-4029, 1991.

Schneider et al., "Recombinant Measles Viruses defective for RNA Editing and V Protein Synthesis Are Viable in Cultured Cells," *Virology* 277:314-322, 1997.

Schnell et al., "Infectious Rabies Viruses from Cloned cDNA," *EMBO J.* 13:4195-4203, 1994.

Sharma et al., "Interleukin-4 Mediates Down Regulation of Antiviral Cytokine Expression and Cytotoxic T- Lymphocyte Responses and Exacerbates Vaccinia Virus Infection in vivo," *J. Virol.* 70:7103-7107, 1996.

Teng et al., "Identification of the Respiratory Syncytial Virus Proteins Required for Formation and Passage of Helper-Dependent Infectious Particles," *J. Virol.* 72:5707-5716, 1998.

Teng et al., "Altered Growth Characteristics of Recombinant Respiratory Syncytial Viruses Which do not Produce NS2 Protein," *J. Virol.* 73:466-473, 1999.

Wathen et al., "Characterization of a Novel Human Respiratory Syncytial Virus Chimeric FG Glycoprotein Expressed Using a Baculovirus Vector," *J. Gen. Virol.* 70:2625-2635, 1989.

Whelan et al., "Efficient Recovery Of Infectious Vesicular Stomatitis Virus Entirely From cDNA Clones," *Proc. Natl. Acad. Sci. USA* 92:8388-8392, 1995.

Whitehead et al., "A Single Nucleotide Substitution in the Transcription Start Signal of the M2 Gene of Respiratory Syncytial Virus Vaccine Candidate *cpts*248/404 is the Major Determinant of the Temperature-Sensitive and Attenuation Phenotypes," *Virology* 247:232-239, 1998a.

Whitehead et al., "Recombinant Respiratory Syncytial Virus (RSV) Bearing a Set of Mutations from cold-Passaged RSV is Attenuated in Chimpanzees," *J. Virol.* 72:4467-4471, 1998b.

Whitehead et al., "Recombinant Respiratory Syncytial Virus Bearing a Deletion of Either the NS2 or SH Gene is Attenuated in Chimpanzees," *J. Virol.* 73:3438-3442, 1999.

Zamora et al., "Sequence Analysis of M2 mRNA of Bovine Respiratory Syncytial Virus Obtained from an F-M2 dicistronic mRNA Suggest Structural Homology with that of Human Respiratory Syncytial Virus," *J. Gen. Virol.* 73:737-741, 1992.

Zamora et al., "Gene Junction Sequences of Bovine Respiratory Synctytial Virus," *Virus Res.* 24:115-121, 1992.

\* cited by examiner

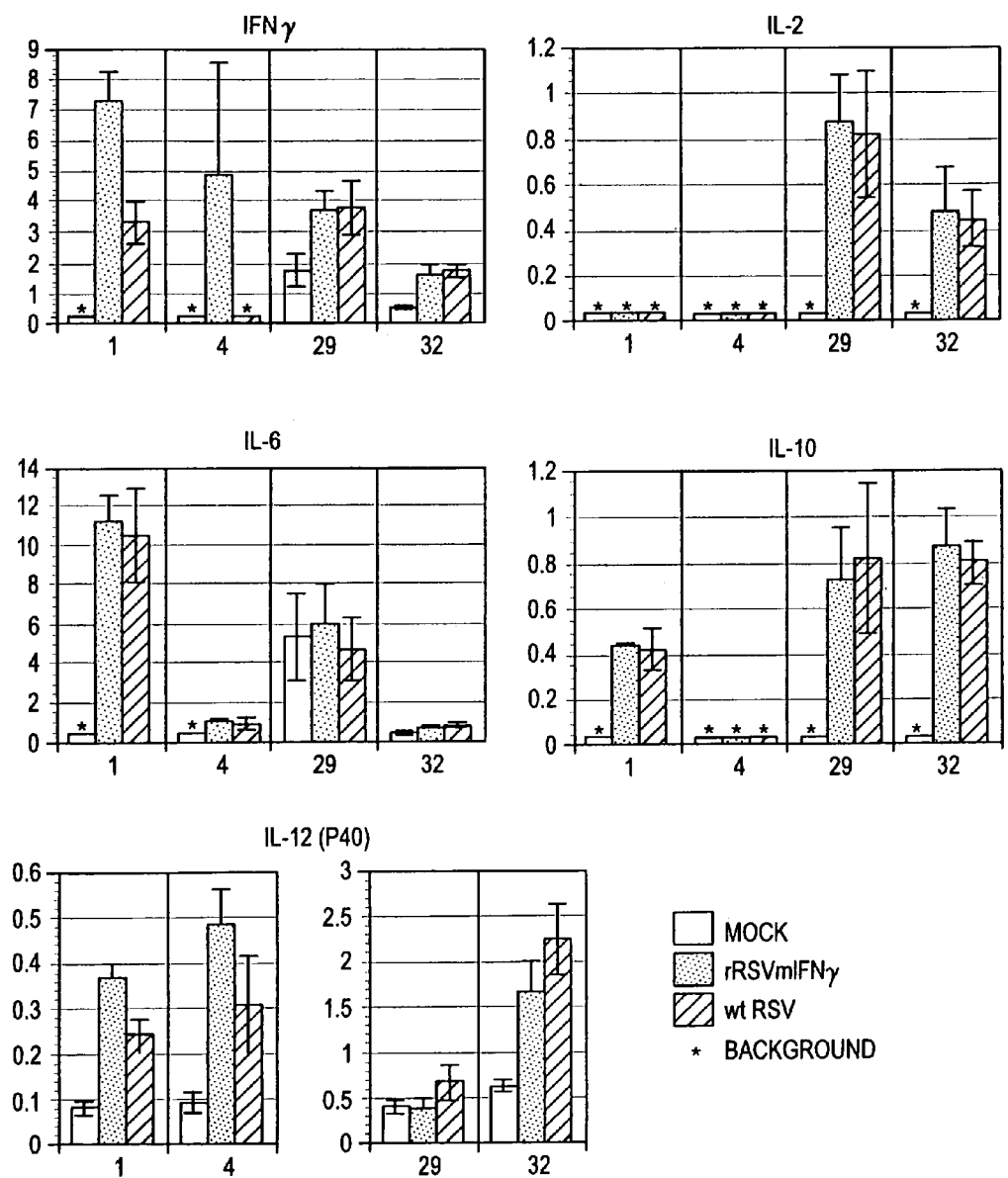

POLYNUCLEOTIDES ENCODING RECOMBINANT RESPIRATORY SYNCYTIAL VIRUSES EXPRESSING IMMUNE MODULATORY MOLECULES

CROSS-REFERENCES TO RELATED APPLICATIONS

This application is a divisional of U.S. patent application Ser. No. 09/614,285, filed Jul. 12, 2000, now U.S. Pat. No. 6,699,476 which claims the benefit of U.S. Provisional Patent Application No. 60/143,425, filed Jul. 13, 1999. This application also claims priority to and is a continuation-in-part of U.S. patent application Ser. No. 09/291,894, filed Apr. 13, 1999, issued Feb. 10, 2004 as U.S. Pat. No. 6,689,367, which is a continuation-in-part of U.S. patent application Ser. No. 08/892,403, filed Jul. 15, 1997, issued on Nov. 30, 1999 as U.S. Pat. No. 5,993,824, which is entitled to priority from U.S. Provisional Application No. 60/047,634, filed May 23, 1997; 60/046,141, filed May 9, 1997; and 60/021,773, filed Jul. 15, 1996. Each of the foregoing priority disclosures is incorporated herein by reference.

BACKGROUND OF THE INVENTION

Human respiratory syncytial virus (HRSV) is the leading viral cause of serious pediatric respiratory tract disease worldwide (Collins, et al., *Fields Virology* 2:1313-1352, 1996; incorporated herein by reference). RSV outranks all other microbial pathogens as a cause of pneumonia and bronchiolitis in infants under one year of age. Virtually all children are infected by two years of age, and reinfection occurs with appreciable frequency in older children and young adults (Chanock et al., in *Viral Infections of Humans*, 3rd ed., A. S. Evans, ed., Plenum Press, N.Y., 1989; incorporated herein by reference). RSV is responsible for more than one in five pediatric hospital admissions due to respiratory tract disease, and in the United States alone causes nearly 100,000 hospitalizations and 4,500 deaths yearly. (Heilman, *J. Infect. Dis.* 161:402-6, 1990; incorporated herein by reference). In addition, there is evidence that serious respiratory tract infection early in life can initiate or exacerbate asthma (Sigurs, et al., *Pediatrics* 95:500-505, 1995; incorporated herein by reference).

While RSV usually is thought of in the context of the pediatric population, it also is recognized as an important agent of serious disease in the elderly (Falsey et al., *J. Infect. Dis.* 172:389-394, 1995; incorporated herein by reference). RSV also causes life-threatening disease in certain immunocompromised individuals, such as bone marrow transplant recipients (Fouillard, et al., *Bone Marrow Transplant* 9:97-100, 1992; incorporated herein by reference).

For treatment of RSV, one chemotherapeutic agent, ribavirin, is available. However, its efficacy and use are controversial. There are also licensed products for RSV intervention which are composed of pooled donor IgG (Groothuis et al., *N. Engl. J. Med.* 329:1524-1530, 1993; incorporated herein by reference) or a humanized RSV-specific monoclonal antibody. These are administered as passive immunoprophylaxis agents to high-risk individuals. While these products are useful, their high cost and other factors, such as lack of long-term effectiveness, make them inappropriate for widespread use. Other disadvantages include the possibility of transmitting blood-borne viruses and the difficulty and expense in preparation and storage. Moreover, the history of the control of infectious diseases, and especially diseases of viral origin, indicates the primary importance of vaccines.

Despite decades of investigation to develop effective vaccine agents against RSV, no safe and effective vaccine has yet been approved to prevent the severe morbidity and significant mortality associated with RSV infection. Failure to develop successful vaccines relates in part to the fact that small infants have diminished serum and secretory antibody responses to RSV antigens. Thus, these individuals suffer more severe infections from RSV, whereas cumulative immunity appears to protect older children and adults against more serious impacts of the virus.

The mechanisms of immunity in RSV infection have recently come into focus. Secretory antibodies appear to be most important in protecting the upper respiratory tract, whereas high levels of serum antibodies are thought to have a major role in resistance to RSV infection in the lower respiratory tract. RSV-specific cytotoxic T cells, another effector arm of induced immunity, are also important in resolving an RSV infection. However, while this latter effector can be augmented by prior immunization to yield increased resistance to virus challenge, the effect is short-lived. The F and G surface glycoproteins are the two major protective antigens of RSV, and are the only two RSV proteins which have been shown to induce RSV neutralizing antibodies and long term resistance to challenge (Collins et al., *Fields Virology*, Fields et al. eds., 2:1313-1352, Lippincott-Raven, Philadelphia, 1996; Connors et al., *J. Virol.* 65 (3):1634-1637, 1991; incorporated herein by reference). The third RSV surface protein, SH, did not induce RSV-neutralizing antibodies or significant resistance to RSV challenge.

An obstacle to developing live RSV vaccines is the difficulty in achieving an appropriate balance between attenuation and immunogenicity. Other obstacles include the genetic instability of some attenuated viruses, the relatively poor growth of RSV in cell culture, and the instability of the virus particle. In addition the immunity which is induced by natural infection is not fully protective against subsequent infection. A number of factors probably contribute to this, including the relative inefficiency of the immune system in restricting virus infection on the luminal surface of the respiratory tract, the short-lived nature of local mucosal immunity, rapid and extensive virus replication, reduced immune responses in the young due to immunological immaturity, immunosuppression by transplacentally derived maternal serum antibodies, and certain features of the virus such as a high degree of glycosylation of the G protein. Also, as will be described below, RSV exists as two antigenic subgroups A and B, and immunity against one subgroup is of reduced effectiveness against the other.

Although RSV can reinfect multiple times during life, reinfections usually are reduced in severity due to protective immunity induced by prior infection, and thus immunoprophylaxis is feasible. A live-attenuated RSV vaccine would be administered intranasally to initiate a mild immunizing infection. This has the advantage of simplicity and safety compared to a parenteral route. It also provides direct stimulation of local respiratory tract immunity, which plays a major role in resistance to RSV. It also abrogates the immunosuppressive effects of RSV-specific maternally-derived serum antibodies, which typically are found in the very young. Also, while the parenteral administration of RSV antigens can sometimes be associated with immunopathologic complications (Murphy et al., *Vaccine* 8(5):497-502, 1990; incorporated herein by reference), this has never been observed with a live virus.

A formalin-inactivated virus vaccine was tested against RSV in the mid-1960s, but failed to protect against RSV infection or disease, and in fact exacerbated symptoms during subsequent infection by the virus. (Kim et al., *Am. J. Epide-*

*miol.*, 89:422-434, 1969; Chin et al., *Am. J. Epidemiol.*, 89:449-463, 1969; Kapikian et al., *Am. J. Epidemiol.*, 89:405-421, 1969; incorporated herein by reference).

More recently, vaccine development for RSV has focused on attenuated RSV mutants. Friedewald et al., (*J. Amer. Med. Assoc.* 204:690-694, 1968; incorporated herein by reference) reported a cold passaged mutant of RSV (cpRSV) which appeared to be sufficiently attenuated to be a candidate vaccine. This mutant exhibited a slightly increased efficiency of growth at 26° C. compared to its wild-type (wt) parental virus, but its replication was neither temperature sensitive nor significantly cold-adapted. The cold-passaged mutant, however, was attenuated for adults. Although satisfactorily attenuated and immunogenic for infants and children who had been previously infected with RSV (i.e., seropositive individuals), the cpRSV mutant retained a low level virulence for the upper respiratory tract of seronegative infants.

Similarly, Gharpure et al., (*J. Virol.* 3:414-421, 1969; incorporated herein by reference) reported the isolation of temperature sensitive RSV (tsRSV) mutants which also were promising vaccine candidates. One mutant, ts-1, was evaluated extensively in the laboratory and in volunteers. The mutant produced asymptomatic infection in adult volunteers and conferred resistance to challenge with wild-type virus 45 days after immunization. Again, while seropositive infants and children underwent asymptomatic infection, seronegative infants developed signs of rhinitis and other mild symptoms. Furthermore, instability of the ts phenotype was detected. Although virus exhibiting a partial or complete loss of temperature sensitivity represented a small proportion of virus recoverable from vaccinees, it was not associated with signs of disease other than mild rhinitis.

These and other studies revealed that certain cold-passaged and temperature sensitive RSV strains were underattenuated and caused mild symptoms of disease in some vaccinees, particularly seronegative infants, while others were overattenuated and failed to replicate sufficiently to elicit a protective immune response, (Wright et al., *Infect. Immun.* 37:397-400, 1982; incorporated herein by reference). Moreover, genetic instability of candidate vaccine mutants has resulted in loss of their temperature sensitive phenotype, further hindering development of effective RSV vaccines. See generally, (Hodes et al., *Proc. Soc. Exp. Biol. Med.* 145:1158-1164, 1974; McIntosh et al., *Pediatr. Res.* 8:689-696, 1974; and Belshe et al., *J. Med. Virol.* 3:101-110, 1978; incorporated herein by reference).

As an alternative to live-attenuated RSV vaccines, investigators have also tested subunit vaccine candidates using purified RSV envelope glycoproteins. The glycoproteins induced resistance to RS virus infection in the lungs of cotton rats, (Walsh et al., *J. Infect. Dis.* 155:1198-1204, 1987; incorporated herein by reference), but the antibodies had very weak neutralizing activity and immunization of rodents with purified subunit vaccine led to disease potentiation (Murphy et al., *Vaccine* 8:497-502, 1990; incorporated herein by reference).

Recombinant vaccinia virus vaccines which express the F or G envelope glycoprotein have also been explored. These recombinants express RSV glycoproteins which are indistinguishable from the authentic viral counterpart, and rodents infected intradermally with vaccinia-RSV F and G recombinants developed high levels of specific antibodies that neutralized viral infectivity. Indeed, infection of cotton rats with vaccinia-F recombinants stimulated almost complete resistance to replication of RSV in the lower respiratory tract and significant resistance in the upper tract. (Olmsted et al., *Proc. Natl. Acad. Sci. USA* 83:7462-7466, 1986; incorporated herein by reference). However, immunization of chimpanzees with vaccinia-F and -G recombinant provided almost no protection against RSV challenge in the upper respiratory tract (Collins et al., *Vaccine* 8:164-168, 1990; incorporated herein by reference) and inconsistent protection in the lower respiratory tract (Crowe et al., *Vaccine* 11:1395-1404, 1993; incorporated herein by reference).

Despite these various efforts to develop an effective RSV vaccine, no licensed vaccine has yet been approved for RSV. The unfulfilled promises of prior approaches underscores a need for new strategies to develop RSV vaccines, and in particular methods for manipulating recombinant RSV to incorporate genetic changes that yield new phenotypic properties in viable, attenuated RSV recombinants. However, manipulation of the genomic RNA of RSV and other non-segmented negative-sense RNA viruses has heretofore proven difficult. Major obstacles in this regard include non-infectivity of naked genomic RNA of these viruses and, in the case of RSV, poor viral growth in tissue culture, lengthy replication cycles, virion instability, a complex genome, and a refractory organization of gene products.

Recombinant DNA technology has made it possible to recover infectious non-segmented negative-stranded RNA viruses from cDNA, to genetically manipulate viral clones to construct novel vaccine candidates, and to rapidly evaluate their level of attenuation and phenotypic stability (for reviews, see Conzelmann, *J. Gen. Virol.* 77:381-389, 1996; Palese et al., *Proc. Natl. Acad. Sci. U.S.A.* 93:11354-11358, 1996; incorporated herein by reference). In this context, recombinant rescue has been reported for infectious respiratory syncytial virus (RSV), parainfluenza virus (PIV), rabies virus (RaV), vesicular stomatitis virus (VSV), measles virus (MeV), rinderpest virus and Sendai virus (SeV) from cDNA-encoded antigenomic RNA in the presence of essential viral proteins (see, e.g., Garcin et al., *EMBO J.* 14:6087-6094, 1995; Lawson et al., *Proc. Natl. Acad. Sci. U.S.A.* 92:4477-4481, 1995; Radecke et al., *EMBO J.* 14:5773-5784, 1995; Schnell et al., *EMBO J.* 13:4195-4203, 1994; Whelan et al., *Proc. Natl. Acad. Sci. U.S.A.* 92:8388-8392, 1995; Hoffman et al., *J. Virol.* 71:4272-4277, 1997; Pecters et al., *J. Virol.* 73:5001-5009, 1999; Kato et al., *Genes to Cells* 1:569-579, 1996; Roberts et al., *Virology* 247(1), 1-6, 1998; Baron et al., *J. Virol.* 71:1265-1271, 1997; International Publication No. WO 97/06270; U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. Pat. No. 5,993,824, issued Nov. 30, 1999 (corresponding to International Publication No. WO 98/02530); U.S. Provisional Patent Application Ser. No. 60/129,006, filed Apr. 13, 1999; Collins, et al., *Proc. Nat. Acad. Sci. USA* 92:11563-11567, 1995; Bukreyev, et al., *J. Virol.* 70:6634-6641, 1996, Juhasz et al., *J. Virol.* 71(8):5814-5819, 1997; Durbin et al., *Virology* 235:323-332, 1997; He et al. *Virology* 237:249-260, 1997; Baron et al. *J. Virol.* 71:1265-1271, 1997; Whitehead et al., *Virology* 247(2):232-239, 1998a; Whitehead et al., *J. Virol.* 72(5):4467-4471, 1998b; Jin et al. *Virology* 251:206-214, 1998; and Whitehead et al., *J. Virol.* 73:(4)3438-3442, 1999, and Bukreyev, et al., *Proc. Nat. Acad. Sci. USA* 96:2367-2372, 1999, Bucholz et al., *J. Virol.* 73:251-259, 1999; Collins et al., *Virology* 259:251-255, 1999, each incorporated herein by reference in its entirety for all purposes).

Based on these developments in recombinant DNA technology, it is now possible to recover infectious RSV from cDNA and to design and implement various genetic manipulations to RSV clones to construct novel vaccine candidates. Thereafter, the level of attenuation and phenotypic stability, among other desired phenotypic characteristics, can be evaluated.

One avenue of investigation toward developing recombinant vaccines has been to engineer viruses to express one or more cytokines or other potential anti-viral molecules. For the most part, these studies involved wild type vaccinia virus and were conducted with the goal of increasing basic understanding of host immunity and viral pathogenesis (see, e.g., Ramshaw et al. *Immunol. Rev.* 127:157-182, 1992; incorporated herein by reference). The potential utility of cytokine coexpression to improve immune responses for vaccine development has long been contemplated (Ramshaw et al., *Trends Biotechol* 10:424-426, 1992; incorporated herein by reference). However, the use of poxvirus as an object of study reduced the practical application of this concept since smallpox has been eradicated in the human population and the poxvirus vaccine no longer remains in active use.

Examples of these earlier studies investigating the possible utility of cytokine coexpression for vaccine development include a vaccinia virus engineered to express the cytokine interleukin 2 (IL-2). This recombinant virus was reported to be attenuated in immunodeficient athymic nude mice (Flexner et al., *Nature* 330:259-262, 1987; Ramshaw et al., *Nature* 329:545-546, 1987; incorporated herein by reference). The roles of various immune effectors in clearance and recovery have also been investigated (Karupiah et al., *J. Ex. Med.* 172:1495-1503, 1990; Karupiah et al., *J. Immunol.* 144:290-298, 1990; Karupiah et al., *J. Immunol.* 147:4327-4332, 1991; incorporated herein by reference). IL-2 expression by the vaccinia virus recombinant was shown to greatly reduce skin lesions formed by the vaccinia virus in primates, indicating significant attenuation. Despite these preliminary findings, antibody production was determined to be equivalent in the presence, or absence, of IL-2 (Flexner et al., *Vaccine* 8:17-21, 1990; incorporated herein by reference).

Another example of cytokine coexpression by a recombinant vaccinia virus involved interleukin 4 (IL-4), which was reported to downregulate antiviral cytokine expression and cytotoxic T cell responses, and to exacerbate the viral infection (Sharma et al., *J. Virol.* 70:7103-7107, 1996; incorporated herein by reference). In yet another study, expression of nitric oxide synthetase by recombinant vaccinia virus was highly attenuating, demonstrating the importance of this host defense mechanism in controlling vaccinia virus infection (Rolph et al., *J. Virol.* 70:7678-7685, 1996; incorporated herein by reference). Coexpression of IL-5 or IL-6 by a recombinant vaccinia virus resulted in a 4-fold elevation in the level of local IgA (Ramsay et al., *Reprod. Fertil. Dev.* 6:389-392, 1994; incorporated herein by reference). Coexpression of tumor necrosis factor (TNF) alpha by a recombinant vaccinia virus improved the capacity of mice to control infection, suggesting that this molecule is involved in host defenses against the virus (Sambhi et al., *Proc. Natl. Acad. Sci. USA* 88:4025-4029, 1991; incorporated herein by reference). Expression of murine IFNγ by a recombinant vaccinia virus greatly reduced virus replication in normal or immune-compromised mice (Kohonen-Corish, *Eur. J. Immunol.* 20:157-161, 1990; incorporated herein by reference).

These studies have also been extended to retroviruses. Recently, simian immunodeficiency virus (SUV) expressing IL-2 was constructed (Gundlach et al., *J. Virol.* 71:2225-2232, 1997; incorporated herein by reference). In rhesus monkeys infected with the IL-2-expressing virus the SIV-specific T-cell proliferative response and the antibody titers were similar to those of control virus. SIV-specific CTL were detected in monkeys infected with the IL-2-expressing virus and in two of four control animals. In another study, a SIV recombinant lacking the nef gene and containing the IFNλ gene was attenuated in vivo, but the cytokine gene was unstable after several weeks of replication in vivo and, in addition, the attenuation was associated with reduced immunogenicity (Giavedoni et al., *J. Virol.* 71:866-872, 1997; incorporated herein by reference).

Studies with large double-stranded poxviruses, which have approximately 185 ORFs and encode a number of proteins which interfere with host defenses, or with human immunodeficiency virus which also interferes with host defense, are poor models for the nonsegmented negative strand RNA viruses. It has been previously demonstrated that a foreign gene can be expressed from the genome of recombinant respiratory syncytial virus (RSV), and that it is stably maintained (Bukreyev *J. Virol.* 70: 6634-6641, 1996, incorporated herein by reference). This indicates that it is feasible to coexpress proteins such as cytokines, chemokines, ligands, and other molecules which might alter, increase or otherwise enhance the host response to RSV. The expression of one or more immune modulatory molecules from a recombinant RSV is desirable because it would provide for expression at the local site of RSV antigen production. Furthermore, coexpression obviates the need to separately prepare and administer the immune modulator. However, the strategy of expressing an immune modulator from the genome of a non-retrovirus, i.e., a positive-sense, double-stranded, or negative-sense RNA virus, had not been previously explored.

There is presently a need for augmentation and modification of host immune responses to RSV. This is because an RSV vaccine will be administered to very young infants, an age group which is known to mount immune responses that are less effective and in some respects different than those of adults. For example, neutralizing antibody responses and cytotoxic T cell responses to RSV are reduced in the very young (Kovarik and Siegrist, *Immunol. Today* 19: 150-152, 1998; Kovarik and Siegrist, *Immunol. Cell. Biol.* 76:222-236, 1998; Murphy et al., *J. Clin. Microbiol.* 24:894-989, 1986; Risdon et al., *Cell. Immunol.* 154:14, 1994; incorporated herein by reference). It is generally recognized that the neonatal immune system is biased towards a Th-2 type T helper cell response (i.e., the T helper cell subset defined by IL-4 secretion) (Early and Reen, *Eur. J. Immunol.* 26:2885-2889, 1996; incorporated herein by reference). T cells from newborns have reduced helper cell activity for B cells, and produce lower quantities of a number of cytokines, including IL-2, interferon gamma (IFNγ), and IL-4 (Splawski et al., *J. Clin. Invest.* 87, 454, 1991; Hassan and Reen, *Scand. J. Immunol.* 39:597, 1994; Wilson, *Pediatr.* 54:118, 1991; incorporated herein by reference). Also, young infants typically possess transplacentally-derived RSV-specific IgG, which can interfere with or alter immune responses (Murphy et al., *J. Clin. Microbiol.* 24:894-989, 1986 and 23:1009-1014, 1986; Siegrist et al., *Eur. J. Immunol.* 28:4138-4148, 1998; incorporated herein by reference). Finally, certain RSV immunizations can be associated with immunopathologic complications (Murphy et al., *Vaccine* 8:497-502, 1990; Waris et al., *J. Virol.* 71:6935-6939, 1997; incorporated herein by reference). Although this typically is not observed with live-attenuated virus infections, there is evidence that individual RSV antigens, and most notably the G protein, have the potential to induce immunopathologic responses even when expressed by live virus (Johnson et al., *J. Virol.* 72:2871-2880; incorporated herein by reference). These many factors involved in RSV immune responses, immune-mediated protection, and immunopathologic responses indicate a need for developing methods to modulate host responses to an RSV vaccine.

In summary, an urgent need presents itself in the art to develop additional tools and methods to engineer safe and effective vaccines that will alleviate the serious health problems attributable to RSV. In this context, it is necessary to develop a broad and diverse menu of genetic modifications that can be employed, alone or in combination with other types of genetic manipulations, to construct infectious, attenuated RSV vaccine candidates useful for broad vaccine use. Useful manipulations to a live attenuated RSV vaccine virus might include coexpression by a recombinant RSV clone of or more one factors that modulate host immune responses and immune-mediated protection. Surprisingly, the present invention fulfills this need by providing additional tools for constructing infectious, attenuated RSV vaccine candidates.

SUMMARY OF THE INVENTION

The present invention provides recombinant RSV (rRSV) which are engineered to express one or more immune modulatory molecule(s). The recombinant virus has a modified genome or antigenome that incorporates a polynucleotide sequence encoding the immune modulatory molecule which is expressed by the virus in infected cells. Preferred immune modulatory molecules for use within the invention are cytokines. However, various other immune modulatory molecules, including chemokines, chemokine or cytokine anatagonists, surface or soluble receptors, adhesion molecules, ligands, and the like, are also useful to alter aspects of viral biology and/or host immune responses to RSV. In more detailed embodiments, the immune modulator is a cytokine selected from an interleukin 2 (IL-2), interleukin 4 (IL-4), interferon gamma (IFN$\lambda$), or granulocyte-macrophage colony stimulating factor (GM-CSF) molecule.

Cytokines and other immune modulatory molecules can be incorporated in a recombinant RSV of the invention in such a manner that they are expressed by the virus in infected cells and modify one or more aspects of viral biology. For example, incorporation and expression of an immune modulator may alter viral infectivity, replication and/or pathogenicity, and may elicit or change one or more host immune responses, for example an anti-RSV neutralizing antibody response, a T-helper cell response, a cytotoxic T cell (CTL) response, and/or a natural killer (NK) cell response.

The invention provides for the intracellular coexpression from a recombinant RSV of a wide variety of proteins found in nature or engineered by recombinant DNA technology. These proteins typically affect hematopoietic cells or, alternatively, can block natural signals and interactions of hematopoietic cells. To construct these recombinant viruses, the viral genome or antigenome is modified to incorporate a polynucleotide sequence encoding the cytokine or other immune modulator molecule(s). The polynucleotide sequences is added or substituted within the genome or antigenome, typically as a separate gene with its own gene start (GS) and gene end (GE) signals. Generally, the polynucleotide sequence encoding the immune modulator is added or substituted into an intergenic or other non-coding region of the recombinant RSV genome or antigenome, at any suitable locus that does not disrupt an open reading frame within the genome or antigenome.

The level of expression of the cytokine or other immune modulator can be adjusted by altering the gene order position of the cytokine-encoding polynucleotide within the recombinant genome or antigenome. For example, the cytokine-encoding polynucleotide can be introduced at any intergenic position or non-coding region within any of the RSV genes. The more upstream or "promoter-proximal" the location of introduction, the higher the level of expression of the modulator will be.

Another method for inserting a gene or genome segment encoding an immune modulatory factor into RSV is to place the cDNA under the control of RSV gene-start and gene-end signals as described above, but to insert the cDNA so that the gene is expressed from the antigenome rather than from the genome. Ideally, the foreign gene is placed immediately downstream from the promoter at the 3' end of the antigenome, such that this promoter-proximal location ensures a high level of expression.

Yet another method for expressing a cytokine or other immune modulator from RSV to place the ORF for the gene under control of a mammalian internal ribosome entry site, and to insert this ORF into the downstream noncoding region of any one or more of the RSV genes.

Yet another method for expression is by the construction of chimeric or fusion proteins. For example, a protein ectodomain which is desired to be expressed at the surface of the infected cell and virion can be attached to the downstream end of the SH ORF or other non-essential gene, such that the reading frame is undisturbed and a chimeric protein results. In this configuration, the SH moiety provides the signal and membrane anchor, and the C-terminal attached domain is displayed extracellularly.

The expression of one or more immune modulatory molecules by a recombinant RSV is desirable because it provides for expression of the immune modulatory molecule at a local site of RSV antigen production. Thus, coexpression of immune modulatory molecules in accordance with the teachings of the invention obviates the need to separately prepare and administer the immune modulator(s). In addition, recombinant RSV of the invention have other desirable characteristics that are useful for vaccine development. Alteration of the recombinant genome or antigenome to express a cytokine, for example, yields vaccine candidates that exhibit one or more novel characteristics selected from (i) a change in viral growth in cell culture; (ii) a change in viral attenuation in the upper and/or lower respiratory tract of an infected host; (iii) a change in viral plaque size; and/or (vi) a change in immunogenicity, or, alternatively or concomitantly, an ability to elicit an altered host response, e.g., an increased anti-RSV neutralizing antibody response, T-helper cell response, cytotoxic T cell (CTL) response, and/or natural killer (NK) cell response, compared to a host response elicited by wild type or parental (i.e., not expressing cytokine) RSV.

Within preferred aspects of the invention, recombinant RSV express high levels of the introduced cytokine or other immune modulator, for example up to 2.5 micrograms/ml as measured in the medium of infected tissue culture cells. The recombinant viruses are attenuated in vitro and in vivo, yet they exhibit a high level of protective efficacy against wild type RSV in vaccinated subjects are engineered to express undiminished or, more typically, increased levels of viral antigen(s) while also exhibiting an attenuated phenotype. Immunogenic potential is thus preserved due to the undiminished or increased mRNA transcription and antigen expression, while attenuation is achieved through concomitant reductions in RNA replication and virus growth. This novel suite of phenotypic traits is highly desired for vaccine development. Other useful phenotypic changes that are observed in recombinant RSV engineered to express an immune modulator(s) include a change in plaque size and altered cytopathogenicity compared to corresponding wild-type or mutant parental RSV strains.

In combination with the phenotypic effects provided in recombinant RSV which are modified to express a cytokine or other immune modulator, it is often desirable to adjust the attenuation phenotype by introducing additional mutations that increase or decrease attenuation of the recombinant virus. Thus, candidate vaccine strains can be further attenuated by incorporation of at least one, and preferably two or more different attenuating mutations, for example mutations identified from a panel of known, biologically derived mutant RSV strains. Preferred human mutant RSV strains are cold passaged (cp) and/or temperature sensitive (ts) mutants, for example the mutants designated "cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579)" (each deposited under the terms of the Budapest Treaty with the American Type Culture Collection (ATCC) of 10801 University Boulevard, Manassas, Va. 20110-2209, U.S.A., and granted the above identified accession numbers). From this exemplary panel of biologically derived mutants, a large "menu" of attenuating mutations is provided, each of which can be combined with any other mutation(s) within the panel for calibrating the level of attenuation and other desirable phenotypes in recombinant RSV of the invention for vaccine use. Additional mutations which can be thus adopted or transferred to RSV clones modified to express a cytokine or other immune modulator may be identified in various temperature sensitive (ts), cold passaged (cp), small plaque (sp), cold-adapted (ca) or host-range restricted (hr) mutant RSV strains. Additional attenuating mutations may be identified in non-RSV negative stranded RNA viruses and incorporated in RSV mutants of the invention by mapping the mutation to a corresponding, homologous site in the recipient RSV genome or antigenome and mutating the existing sequence in the recipient to the mutant genotype (either by an identical or conservative mutation), as described in U.S. Provisional Patent Application Ser. No. 60/129,006, filed Apr. 13, 1999. Additional useful mutations can be determined empirically by mutational analysis using recombinant minigenome systems and infectious virus as described in the references incorporated herein.

Recombinant RSV of the invention selected for vaccine use often have at least two and sometimes three or more attenuating mutations to achieve a satisfactory level of attenuation for broad clinical use. In one embodiment, at least one attenuating mutation occurs in the RSV polymerase gene L (either in the donor or recipient gene) and involves one or more nucleotide substitution(s) specifying an amino acid change in the polymerase protein specifying an attenuation phenotype which may or may not involve a temperature-sensitive (ts) phenotype. Recombinant RSV modified to express a cytokine or other immune modulator may incorporate a ts mutation in any additional RSV gene besides L, for example in the M2 gene. However, preferred vaccine candidates in this context incorporate one or more nucleotide substitutions in the large polymerase gene L resulting in an amino acid change at amino acid Asn43, Cys319, Phe521, Gln831, Met1169, Tyr1321, and/or his1690, as exemplified by the changes, Ile for Asn43, Leu for Phe521, Leu for Gln831, Val for Met1169, and Asn for Tyr1321. Other alternative amino acid changes, particularly conservative changes with respect to identified mutant residues, at these positions can of course be made to yield a similar effect as the identified, mutant substitution.

Additional desired mutations for incorporation into recombinant RSV of the invention include attenuating mutations specifying an amino acid substitution at Val267 in the RSV N gene, Glu218 and/or Thr523 in the RSV F gene, and a nucleotide substitution in the gene-start sequence of gene M2. Any combination of one or more of the attenuating mutations identified herein, up to and including a full complement of these mutations, may be incorporated in RSV modified to express an immune modulatory molecule to yield a suitably attenuated recombinant virus for use in selected populations or broad populations of vaccine recipients.

Attenuating mutations may be selected in coding portions of a recombinant RSV genome or antigenome or in non-coding regions such as a cis-regulatory sequence. Exemplary non-coding mutations include single or multiple base changes in a gene start sequence, as exemplified by a single or multiple base substitution in the M2 gene start sequence at nucleotide 7605 (nucleotide 7606 in an exemplary recombinant sequence).

In addition to the above described mutations, infectious RSV modified according to the invention can incorporate heterologous, coding or non-coding nucleotide sequences from any RSV or RSV-like virus, e.g., human, bovine, ovine, murine (pneumonia virus of mice), or avian pneumovirus, or from another enveloped virus, e.g., parainfluenza virus (PIV). Exemplary heterologous sequences include RSV sequences from one human RSV strain combined with sequences from a different human RSV strain in a RSV modified to express a cytokine or other immune modulator. For example, recombinant RSV of the invention may incorporate sequences from two or more wild-type or mutant RSV strains, for example mutant strains selected from cpts RSV 248, cpts 248/404, cpts 248/955, cpts RSV 530, cpts 530/1009, or cpts 530/1030. Alternatively, these novel mutants may incorporate sequences from two or more, wild-type or mutant human RSV subgroups, for example a combination of human RSV subgroup A and subgroup B sequences (see, International Application No. PCT/US/08802 and related U.S. Patent Application 60/021,773, 60/046,141, 60/047,634, Ser. Nos. 08/892,403, 09/291,894, each incorporated herein by reference). In yet additional aspects, one or more human RSV coding or non-coding polynucleotides are substituted with a counterpart sequence from a heterologous RSV or non-RSV virus, alone or in combination with one or more selected attenuating mutations, e.g., cp and/or ts mutations, to yield novel attenuated vaccine strains.

In related aspects of the invention, the disclosed modifications relating to the introduction of cytokine encoding sequences are incorporated within chimeric human-bovine RSV, which are recombinantly engineered to incorporate nucleotide sequences from both human and bovine RSV strains to produce an infectious, chimeric virus or subviral particle. Exemplary human-bovine chimeric RSV of the invention incorporate a chimeric RSV genome or antigenome comprising both human and bovine polynucleotide sequences, as well as a major nucleocapsid (N) protein, a nucleocapsid phosphoprotein (P), a large polymerase protein (L), and a RNA polymerase elongation factor. Additional RSV proteins may be included in various combinations to provide a range of infectious subviral particles, up to a complete viral particle or a viral particle containing supernumerary proteins, antigenic determinants or other additional components.

Chimeric human-bovine RSV for use within the invention are generally described in U.S. patent application entitled PRODUCTION OF ATTENUATED, HUMAN-BOVINE CHIMERIC RESPIRATORY SYNCYTIAL VIRUS VAC- CINES, filed by Bucholz et al. on Jun. 23, 2000 and identified by, and in its priority U.S. Provisional Patent Application Ser. No. 60/143,132 (each incorporated herein by reference). These chimeric recombinant RSV include a partial or complete "background" RSV genome or antigenome derived from or patterned after a human or bovine RSV strain or subgroup virus combined with one or more heterologous gene(s) or genome segment(s) of a different RSV strain or subgroup virus to form the human-bovine chimeric RSV genome or antigenome. In certain aspects of the invention, chimeric RSV incorporate a partial or complete bovine RSV background genome or antigenome combined with one or more heterologous gene(s) or genome segment(s) from a human RSV. In alternate aspects of the invention, RSV modified to express an immune modulatory molecule incorporate a partial or complete human RSV background genome or antigenome combined with one or more heterologous gene(s) or genome segment(s) from a bovine RSV.

Yet additional aspects of the invention involve changing the position of a gene or altering gene order to create or modify a RSV modified to express an immune modulatory molecule. In this context, a number of the foregoing incorporated references have focused on modification of the naturally-occurring order in RSV and other viruses. For example, in RSV the NS1, NS2, SH and G genes were deleted individually, and the NS1 and NS2 gene were deleted together, thereby shifting the position of each downstream gene relative to the viral promoter. For example, when NS1 and NS2 are deleted together, N is moved from position 3 to position 1, P from position 4 to position 2, and so on. Alternatively, deletion of any other gene within the gene order will affect the position (relative to the promoter) only of those genes which are located further downstream. For example, SH occupies position 6 in wild type virus, and its deletion does not affect M at position 5 (or any other upstream gene) but moves G from position 7 to 6 relative to the promoter. It should be noted that gene deletion also can occur (rarely) in a biologically-derived mutant virus. For example, a subgroup B RSV that had been passaged extensively in cell culture spontaneously deleted the SH and G genes (Karron et al., *Proc. Natl. Acad. Sci. USA* 94:13961-13966, 1997; incorporated herein by reference). Note that "upstream" and "downstream" refer to the promoter-proximal and promoter-distal directions, respectively (the promoter is at the 3' leader end of negative-sense genomic RNA).

Gene order shifting modifications (i.e., positional modifications moving one or more genes to a more promoter-proximal or promoter-distal location in the recombinant viral genome) to create or modify cytokine-expressing RSV of the invention result in viruses with altered biological properties. For example, RSV lacking NS1, NS2, SH, G, NS1 and NS2 together, or SH and G together, have been shown to be attenuated in vitro, in vivo, or both. It is likely that this phenotype was due primarily to the loss of expression of the specific viral protein. However, the altered gene map also likely contributed to the observed phenotype. This effect is well-illustrated by the SH-deletion virus, which grew more efficiently than wild type in some cell types, probably due to an increase in the efficiency of transcription, replication or both resulting from the gene deletion and resulting change in gene order and possibly genome size. In other viruses, such as RSV in which NS1 and/or NS2 were deleted, altered growth that might have occurred due to the change in gene order likely was obscured by the more dominant phenotype due to the loss of expression of the RSV protein(s).

Yet additional changes will be introduced to change the gene order of cytokine-expressing RSV in an effort to improve the properties of the recombinant virus as a live-attenuated vaccine (see, U.S. Provisional Patent Application entitled RESPIRATORY SYNCYTIAL VIRUS VACCINES EXPRESSING PROTECTIVE ANTIGENS FROM PROMOTOR-PROXIMAL GENES, filed by Krempl et al., Jun. 23, 2000 and identified by Appl. Ser. No. 60/213,708, incorporated herein by reference). In particular, the G and F genes may be shifted, singly and in tandem, to a more promoter-proximal position relative to their wild-type gene order. These two proteins normally occupy positions 7 (G) and 8 (F) in the RSV gene order (NS1-NS2-N-P-M-SH-G-F-M2-L). In order to increase the possibility of successful recovery, exemplary shifting manipulations have been performed in a version of RSV in which the SH gene had been deleted (Whitehead et al., *J. Virol.* 73:3438-42 (1999), incorporated herein by reference). This facilitates recovery because this virus makes larger plaques in vitro (Bukreyev et al., *J. Virol.*, 71:8973-82 (1997), incorporated herein by reference). G and F were then moved individually to position 1, or were moved together to positions 1 and 2, respectively. Surprisingly, recombinant RSV were readily recovered in which G or F were moved to position 1, or in which G and F were moved to positions 1 and 2, respectively.

Similarly extensive modifications in gene order for incorporation into cytokine-expressing RSV also have been achieved with two highly attenuated vaccine candidates in which the NS2 gene was deleted on its own, or in which the NS1 and NS2 genes were deleted together. In these two vaccine candidates, the G and F glycoproteins were moved together to positions 1 and 2 respectively, and the G, F and SH glycoproteins were deleted from their original downstream position. Thus, the recovered viruses G1F2$\Delta$NS2$\Delta$SH and G1F2/$\Delta$NS/$\Delta$NS2$\Delta$SH had two and three genes deleted respectively in addition to the shift of the G and F genes. To illustrate the extent of the changes involved, the gene orders of wild type RSV (NS1-NS2-N-P-M-SH-G-F-M2-L) and the G1F2/$\Delta$NS2$\Delta$SH virus (G-F-NS1-N-P-M-M2-L) or the $\Delta$NS1$\Delta$NS2$\Delta$SH (G-F-N-P-M-M2-L) can be compared. This shows that the positions of most or all of the genes relative to the promoter were changed. Nonetheless, these highly attenuated derivatives retained the capacity to be grown in cell culture.

In other detailed aspects of the invention, recombinant RSVs modified to express an immune modulatory molecule are employed as "vectors" for protective antigens of other pathogens, particularly respiratory tract pathogens such as parainfluenza virus (PIV). For example, recombinant RSV modified to express a cytokine may be engineered which incorporate sequences that encode protective antigens from PIV. The cloning of PIV cDNA and other disclosure supplemental to the instant invention is provided in United States Patent Application entitled PRODUCTION OF PARAINFLUENZA VIRUS VACCINES FROM CLONED NUCLEOTIDE SEQUENCES, filed May 22, 1998, Ser. No. 09/083,793 (corresponding to International Publication No. WO 98/53078) and its priority, provisional application filed May 23, 1997, Ser. No. 60/047,575, U.S. Provisional Patent Application entitled ATTENUATED HUMAN-BOVINE CHIMERIC PARAINFLUENZA VIRUS VACCINES, filed by Bailly et al. on Jul. 9, 1999 and identified by Appl. Ser. No. 60/143,134; and U.S. Patent Application entitled RECOMBINANT PARAINFLUENZA VIRUS VACCINES ATTENUATED BY DELETION OR ABLATION OF A NON-ESSENTIAL GENE, filed by Durbin et al. on Jul. 9, 1999 and identified by application Ser. No. 09/350,821; each incorporated herein by reference. This disclosure includes description of the following plasmids that may be employed to produce infectious PIV viral clones or to provide a source of PIV genes or genome segments for use within the invention: p3/7(131) (ATCC 97990); p3/7(131)2G (ATCC 97989); and p218(131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers.

According to this aspect of the invention, recombinant RSVs modified to express an immune modulatory molecule are provided which incorporate at least one PIV sequence, for example a polynucleotide containing sequences from either or both PIV1 and PIV2 or PIV1 and PIV3. Individual genes of RSV may be replaced with counterpart genes from human PIV, such as the F glycoprotein genes of PIV1, PIV2, or PIV3. Alternatively, a selected, heterologous genome segment, such as one encoding a cytoplasmic tail, transmembrane domain or ectodomain of an immunogenic protein may be substituted for a counterpart genome segment in, e.g., the same gene in RSV, within a different gene in RSV, or into a non-coding sequence of the RSV genome or antigenome. In one embodiment, a genome segment from an F gene of HPIV3 is substituted for a counterpart human RSV genome segment to yield constructs encoding chimeric proteins, e.g. fusion proteins having a cytoplasmic tail and/or transmembrane domain of RSV fused to an ectodomain of PIV to yield a novel attenuated virus, and/or a multivalent vaccine immunogenic against both PIV and RSV. Alternatively, one or more PIV3 gene(s) or genome segment(s) can be added to a partial or complete, chimeric or non-chimeric RSV genome or antigenome.

To construct chimeric RSV for use within the invention, heterologous genes may be added or substituted in whole or in part to the background genome or antigenome. In the case of chimeras generated by substitution, a selected gene or genome segment encoding a protein or protein region (e.g., a cytoplasmic tail, transmembrane domain or ectodomain, an epitopic site or region, a binding site or region, an active site or region containing an active site, etc.) from a human or bovine RSV is substituted for a counterpart gene or genome segment in the background RSV genome or antigenome to yield novel recombinants having desired phenotypic changes compared to one or both of the respective wild-type (or mutant parent) RSV strains. As used herein, "counterpart" genes or genome segments refer to counterpart polynucleotides from different RSV sources that encode homologous or equivalent proteins or protein domains, epitopes, or amino acid residues, or which represent homologous or equivalent cis-acting signals which may include but are not limited to species and allelic variants among different RSV subgroups or strains.

In other alternate embodiments, cytokine-expressing RSV are designed as vectors for carrying heterologous antigenic determinants incorporate one or more antigenic determinants of a non-RSV pathogen, such as a human parainfluenza virus (HPIV). In one exemplary embodiment, one or more HPIV1, HPIV2, or HPIV3 gene(s) or genome segment(s) encoding one or more HN and/or F glycoprotein(s) or antigenic domain(s), fragment(s) or epitope(s) thereof is/are added to or incorporated within the partial or complete HRSV vector genome or antigenome. In more detailed embodiments, a transcription unit comprising an open reading frame (ORF) of an HPIV1, HPIV2, or HPIV3 HN or F gene is added to or incorporated within the chimeric HRSV vector genome or antigenome.

Mutations incorporated within cDNAs, vectors and viral particles of the invention can be introduced individually or in combination into a RSV modified to express a cytokine or other immune modulator, and the phenotypes of rescued virus containing the introduced mutation(s) can be readily determined. In exemplary embodiments, amino acid changes displayed by attenuated, biologically-derived viruses versus a wild-type RSV, for example changes exhibited by cpRSV or tsRSV, are incorporated in combination within a recombinant RSV expressing a cytokine to yield a desired level of attenuation for vaccine use.

The present invention thus provides recombinant RSV modified to express a cytokine or other immune modulator, as well as novel vectors and viral particles which may incorporate multiple, phenotype-specific mutations introduced in selected combinations into the recombinant genome or antigenome to produce a suitably attenuated, infectious virus or subviral particle. This process, coupled with routine phenotypic evaluation, provides recombinant RSV having such desired characteristics as attenuation, temperature sensitivity, altered immunogenicity, cold-adaptation, small plaque size, host range restriction, etc. Mutations thus identified are compiled into a "menu" and introduced in various combinations to calibrate a vaccine virus to a selected level of attenuation, immunogenicity and stability.

In yet additional aspects of the invention, RSVs modified to express a cytokine or other immune modulator, with or without attenuating mutations, are constructed to have additional nucleotide modification(s) to yield a desired phenotypic, structural, or functional change. Typically, the selected nucleotide modification will specify a phenotypic change, for example a change in growth characteristics, attenuation, temperature-sensitivity, cold-adaptation, plaque size, host range restriction, or immunogenicity. Structural changes in this context include introduction or ablation of restriction sites into RSV encoding cDNAs for ease of manipulation and identification.

In preferred embodiments, nucleotide changes within the genome or antigenome of an RSV recombinant expressing a cytokine or other immune modulator include modification of a viral gene by partial or complete deletion of the gene, or reduction or ablation (knock-out) of its expression. Target genes for mutation in this context include genes encoding the attachment (G) protein, fusion (F) protein, small hydrophobic (SH), RNA binding protein (N), phosphoprotein (P), the large polymerase protein (L), transcription elongation factor (M2 ORF1 product), a transcription/translation regulatory protein (M2 ORF2) product, the matrix (M) protein, and two nonstructural proteins, NS1 and NS2. Each of these proteins can be selectively deleted, substituted or rearranged, in whole or in part, alone or in combination with other desired modifications, to achieve novel RSV recombinants.

In one aspect of the invention, an SH, NS1, NS2, or G gene or M2 ORF2 is modified in a recombinant virus that expresses a cytokine or other immune modulator. For example, each of these genes may be deleted in whole or in part or its expression reduced or ablated (e.g., by introduction of a stop codon or frame shift mutation or alteration of a transcriptional or translational start site) to alter the phenotype of the resultant recombinant clone to improve growth, attenuation, immunogenicity or other desired phenotypic characteristics. For example, deletion of the SH gene in the recombinant genome or antigenome will yield a vaccine candidate having novel phenotypic characteristics such as enhanced growth in vitro and/or attenuation in vivo. In a related aspect, an SH gene deletion, or deletion of another selected non-essential gene or genome segment such as a NS1 or NS2 gene, is constructed in virus modified to express an immune modulator, alone or in combination with one or more different mutations specifying an attenuated phenotype, e.g., a point mutation adopted directly (or in modified form, e.g., by introducing multiple nucleotide changes in a codon specifying the mutation) from a biologically derived attenuated RSV mutant. For example, the SH, NS1, NS2 or M2-2 gene may be deleted in combination with one or more cp and/or ts mutations adopted from cpts248/404, cpts530/1009, cpts530/1030 or another selected mutant RSV strain, to yield a recombinant RSV exhibiting increased yield of virus, enhanced attenuation, improved immunogenicity and genetic resistance to reversion from an attenuated phenotype due to the combined effects of the different mutations.

Alternative nucleotide modifications in recombinant RSVs of the invention can include a deletion, insertion, addition or rearrangement of a cis-acting regulatory sequence for a selected gene in the recombinant genome or antigenome. In one example, a cis-acting regulatory sequence of one RSV gene is changed to correspond to a heterologous regulatory sequence, which may be a counterpart cis-acting regulatory sequence of the same gene in a different RSV or a cis-acting regulatory sequence of a different RSV gene. For example, a gene end signal may be modified by conversion or substitution to a gene end signal of a different gene in the same RSV strain. In other embodiments, the nucleotide modification may comprise an insertion, deletion, substitution, or rearrangement of a translational start site within the recombinant genome or antigenome, e.g., to ablate an alternative translational start site for a selected form of a protein. In one example, the translational start site for a secreted form of the RSV G protein is ablated to modify expression of this form of the G protein and thereby produce desired in vivo effects. In other embodiments, mutations identified by empirical analysis of minireplicons or infectious virus can be incorporated (see, e.g. Kuo et al., *J. Virol.* 71:4944-4953, 1997; Whitehead et al., *J. Virol.* 73:3438-3442, 1999; incorporated herein by reference).

In related aspects of the invention, compositions (e.g., isolated polynucleotides and vectors incorporating an RSV-encoding cDNA) and methods are provided for producing an isolated infectious recombinant RSV expressing a cytokine or other immune modulator. Included within these aspects of the invention are novel, isolated polynucleotide molecules and vectors incorporating such molecules that comprise a RSV genome or antigenome which is modified to encode the immune modulator. Also provided is the same or different expression vector comprising one or more isolated polynucleotide molecules encoding N, P, L and RNA polymerase elongation factor proteins. These proteins also can be expressed directly from the genome or antigenome cDNA. The vector(s) is/are preferably expressed or coexpressed in a cell or cell-free lysate, thereby producing an infectious RSV particle or subviral particle.

The above methods and compositions for producing RSV modified to express a cytokine or other immune modulator yield infectious viral or subviral particles, or derivatives thereof. An infectious virus is comparable to the authentic RSV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, L and M2(ORF1) proteins is an example of a subviral particle which can initiate an infection if introduced into the cytoplasm of cells. Subviral particles provided within the invention include viral particles which lack one or more protein(s), protein segment(s), or other viral component(s), and are typically infectious.

In other embodiments the invention provides a cell or cell-free lysate containing an expression vector which comprises an isolated polynucleotide molecule encoding an RSV genome or antigenome modified to encode an immune modulator as described above, and an expression vector (the same or different vector) which comprises one or more isolated polynucleotide molecules encoding the N, P, L and RNA polymerase elongation factor proteins of RSV. One or more of these proteins also can be expressed from the genome or antigenome cDNA. Upon expression the genome or antigenome and N, P, L, and RNA polymerase elongation factor proteins combine to produce an infectious RSV viral or subviral particle.

The recombinant RSVs of the invention are useful in various compositions to generate a desired immune response against RSV in a host susceptible to RSV infection. Attenuated RSVs of the invention are capable of eliciting a protective immune response in an infected human host, yet are sufficiently attenuated so as to not cause unacceptable symptoms of severe respiratory disease in the immunized host. The attenuated virus or subviral particle may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated RSV particle or subviral particle modified to express a cytokine. In preferred embodiments, the vaccine is comprised of a mutant RSV having a genome or antigenome modified to encode a cytokine and having at least one, and preferably two or more attenuating mutations or other nucleotide modifications as described above to achieve a suitable balance of attenuation and immunogenicity. The vaccine can be formulated in a dose of $10^3$ to $10^6$ PFU or more of attenuated virus. The vaccine virus may elicit an immune response against a single RSV strain or antigenic subgroup, e.g. A or B, or against multiple RSV strains or subgroups. In this regard, recombinant RSV of the invention can be combined in vaccine formulations with other RSV vaccine strains or subgroups having different immunogenic characteristics for more effective protection against one or multiple RSV strains or subgroups.

In related aspects, the invention provides a method for stimulating the immune system of an individual to elicit an immune response against RSV in a mammalian subject. The method comprises administering a formulation of an immunologically sufficient amount of an attenuated RSV modified to express a cytokine or other immune modulator, in a physiologically acceptable carrier and/or adjuvant. In one embodiment, the immunogenic composition is a vaccine comprised of an isolated RSV particle or subviral particle modified to express a cytokine and having at least one, and preferably two or more attenuating mutations or other nucleotide modifications specifying a desired phenotype as described above. The vaccine can be formulated in a dose of $10^3$ to $10^6$ PFU or more of attenuated virus. The vaccine may elicit an immune response against a single RSV strain or antigenic subgroup, e.g. A or B, or against multiple RSV strains or subgroups. RSV recombinants of the invention can be combined with RSV having different immunogenic characteristics in a vaccine mixture, or administered separately in a coordinated treatment protocol, to elicit more effective protection against one RSV strain, or against multiple RSV strains or subgroups. Preferably the immunogenic composition is administered to the upper respiratory tract, e.g., by spray, droplet or aerosol. Often, the composition will be administered to an individual seronegative for antibodies to RSV or possessing transplacentally acquired maternal antibodies to RSV.

```
CCCGGGATGGGGAAATAATG;        (SEQ ID NO. 5)

TGAAGTTATTAAAAATTCCCGGG;     (SEQ ID NO. 6)

AGGCCCCGGGGCCT.              (SEQ ID NO. 7)
```

Figure 2:
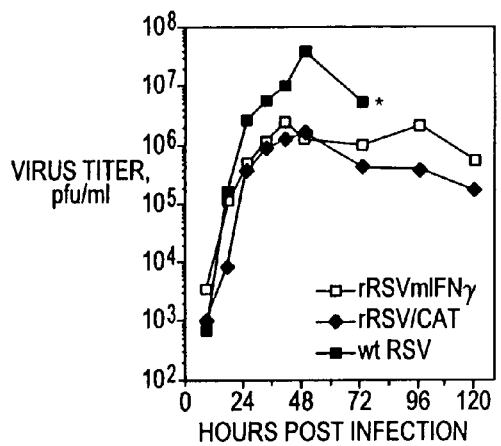

FIG. 2 details growth kinetics for rRSV/mIFNγ, rRSV/CAT (incorporating a chloramphenical acetyl transferase gene) and wt RSV in HEp-2 cells. Cell monolayers were infected with 2 PFU per cell (two replicate wells per virus), and 200 µl aliquots of supernatant were taken at the indicated time, adjusted to contain 100 mM magnesium sulfate and 50 mM HEPES buffer (pH 7.5), flash-frozen and stored at −70° C. until titration. Each aliquot taken was replaced with an equal amount of fresh medium. Each single-step growth curve represents the average of the virus titers from the two infected cell monolayers. The cell monolayer infected with wt RSV was more than 90% destroyed at 72 hours post-infection (*), whereas that infected with rRSV/mIFNγ or rRSV/CAT was almost intact, reflecting attenuation of the chimeric virus in vitro.

Figure 3:
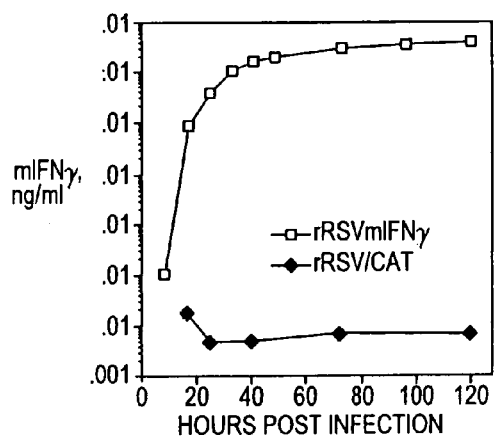

FIG. 3 demonstrates kinetics of accumulation of mIFNγ in culture fluids of HEp-2 cells infected with rRSV/mIFNγ or rRSV/CAT. Cell monolayers were infected with 2 PFU per cell (two replicate wells per virus), samples were taken at the indicated time points, and the mIFNγ content was determined in each sample by ELISA using the Quantikine M Mouse IFNγ Immunoassay (R&D systems, MN).

Figure 4:
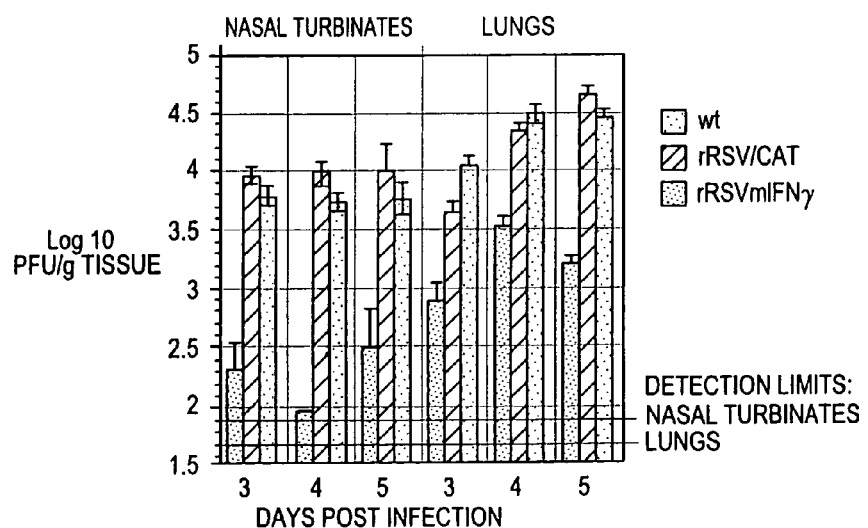

FIG. 4 demonstrates kinetics of virus replication in the upper and lower respiratory tract of BALB/c mice inoculated intranasally with $10^6$ PFU of rRSV/mIFNγ, rRSV/CAT, or wt RSV. Five mice from each group were sacrificed on the indicated day, the nasal turbinates and lung tissues were removed and homogenized, and the concentration of infectious virus was determined by plaque assay of individual tissue specimens. Mean $log_{10}$ titer per gram tissue with standard deviation is shown. The limit of virus detection in the upper and lower respiratory tract is indicated.

Figure 5:
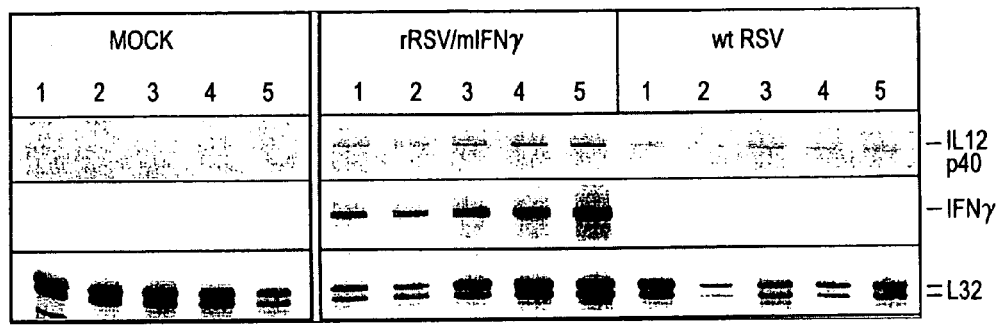

FIG. 5 shows detection of pulmonary mIFNγ, IL-12 p40, and L-32 (housekeeping gene) mRNAs by ribonuclease protection assay. Mice (five animals per group) were inoculated intranasally with medium alone (mock) or $10^6$ PFU per animal of rRSV/mIFNγ or wt RSV, and on day 4 after immunization the lungs were harvested and total RNA was purified. RNA was hybridized with radioactive RNA probes synthesized using mCK-2B template set (PharMingen RiboQuant Multi-Probe RNAse Protection Assay System), treated with ribonuclease A, purified, and electrophoresed in a 5% denaturing acrylamide gel. Autoradiographs are shown for the region of the gel containing protected species corresponding to the indicated mRNAs. Different exposure times were used for each of the three mRNAs. Normal mouse RNA and yeast were used as additional negative controls.

FIG. 6 demonstrates levels of cytokine mRNAs in the lungs of mice following primary infection with rRSV/mIFNγ or wt RSV and following challenge with wt RSV. Mice were immunized intranasally with $10^6$ PFU per animal of rRSV/mIFNγ, wt RSV or medium alone. On day 1 or 4 after immunization 5 animals from each group were sacrificed and pulmonary RNA was isolated. Additional immunized animals were challenged on day 28 with $10^6$ PFU of wt RSV, and total lung RNA was isolated individually from 5 animals from each group on day 29 or 32. The accumulation of mRNA for selected cytokines was measured by the ribonuclease protection assay described in the legend to FIG. 5 (PharMingen, Calif., template sets mCK-1 and mCK-2B). Radioactivity for each mRNA was quantified by phosphorimager analysis, backgrounds were subtracted, and each value was calculated as a percentage of radioactivity relative to the L-32 housekeeping gene mRNA and displayed as an average of five animals with the standard deviation. Samples which lacked detectable mRNA for the indicated cytokine are marked with asterisks.

Figure 10:
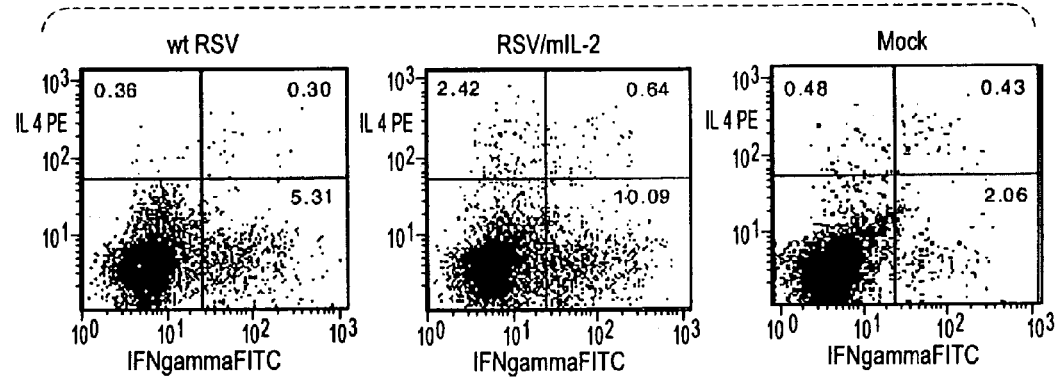
Figure 7:
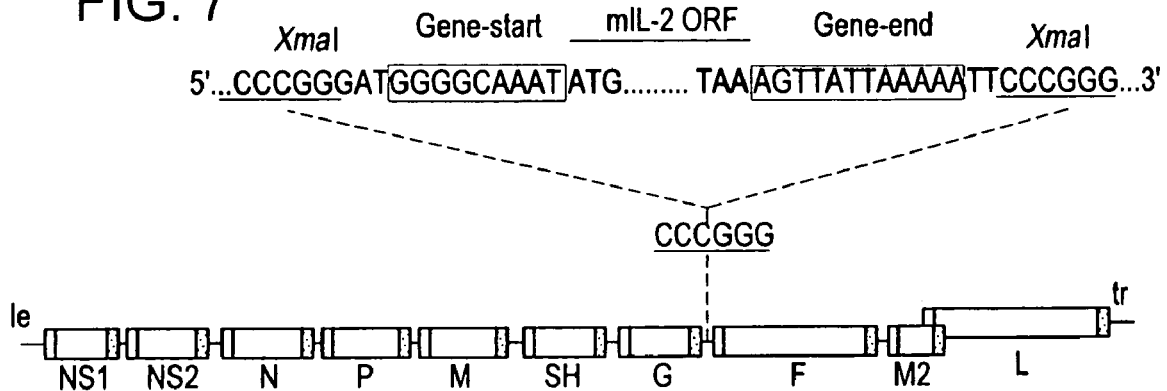
Figure 8:
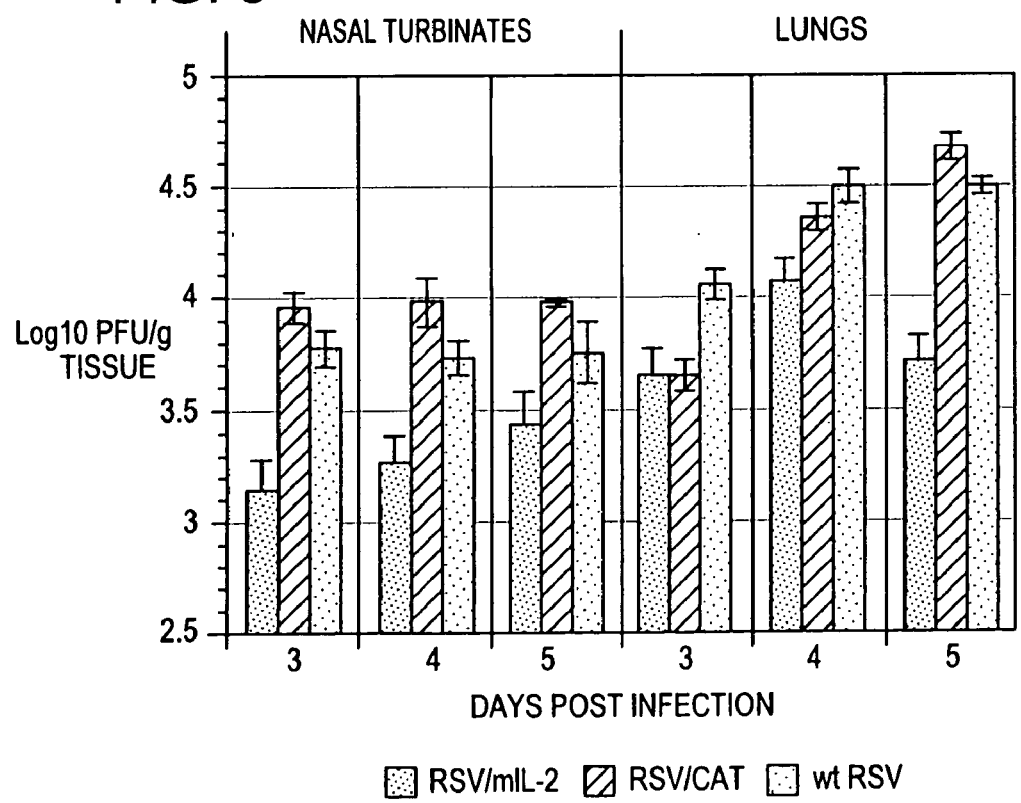

FIG. 7 illustrates a map of the genome of rRSV/mIL-2. A cDNA of the mIL-2 ORF, whose translational stop and start codons are in bold, was modified by PCR to be flanked by RSV-specific gene-start and gene-end transcription signals (boxed) and XmaI sites (underlined). The resulting mIL-2 transcription cassette was inserted into the intergenic region between the G and F genes using an XmaI site which had been placed there previously (Bukreyev et al., *J. Virol.* 70:6634-6641, 1996; incorporated herein by reference).

```
CCCGGGATGGGGCAAATATG;        (SEQ ID NO. 9)
TAAAGTTATTAAAAATTCCCGGG.     (SEQ ID NO. 10)
```

FIG. 8 details replication of rRSV/mIL-2, rRSV/CAT and wt rRSV in upper (nasal turbinates) and lower (lungs) respiratory tract of BALB/c mice. Animals were each infected intranasally with $10^6$ PFU of the indicated virus. 5 animals per group were sacrificed on the indicated days, the nasal turbinates and lungs were harvested, and viral titers were determined by plaque assay. The data represent average concentrations of the virus ($\log_{10}$ PFU/g tissue) with SD. Statistical significance of the reduced titer of rRSV/mIL-2 compared to wt rRSV by Student's t test: nasal turbinates, day 3, $P<0.01$; day 4, $P<0.02$; day 5, $P<0.1$; lungs, day 3, $P<0.05$; day 4, $P<0.05$; day 5, $P<0.001$.

FIG. 9 shows accumulation of pulmonary mRNA for IL-2, IFNγ, IL-4, IL-5, IL-6, IL-10, IL-13 and IL-12 p40 in mice which were infected with $10^6$ PFU per animal of rRSV/mIL-2 or wt rRSV, or which received medium alone (mock). 4 or 5 mice per group were sacrificed on days 1 and 4 and total pulmonary RNA was isolated and analyzed by an RNAse protection assay as described previously (Bukreyev et al. *Proc. Natl. Acad. Sci. USA* 96:2367-2372, 1999) using the RiboQuant Multi-Probe RNAse Protection Assay System (PharMingen) and two different probe template sets, namely mCK-1 and mCK-2B. Each mouse was analyzed separately, and each protected species detected by polyacrylamide gel electrophoresis was quantitated by phosphorimagery and calculated as a percentage of the amount of L-32 housekeeping gene mRNA in the same sample. Mean values of each group per day with SD are shown. Note that each y axis has a different scale.

FIG. 10 provides dot plots showing flow cytometric analysis of the CD4+ lymphocytes expressing IL-4 (IL4 PE) or IFNγ (IFN gamma FITC). Mice were infected with $10^6$ PFU of wt rRSV (left panel) or rRSV/mIL-2 (middle panel), or were mock-infected (right panel). The animals were sacrificed 10 days later and pulmonary CD4+ cells were harvested and analyzed by flow cytometry. The percentage of CD4+ cells in three quadrants is shown for each plot. Each plot represents cells from an individual mouse.

Figure 11:

FIG. 11 provides a map of the genome of rRSV/mGMCSF. A cDNA of the mGM-CSF ORF, whose translational stop and start codons are in bold, was modified by restriction fragment replacement as described in the text to be flanked by RSV-specific gene-start and gene-end transcription signals (boxed) and XmaI sites (underlined). The resulting mIL-2 transcription cassette was inserted into the intergenic region between the G and F genes using an XmaI site which had been placed there previously (Bukreyev et al., *J. Virol.* 70:6634-6641, 1996; incorporated herein by reference).

```
AGTTACTTAAAAACATATTATCACAAAAGGCCCC    (SEQ ID NO. 8)
GGGGCCTTGACCAAACTTAAACAGAATCAAAATA
AACTCTGGGGCAAAT;

CCCGGGATGGGGCAAATATG;                 (SEQ ID NO. 9)

TAAAGTTATTAAAAATTCCCGGG.              (SEQ ID NO. 10)
```

Figure 12:
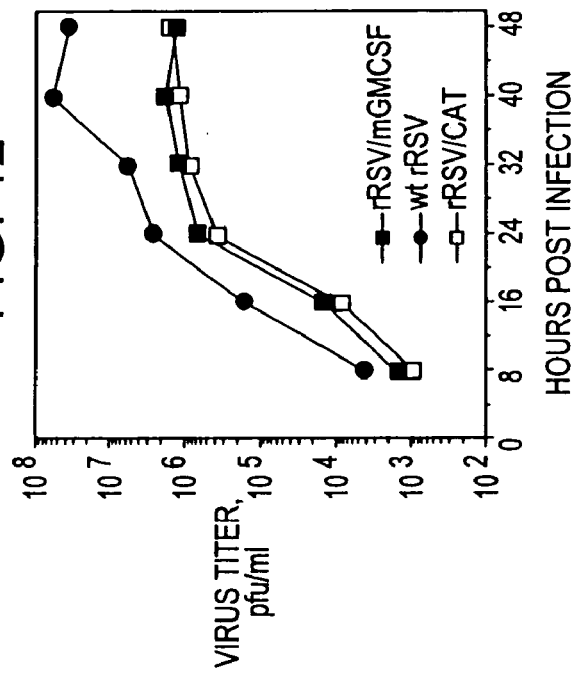

FIG. 12 illustrates growth kinetics of rRSV/mGMCSF, rRSV/CAT and wt rRSV in HEp-2 cells. Cell monolayers were infected with 2 PFU per cell (two replicate wells per virus), and 200 µl aliquots of medium were taken and replaced at the indicated times. These samples were flash-frozen and the titer of infectious virus was determined later by plaque assay. The average of the two monolayers is shown for each time point.

DESCRIPTION OF THE SPECIFIC EMBODIMENTS

The present invention provides isolated infectious recombinant RSV (rRSV) that are engineered to express one or more immune modulatory molecule(s) to improve the usefulness of recombinant RSV vaccine candidates for the treatment or prevention of RSV infection. The recombinant virus has a modified genome or antigenome incorporating a polynucleotide sequence that encodes one or more immune modulatory molecule(s).

Various cytokines and other immune modulatory molecules can be incorporated in a recombinant RSV of the invention in such a manner that they are expressed by the virus in infected cells and modify one or more aspects of viral biology, e.g., infectivity, replication, pathogenicity, and/or alter one or more host immune responses, for example an anti-RSV neutralizing antibody response, a T-helper cell response, a cytotoxic T cell (CTL) response, and/or a natural killer (NK) cell response. The immune modulatory molecule may be a cytokine or, alternatively any other immune modulatory factor such as chemokines, chemokine or cytokine anatagonists, enzymes (e.g., nitric oxide), surface or soluble receptors, adhesion molecules, and ligands. When incorporated and expressed by recombinant viruses of the invention, the cytokine, or its encoding polynucleotide, acts to alter, i.e., to increase, decrease, or otherwise enhance, aspects of viral biology and/or host immune responses to RSV.

In basic aspects of the invention, the disclosure herein provides for the intracellular coexpression from recombinant RSV of any of a wide variety of immune modulatory proteins as found in nature or engineered by recombinant DNA technology. These modulators typically affect hematopoietic cells or, alternatively, can block signals and interactions between hematopoietic cells and their environment, including infecting viruses. A remarkably wide array of molecules is amenable to expression in this fashion. Among the many examples are proteins which act as soluble messengers, or antagonize or sequester soluble messengers, or otherwise interact with cells of the immune system. Exemplary molecules include the various members of the cytokine/chemokine group, including the interleukins, the interferons, the various subfamilies of chemokines, the various colony stimulating factors (CSFs), certain molecules such as Flt3 ligand, and other factors which modulate hematopoietic cells. A detailed listing of exemplary cytokines and chemokines that are useful within the invention can be found in the following review volumes: The Cytokine Handbook, A. Thomson (ed.). Academic Press, San Diego, 1998; and Cytokines, A. Mire-Sluis and R. Thorpe (eds.) Academic Press, San Diego, 1998, incorporated herein by reference.

For use within the invention, suitable cytokines and chemokines include, but are not limited to, interleukins, including IL-1 alpha and beta, and IL-2, 3, 4, 5, 6, 7, 8, 9, 10, 11, 12, 13, 14, 15, 16, 17, and 18. Also included are interferon gamma (IFNγ) and other interferons, including interferon alpha, beta and omega. Other molecules for use within recombinant viruses of the invention include tumor necrosis factor (TNF) and its related ligands and receptors, including Fas ligand (CD95), CD40 ligand, and the recently-reported B cell-stimulatory BlyS protein (Moore et al. *Science* 285:260-263, 1999). Other molecules include Flt3 ligand. In this context it is noted that ligands such as Flt3 or CD40 ligand would be expressed on the surface of infected cells and can change or enhance immune recognition of infected cells. Ligands such as Flt3 can be engineered to be incorporated in the envelope of recombinant RSV particles, which can change the tropism of the virus, targeting it in this case to dendritic cells.

Yet additional immune modulatory molecules for introduction into recombinant RSV of the invention include colony stimulating factors (CSFs) such as granulocyte macrophage colony stimulating factor (GM-CSF) and stem cell factor. Exemplary chemokines include the CXC group, which includes IL-8, monokine induced by INF-gamma (Mig), cytokine responsive gene 2 (Crg-2) (Mahalingam et al., *J. Virol.* 73:1479-1491, 1999), platelet factor-4 (PF-4), neutrophil activating protein-2 (NAP-2), melanoma growth-stimulatory activity (GRO) alpha, beta and gamma, epithelial cell-derived neutrophil attractant-78 (ENA-78), granulocyte chemotactic protein-2 (GCP-2), IFN-gamma-inducible protein-10 (IP-10), stromal cell-derived factor 1 (SDF-1) alpha and beta. A second group of chemokines, the C chemokines, includes lymphotactin. The third currently-recognized group, the CC chemokines, includes eotaxin, monocyte chemotactic proteins (MCP) 1, 2, 3, 4 and 5, RANTES (regulated on activation, normal T-cell expressed and secreted), macrophage inflammatory protein (MIP) 1 alpha and beta, and thymus and activation-regulated chemokine (TARC).

Other useful immune modulatory molecules include cytokine antagonists, such as the naturally-occurring secreted IL-1 receptor antagonist (Arend, *Ad. Immunol.* 54:167-227, 1993, incorporated herein by reference), which binds to the receptor thereby blocking it without activation. Another illustrative example is a genetically-engineered fusion protein made between the extracellular domain of the receptor for tumor necrosis factor (TNF) and the constant domains of IgG, which can bind and sequester soluble TNF (Fisher et al., *N. Eng. J. Med.* 334:1697-1702, 1996). A third example is a recombinant IL-1 receptor which sequesters IL-1 (Takebe et al., *J. Interferon Cytokine Res.* 18:321-326, 1998, incorporated herein by reference). Other cytokine/chemokine antagonists amenable to expression in rRSV include, for example, peptides derived from the complete molecule, exemplified for IL-1 (Palaszynski, *Biochem. Biophys. Res. Commun.* 147:24-209, 1987, incorporated herein by reference), or inactive forms generated by site-directed mutagenesis of residues critical for function, exemplified for TNF (von Feldt et al., *Immunol. Res.* 13:96-109, 1994, incorporated herein by reference). Other molecules include various virus-derived homologs and modulators. Thus, a large array of polypeptide immune modulators exist which can be readily inserted for expression into recombinant RSV by this invention and directly evaluated for effects on immunogenicity, efficacy, and disease in rodent or primate animal models and in the clinic.

To construct recombinant RSV engineered to express an immune modulator(s), a viral genome or antigenome is modified to incorporate a polynucleotide sequence encoding the cytokine or other immune modulator molecule(s), which are added, typically as a separate gene with its own gene start (GS) and gene end (GE) signals. Generally, the polynucleotide sequence encoding the immune modulator is added or substituted into an intergenic or other non-coding region of the recombinant RSV genome or antigenome, at any suitable locus so as not to disrupt an open reading frame within the genome or antigenome. Typically, a polynucleotide sequence encoding the modulator is introduced within the recombinant genome or antigenome as a supernumerary sequence, although non-coding elements within the genome or antigenome may be removed and the cytokine-encoding polynucleotide substituted at the location of the deletion.

Construction of recombinant RSV of the invention which are modified to express a cytokine or other immune modulator typically involves addition or substitution of the cytokine-encoding polynucleotide at a selected position within the genome or antigenome. The level of expression of the cytokine or other immune modulator can be adjusted by altering the gene order position of the cytokine-encoding polynucleotide within the recombinant genome or antigenome. For example, the cytokine-encoding polynucleotide can be introduced at any intergenic position or non-coding region within any of the RSV genes. Introduction of the cytokine-encoding polynucleotide may be selected at a position that is more promoter-proximal or promotor-distal relative to any of these genes or ORFs to enhance or reduce, respectively, expression of the cytokine or other immune modulator.

As used herein, "RSV gene" generally refers to a portion of the RSV genome encoding an mRNA and typically begins at the upstream end with the 10-nucleotide gene-start (GS) signal and ends at the downstream end with the 12 to 13-nucleotide gene-end (GE) signal. Ten such genes for use within the invention are known for RSV, namely NS1, NS2, N, P, M, SH, G, F, M2 and L. The term "gene" is also used herein to refer to a "translational open reading frame" (ORF). ORF is more specifically defined as a translational open reading frame encoding a significant RSV protein, of which 11 are currently recognized: NS1, NS2, N, P, M, SH, G, F, M2-1 (alternatively, M2(ORF1)), M2-2 (alternatively, M2(ORF2)), and L. Thus, the term "gene" interchangeably refers to a genomic RNA sequence that encodes a subgenomic RNA, and to a ORF (the latter term applies particularly in a situation such as in the case of the RSV M2 gene, where a single mRNA contains two overlapping ORFs that encode distinct proteins). Collins et al., *J. Gen. Virol.* 71:3015-3020, 1990; Bermingham and Collins, *Proc. Natl. Acad. Sci. USA* 96:11259-11264, 1999; Ahmadian et al., *EMBO J.* 19:2681-2689, 2000; Jin et al., *J. Virol.* 74:74-82, 2000 (each incorporated herein by reference). When the term "gene" is used in the context of determining gene position relative to a promoter position, the term ordinarily refers strictly to an mRNA-encoding sequence bordered by transcription gene-start and gene-end signal motifs (Collins et al., *Proc. Natl. Acad. Sci. USA* 83:4594-4598, 1986; Kuo et al., *J. Virol.* 70:6892-6901, 1996; each incorporated herein by reference).

By "genome segment" is meant any length of continuous nucleotides from the RSV genome, which may be part of an ORF, a gene, or an extragenic region, or a combination thereof.

One alternative method for inserting a foreign gene, including a gene encoding a cytokine, into RSV is to place the cDNA under the control of RSV gene-start and gene-end signals as described above, but to insert the cDNA so that the gene is expressed from the antigenome rather than from the genome. Preferably, the foreign gene is placed immediately downstream from the promoter at the 3' end of the antigenome, such that this promoter-proximal location ensures a high level of expression. This strategy was described for rabies virus, in which the foreign chloramphenicol acetyl transferase gene was placed in the antigenome strand and, furthermore, the antigenome promoter was replaced by that of the genome (Finke and Conzelmann, *J. Virol.* 71:7281-7288, 1997, incorporated herein by reference). However, for RSV the antigenomic promoter can direct efficient transcription, and so it is generally not necessary to replace the antigenome promoter. Indeed, we have constructed minireplicons in which a foreign gene was expressed from the antigenome.

Yet another method for expression of a foreign gene is to place the ORF under the control of a mammalian internal ribosome entry site, and to insert this ORF into the downstream noncoding region of any one or more of the RSV genes. This strategy was described previously for influenza virus (Garcia-Sastre et al., *J. Virol.* 68:6254-6261, 1994, incorporated herein by reference). This results in the expression of an mRNA in which the authentic viral ORF is undisturbed at the 5' end of the mRNA, but the downstream noncoding region contains the foreign ORF which is expressed by internal ribosome entry. Alternatively, the downstream ORF could be positioned so that it can be accessed by ribosomal stop-restart (Horvath et al., *EMBO J.* 9:2639-2647, 1990, incorporated herein by reference).

Yet another method for expression is by the construction of chimeric or fusion proteins. For example, a protein ectodomain which is desired to be expressed at the surface of the infected cell and virion is attached to the downstream end of the SH ORF such that the reading frame is undisturbed and a chimeric protein results. In this configuration, the SH moiety provides the signal and membrane anchor, and the C-terminal attached domain is displayed extracellularly. This strategy takes advantage of the finding that the SH protein does not appear to be an important antigen in immunoprophylaxis and is not required for efficient replication in vitro or in vivo. This strategy is preferred particularly in situations where a ligand such as Flt3 ligand is to be expressed at the virion surface for the purpose of targeting virus to cells which express Flt3, namely dendritic cells. However, other viral genes can be used to construct chimeric proteins. For example, the G protein has been shown to readily accept deletions and insertions at the C-terminal end, and thus could accommodate a foreign polypeptide moiety. Furthermore, any of the RSV genes can be inserted as a second copy, whereby inactivation of protein function in the course of making the chimeric protein would be tolerated.

In alternative embodiments of the invention, the recombinant virus is modified to encode more than one immune modulator, for example multiple cytokines or a cytokine and a chemokine, to provide more desirable phenotypic characteristics. In yet additional aspects, more than one RSV is engineered to each express a different cytokine, e.g., a cytokine that enhances CTL response in the host and another cytokine that enhances NK cell responses, and these different viruses may be administered simultaneously or in a coordinated treatment protocol to enhance vaccine effectiveness.

RSV is generally characterized as an enveloped nonsegmented negative strand RNA virus of the paramyxovirus family (Collins, et al., *Fields Virology* 2:1313-1352, 1996, incorporated herein by reference). Its genome, which is 15,222 nucleotides (nt) in length for the well known strain A2, is transcribed into 10 messenger RNAs that were previously shown to encode 10 proteins (Collins, et al., *Fields Virology* 2:1313-1352, 1996; Atria, et al., *J. Virol.* 72:1452-1461, 1998; Bukreyev, et al., *J. Virol.* 71:8973-8982, 1997; Collins, et al., *Porch. Natl. Acad. SCI. USA* 93:81-85, 1996; Ten and Collins, *J. Virol.* 72:5707-5716, 1998; Ten and Collins, *J. Virol.* 73:466-473, 1999; Whitehead, et al., *J. Virol.* 73:3438-3442, 1999, each incorporated herein by reference).

Four of the RSV proteins presently identified are nucleocapsid/polymerase proteins, namely the major nucleocapsid N protein, the phosphoprotein P, and polymerase protein L, and the transcription antitermination protein M2-1 encoded by a first open reading frame (ORF) in the M2 gene. Three of these are surface glycoproteins, namely the attachment G protein, the fusion F glycoprotein responsible for penetration and syncytium formation, and the small hydrophobic SH protein of unknown function. The matrix M protein is an internal virion protein involved in virion formation. There are two nonstructural proteins NS1 and NS2 of unknown function. The G and F proteins are the major neutralization and protective antigens (Collins, et al., *Fields Virology* 2:1313-1352, 1996; Connors, et al., *J. Virol.* 66:1277-1281, 1992). Resistance to reinfection by RSV is largely mediated by serum and mucosal antibodies specific against these proteins. RSV-specific cytotoxic T cells are also induced by RSV infection and can be directed against a number of different proteins, but this effector has not yet been shown to be an important contributor to long term resistance to reinfection. However, both CD8+ and CD4+ cells can be important in regulating the immune response, and both may be involved in viral pathogenesis (Johnson, et al., *J. Virol.* 72:2871-2880, 1998; Srikiatkhachorn and Braciale, *J. Exp. Med.* 186:421-432, 1997). Thus, F and G are the most important antigenic determinants, but other proteins can also play important roles in the immune response.

Finally, there is a second ORF in the M2 mRNA which encodes an RNA regulatory factor M2-2. The M2-2 mRNA, not found in other paramyxoviruses or rhabdoviruses, contains two overlapping translational open reading frames (ORFs) which each express a protein (FIG. 1A) (Collins et al., *J. Gen. Virol.* 71:3015-20, 1990, incorporated herein by reference). The upstream ORF1 encodes the 194-amino acid M2-1 protein, which is a structural component of the virion (Peeples et al., *Virology* 95:137-45, 1979, incorporated herein by reference) and is an anti-termination factor that promotes transcriptional chain elongation and also increases the frequency of readthrough at gene junctions (Collins et al., *Proc. Nat. Acad. Sci. USA* 93:81-5, 1996; Fearns and Collins, *J. Virol.* 73:5852-5864, 1999; Collins et al. *Virology* 259:251-255, 1999; Hardy et al., *J. Virol.* 72:520-6, 1998, each incorporated herein by reference). ORF2 of strain A2 has 3 potential start site at codons 1, 3 and 7, all of which overlap with ORF1 (FIG. 1A). Initiation at the first of these would give an M2-2 protein of 90 amino acids. M2 ORF2 is present in all pneumoviruses examined to date (Collins et al., *J. Gen. Virol.* 71:3015-20, 1990; Ling et al., *J. Gen. Virol.* 73:1709-15, 1992; Zamora et al., *J. Gen. Virol.* 73:737-41, 1992, each incorporated herein by reference). Translation of M2 mRNA in a cell-free system yielded the M2-1 protein and a second, 11 kDa protein which was of the appropriate size to be the M2-2 protein (Collins et al., *J. Gen. Virol.* 71:3015-20, 1990). Coexpression of M2-2 in a model minireplicon system was found to have a very potent down-regulatory effect on RNA synthesis (Collins et al., *Proc. Nat. Acad. Sci. USA* 93:81-5, 1996; Hardy et al., *J. Virol.* 72:520-6, 1998). More recently, the RSV M2-2 protein was detected as a minor species in RSV-infected cells. Thus, several lines of evidence indicate that the M2-2 ORF is an eleventh RSV gene. However, definitive evidence that an ORF encodes a significant viral protein includes identification of a biological effect mediated by expression of the ORF in an infectious virus. This is demonstrated for M2-2 according to the methods of the present invention by ablating or deleting all or part of the M2-2 ORF and thereafter identifying phenotypic changes—including a shift in the balance of RNA transcription and replication. Although previous studies suggested that the M2-2 protein generally down-regulates transcription and RNA replication, it is now known that that M2-2 unexpectedly shifts the balance of RNA synthesis from transcription to replication (see, U.S. Patent Application entitled PRODUCTION OF ATTENUATED RESPIRATORY SYNCYTIAL VIRUS VACCINES INVOLVING MODIFICATION OF M2 ORF2, filed by Collins et al. on Jul. 9, 2000 and identified by, and priority U.S. Provisional Application No. 60/143,097; Bermingham et al., *Proc. Natl. Acad. Sci. USA* 96:11259-11264, 1999; and Jin et al., *J. Virol.* 74:74-82, 2000, each incorporated herein by reference).

Accordingly, within yet another aspect of the instant invention expression of M2 ORF2 is reduced or ablated within a recombinant RSV modified to express an immune modulatory molecule. Modifications that delete M2 ORF2, in whole or in part, or reduce or ablate expression of M2 ORF2 specify a range of desired phenotypic changes in the resulting virus or subviral particle. In preferred embodiments, M2 ORF2 deletion and knock out mutants exhibit attenuated viral growth compared to growth of a corresponding wild-type or mutant parental RSV strain. Growth, for example in cell cultures, may be reduced by about two-fold, more often about 5-fold, and preferably about 10-fold or greater overall (e.g., as measured after a 7-8 day period in culture) compared to growth of the corresponding wild-type or mutant parental RSV strain. In more detailed aspects, recombinant RSV of the invention exhibit delayed kinetics of viral growth, wherein growth during an initial 2-5 day period is reduced by about 100-fold and up to 1,000-fold or more compared to kinetics of growth in the corresponding wild-type or mutant parental RSV strain. These desirable effects are specified by reduction or ablation of M2-2 ORF2 expression. Intermediate effects are achieved by reduction of M2-2 protein synthesis. Furthermore, as M2-2 is a regulatory protein, alterations in virus growth and the pattern of gene expression can also be achieved by increasing rather than decreasing M2-ORF2 expression. As described above, this can be readily achieved by expressing M2-ORF2 as a separate gene and, if necessary, moving the gene to a more promoter-proximal or promoter-distal location.

Expression of M2 ORF2 is preferably reduced or ablated by modifying the recombinant RSV genome or antigenome to incorporate a frame shift mutation or one or more stop codons in M2 ORF2. In more detailed aspects of the invention, M2 ORF2 is subjected to mutagenesis to generate a specific frame-shift mutation, referred to in the above-incorporated disclosures as the NdeI mutation. The restriction enzyme site within ORF2 for the NdeI mutation was identified at genome position 8299, and the frame-shift mutation (2 nts added) was at codon 47 of the predicted 90 amino acid protein. Accordingly, the NdeI mutant (exemplified by recombinant strain rA2-NdeI) encodes the N-terminal 46 amino acids of M2-2 fused to 18 heterologous amino acids encoded by the frameshift. Optional frame shift mutations to generate M2 ORF2 knock out mutants are readily identified.

In other more detailed aspects of the invention, a second exemplary M2-2 knock-out mutation, the K5 mutation, is incorporated into a cytokine-expressing RSV, which ablates expression of M2 ORF2 by altering three potential initiation codons within M2 ORF2 to ACG stop codons. A stop codon may also be added in each register following the ORF1 termination codon, terminating M2 ORF2 at codon 13 to minimize the possibility of reversion or non-AUG initiation. An exemplary M2 ORF2 knock out mutant in this context is the recombinant strain rA2-K5 (also referred to as rA2ΔM2-2), described in more detail in the above-incorporated disclosures. Other alterations to achieve disruption of M2 ORF2 expression or M2-2 protein expression or function to generate attenuated RSV vaccine candidates include partial or complete deletion of the M2 ORF2 coding sequence, in whole or in part, to render the M2-2 protein partially or entirely nonfunctional or terminate its expression. Yet another method for changing the level of expression of M2-ORF2 is to alter its translational start site or its spacing relative to the upstream ORF1. For example, M2-ORF2 can be expressed as a separate gene at any locus in the genome or antigenome, e.g., by insertion of the M2-ORF2 with its own gene start and gene end signals into an intergenic or other non-coding region of the genome or antigenome. These exemplary manipulations involving M2-ORF2 can be implemented to alter or ablate expression of other RSV genes within the recombinant vaccine candidates of the invention.

As noted above, the recombinant RSV of the invention recombinant RSV engineered to express an immune modulator(s) possess highly desirable phenotypic characteristics for vaccine development. In exemplary embodiments, alteration of the recombinant genome or antigenome to express a cytokine, for example, also yields vaccine candidates that exhibit one or more novel characteristics selected from (i) a change in viral growth in cell culture; (ii) a change in viral attenuation in the upper and/or lower respiratory tract of an infected host; (iii) a change in viral plaque size; and/or (vi) a change in immunogenicity, or, alternatively or concomitantly, elicit an altered host response, e.g., an increased anti-RSV neutralizing antibody response, T-helper cell response, cytotoxic T cell (CTL) response, and/or natural killer (NK) cell response, compared to a wild type or mutant parental RSV.

Within preferred aspects of the invention, recombinant RSV express high levels of the introduced cytokine or other immune modulator, for example up to 2.5 micrograms/ml as measured in the medium of infected tissue culture cells. The recombinant viruses are attenuated in vitro and in vivo, yet they exhibit a high level of protective efficacy against wild type RSV in vaccinated subjects are engineered to express undiminished or, more typically, increased levels of viral antigen(s) while also exhibiting an attenuated phenotype. Immunogenic potential is thus preserved due to the undiminished or increased mRNA transcription and antigen expression, while attenuation is achieved through concomitant reductions in RNA replication and virus growth. This novel suite of phenotypic traits is highly desired for vaccine development. Other useful phenotypic changes that are observed in recombinant RSV engineered to express an immune modulator(s) include a change in plaque size and altered cytopathogenicity compared to corresponding wild-type or mutant parental RSV strains.

In additional preferred embodiments, recombinant RSV engineered to express an immune modulator(s) exhibits attenuated viral growth in culture in and attenuation in vivo compared to growth and attenuation of a corresponding wild-type or mutant parental RSV strain. Growth, for example in cell cultures, may be reduced by about two-fold, more often about 5-fold, and preferably about 10-fold to 20-fold or greater overall (e.g., as measured after a 7-8 day period in culture) and replication in vivo will be comparably attenuated compared to growth and replication of the corresponding wild-type or mutant parental RSV strain. In more detailed aspects, recombinant RSV of the invention exhibit delayed kinetics of viral growth, wherein growth during an initial 2-5 day period is reduced by about 100-fold and up to 1,000-fold or more compared to kinetics of growth in the corresponding wild-type or mutant parental RSV strain. In other aspects, the recombinant virus exhibits increased antigen expression. In the most preferred aspects of the invention, recombinant RSV engineered to express an immune modulator(s) are significantly attenuated and yet are highly immunogenic and elicit a strong protective immune response against RSV in vaccinated hosts.

The instant invention provides for development of live-attenuated RSV vaccine candidates expressing one or more immune modulatory molecule(s). These recombinant viruses are constructed through a cDNA intermediate and cDNA-based recovery system. Recombinant viruses which are made from cDNA replicate independently and are propagated in the same manner as if they were biologically-derived. The recombinant RSV of the invention can be further modified to incorporate additional attenuating mutations, as well as a variety of other mutations and nucleotide modifications, to yield desired structural or phenotypic affects.

Detailed descriptions of the materials and methods for producing recombinant RSV from cDNA, and for making and testing the full range of mutations and nucleotide modifications disclosed herein as supplemental aspects of the present invention, are set forth in, e.g., U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. Pat. No. 5,993,824, issued Nov. 30, 1999 (corresponding to International Publication No. WO 98/02530); U.S. patent application Ser. No. 09/291,894, filed by Collins et al. on Apr. 13, 1999; U.S. Provisional Patent Application No. 60/129,006, filed by Murphy et al. on Apr. 13, 1999; Crowe et al., *Vaccine* 12: 691-699, 1994; and Crowe et al., *Vaccine* 12: 783-790, 1994; Collins, et al., *Proc Nat. Acad. Sci. USA* 92:11563-11567, 1995; Bukreyev, et al., *J Virol* 70:6634-41, 1996, Juhasz et al., *J. Virol.* 71(8):5814-5819, 1997; Durbin et al., *Virology* 235: 323-332, 1997; Karron et al., *J. Infect. Dis.* 176:1428-1436, 1997); He et al. *Virology* 237:249-260, 1997; Baron et al. *J. Virol.* 71:1265-1271, 1997; Whitehead et al., *Virology* 247(2): 232-9, 1998a; Whitehead et al., *J. Virol.* 72(5):4467-4471, 1998b Jin et al. *Virology* 251:206-214, 1998; Bukreyev, et al., Proc. Nat. Acad. Sci. USA 96:2367-2372, 1999; Bermingham and Collins, Proc. Natl. Acad. Sci. USA 96:11259-11264, 1999 Juhasz et al., Vaccine 17:1416-1424, 1999; Juhasz et al., J. Virol. 73:5176-5180, 1999; Teng and Collins, J. Virol. 73:466-473, 1999; Whitehead et al., J. Virol. 73:9773-9780, 1999; Whitehead et al., J. Virol. 73:871-877, 1999; and Whitehead et al., J. Virol. 73:3438-3442, 1999. Each of the foregoing references is thus incorporated herein by reference in its entirety for all purposes.

Exemplary methods for producing recombinant RSV from cDNA involve intracellular coexpression, typically from plasmids cotransfected into tissue culture cells, of an RSV antigenomic RNA and the RSV N, P, M2-1 and L proteins. This launches a productive infection that results in the production of infectious cDNA-derived virus, which is termed recombinant virus. Once generated, recombinant RSV is readily propagated in the same manner as biologically-derived virus, and a recombinant virus and a counterpart biologically-derived virus cannot be distinguished unless the former had been modified to contain one or more introduced changes as markers.

The ability to generate infectious RSV from cDNA provides a method for introducing predetermined changes into infectious virus via the cDNA intermediate. This method has been demonstrated to produce a wide range of infectious, attenuated derivatives of RSV, for example recombinant vaccine candidates containing one or more amino acid substitutions in a viral protein, deletion of one or more genes or ablation of gene expression, and/or one or more nucleotide substitutions in cis-acting RNA signals yielding desired effects on viral phenotype (see, e.g., Bukreyev et al., J. Virol. 71:8973-8982, 1997; Whitehead et al., J. Virol. 72:4467-4471, 1998; Whitehead et al., Virology 247:232-239, 1998; Bermingham and Collins, Proc. Natl. Acad. Sci. USA 96:11259-11264, 1999; Juhasz et al., Vaccine 17:1416-1424, 1999; Juhasz et al., J. Virol. 73:5176-5180, 1999; Teng and Collins, J. Virol. 73:466-473, 1999; Whitehead et al., J. Virol. 73:871-877, 1999; Whitehead et al., J. Virol. 73:3438-3442, 1999; and Collins et al., Adv. Virus Res. 54:423-451, 1999, each incorporated herein by reference).

Exemplary of the foregoing teachings are methods and procedures useful within the invention for mutagenizing, isolating and characterizing RSV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing documents detail procedures for determining replication, immunogenicity, genetic stability and protective efficacy of biologically derived and recombinantly produced attenuated human RSV, including human RSV A and B subgroups, in accepted model systems, including murine and non-human primate model systems. In addition, these documents describe general methods for developing and testing immunogenic compositions, including monovalent and bivalent vaccines, for prophylaxis and treatment of RSV infection.

Methods for producing infectious recombinant RSV by construction and expression of cDNA encoding an RSV genome or antigenome coexpressed with essential RSV proteins are also described in the above-incorporated documents (see, e.g., U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. patent application Ser. No. 08/892,403, filed Jul. 15, 1997 (corresponding to International Publication No. WO 98/02530); each incorporated herein by reference).

Also disclosed are methods for constructing and evaluating infectious recombinant RSV that are modified to incorporate phenotype-specific mutations identified in biologically-derived RSV mutants, e.g., cp and ts mutations adopted in recombinant RSV from biologically derived RSV mutants designated cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579). The recombinant RSV thus provided may incorporate one, two, or more ts mutations from the same, or different, biologically derived RSV mutant(s), for example one or more of the 248/404, 530/1009, or 530/1030 biological mutants. In the latter context, multiply attenuated recombinants may have a combination of attenuating mutations from two, three or more biological mutants, e.g., a combination of attenuating mutations from the RSV mutants 530/1009/404, 248/404/1009, 248/404/1030, or 248/404/1009/1030 mutants. In exemplary embodiments, one or more attenuating mutations specify a temperature-sensitive substitution at amino acid Phe521, Gln831, Met1169, or Tyr1321 in the RSV polymerase gene or a temperature-sensitive nucleotide substitution in the gene-start sequence of gene M2. In exemplary embodiments, these mutations involve identical or conservative changes with one or more of the following changes identified in the L gene of biologically derived mutant RSV; Ile for Asn43, Leu for Phe521, Leu for Gln831, Val for Met1169, and Asn for Tyr1321.

In one recently developed embodiment of the invention, the sequence of RSV mutant cpts248/955 was determined, with the exception of the first 29 nucleotides (3'- end of the genome) and the last 33 nucleotides (5'-end) of the genome. The sequence was then compared to that of parental virus cpts248. Mutant virus cpts248/955 contained all the mutations previously identified in cspts248, as well as the following mutations:1. Insertion of an A residue in the P gene-end signal at nucleotide 3236. This increases the poly-A tract from 7 A's to 8 A's. The is the same insertion observed previously in recombinant RSV rA2 virus preparations, which did not effect replication levels in mice. 2. An Asn to Ile mutation of amino acid 43 of the L polymerase due to A to U mutation at cpRSV nucleotide (nt) 8626. It is therefore considered that the cpts248/955 phenotype is attributed to the missense mutation at nt 8626. This is consistent with previous findings for the RSV 530, 1030, 1009, and 248 mutants.

Yet additional mutations that may be incorporated in recombinant RSV engineered to express an immune modulator(s) are mutations, e.g., attenuating mutations, identified in heterologous RSV or more distantly related negative stranded RNA viruses. In particular, attenuating and other desired mutations identified in one negative stranded RNA virus may be "transferred", e.g., copied, to a corresponding position within the genome or antigenome of the M2 ORF2 deletion and knock out mutants. Briefly, desired mutations in one heterologous negative stranded RNA virus are transferred to the RSV recipient (e.g., bovine or human RSV, respectively). This involves mapping the mutation in the heterologous virus, thus identifying by sequence alignment the corresponding site in the recipient RSV, and mutating the native sequence in the RSV recipient to the mutant genotype (either by an identical or conservative mutation), as described in International Application No. PCT/US00/09695 filed Apr. 12, 2000 and corresponding priority U.S. Provisional Patent Application Ser. No. 60/129,006, each incorporated herein by reference. As these disclosures teach, it is preferable to modify the recipient genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution should be engineered at the corresponding residue(s) in the recombinant virus. Preferably the substitution will involve an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue). Negative stranded RNA viruses from which exemplary mutations are identified and transferred into a recombinant RSV of the invention include other RSVs (e.g., murine), PIV, Sendai virus (SeV), Newcastle disease virus (NDV), simian virus 5 (SV5), measles virus (MeV), rindepest virus, canine distemper virus (CDV), rabies virus (RaV) and vesicular stomatitis virus (VSV). A variety of exemplary mutations are disclosed, including but not limited to an amino acid substitution of phenylalanine at position 521 of the RSV L protein (corresponding to a substitution of phenylalanine at position 456 of the HPIV3 L protein). In the case of mutations marked by deletions or insertions, these can be introduced as corresponding deletions or insertions into the recombinant virus, however the particular size and amino acid sequence of the deleted or inserted protein fragment can vary.

A variety of additional types of mutations are also disclosed in the foregoing incorporated references and can be readily engineered into a recombinant RSV of the invention to adjust attenuation, immunogenicity and/or provide other advantageous structural and/or phenotypic effects. For example, restriction site markers are routinely introduced within the recombinant antigenome or genome to facilitate cDNA construction and manipulation. Also described in the incorporated references are wide ranges of nucleotide modifications other than point or site-specific mutations that are useful within the instant invention. For example, methods and compositions are disclosed for producing recombinant RSV expressing an additional foreign gene, e.g., a chloramphenicol acetyl transferase (CAT) or luciferase gene. Such recombinants generally exhibit reduced growth associated with the inserted gene. This attenuation appears to increase with increasing length of the inserted gene. The finding that insertion of a foreign gene into recombinant RSV reduces level of replication and is stable during passage in vitro provides another effective method for attenuating RSV for vaccine use.

Additional nucleotide modifications disclosed in the foregoing references for incorporation into recombinant RSVs of the invention include partial or complete deletion or ablation of one or more non-essential (e.g., for replication and/or infectivity) RSV gene(s) or genome segment(s). RSV genes or genome segments may be deleted, including partial or complete deletions of open reading frames and/or cis-acting regulatory sequences of the RSV NS1, NS2, N, P, M, G, F, SH, M2 ORF1, M2 ORF2, and/or L genes. Within this aspect of the invention nucleotide modifications may be engineered to delete or silence a selected gene to achieve a recombinant vaccine candidate that replicates well in vitro but which is attenuated for replication in vivo (Bukreyev et al., *J. Virol.* 71:8973-8982, 1997; Teng et al., *J. Virol.* 73:466-473, 1999; each incorporated herein by reference). For example, deletion of the SH gene results in a virus, exemplified by rA2ΔSH, that replicates in vitro with an efficiency equal to or slightly better than that of wild-type rRSV (rA2) and which is moderately attenuated in mice and chimpanzees (Bukreyev et al., *J. Virol.* 71:8973-8982, 1997; Whitehead et al., *J. Virol.* 73:3438-3442, 1999; each incorporated herein by reference). Recombinant RSV from which the NS2 gene is deleted, designated rA2ΔNS2, exhibits reduced growth kinetics and reduced yield of infectious virus in vitro and is markedly attenuated in mice and chimpanzees (Teng et al., *J. Virol.* 73:466-473, 1999; Whitehead et al., *J. Virol.* 73:3438-3442, 1999; each incorporated herein by reference). Similar in vitro properties are disclosed for a recombinant bovine RSV from which the NS2 gene is deleted (Buchholz et al., *J. Virol.* 73:251-259, 1999; incorporated herein by reference).

In one example, a recombinant RSV was generated in which expression of the SH gene was ablated by removal of a polynucleotide sequence encoding the SH mRNA and protein. Deletion of the SH gene yielded not only recoverable, infectious RSV, but one which exhibited substantially improved growth in tissue culture based on both yield of infectious virus and plaque size. This improved growth in tissue culture specified by the SH deletion provides useful tools for developing RSV vaccine viruses engineered to express an immune modulator, for example by overcoming problems of poor RSV yields in culture. Moreover, these deletions are highly stable against genetic reversion, rendering RSV clones derived therefrom particularly useful as vaccine agents.

SH-minus RSV recombinants also exhibit site-specific attenuation in the upper respiratory tract of mice, which presents novel advantages for vaccine development. Certain of the current RSV strains under evaluation as live virus vaccines, for example cp mutants, do not exhibit significantly altered growth in tissue culture. These are host range mutations and they restrict replication in the respiratory tract of chimpanzees and humans approximately 100-fold in the lower respiratory tract. Another exemplary type of mutation, ts mutations, tend to preferentially restrict virus replication in the lower respiratory tract due to the gradient of increasing body temperature from the upper to the lower respiratory tract. In contrast to these cp and ts mutants, SH-minus RSV mutants have distinct phenotypes of greater restriction in the upper respiratory tract. This is particularly desirable for vaccine viruses for use in very young infants, because restriction of replication in the upper respiratory tract is required to ensure safe vaccine administration in this vulnerable age group whose members breathe predominantly through the nose. Further, in any age group, reduced replication in the upper respiratory tract will reduce morbidity from otitis media. In addition to these advantages, the nature of SH deletion mutations, involving e.g., nearly 400 nt and ablation of an entire mRNA, represents a type of mutation which will be highly refractory to reversion.

Also discussed in the context of SH gene modifications is a comparison of SH genes among different RSVs, including human and bovine RSVs, and other pneumoviruses to provide additional tools and methods for generating useful RSV recombinant vaccines. For example, the two RSV antigenic subgroups, A and B, exhibit a relatively high degree of conservation in certain SH domains. In two such domains, the N-terminal region and putative membrane-spanning domains of RSV A and B display 84% identity at the amino acid level, while the C-terminal putative ectodomains are more divergent (approx. 50% identity). Comparison of the SH genes of two human RSV subgroup B strains, 8/60 and 18537, identified only a single amino acid difference (Anderson et al., supra). The SH proteins of human versus bovine RSV are approximately 40% identical, and share major structural features including (i) an asymmetric distribution of conserved residues; (ii) very similar hydrophobicity profiles; (iii) the presence of two N-linked glycosylation sites with one site being on each side of the hydrophobic region; and (iv) a single cysteine residue on the carboxyterminal side of the central hydrophobic region of each SH protein. (Anderson et al., supra). By evaluating these and other sequence similarities and differences, selections can be made of heterologous sequence(s) that can be substituted or inserted within infectious M2 ORF2 deletion and knock out mutant RSV clones, for example to yield vaccines having multi-specific immunogenic effects or, alternatively or in addition, desirable effects such as attenuation.

Also disclosed in the context of gene deletions are the effects of changing gene position. For example, deletion of the SH gene results in an effective change in downstream gene position to a more promoter proximal position. This may be associated with an increase in transcription of downstream genes in the recombinant virus. Alternatively, the position of any gene can be changed to alter expression, for example by insertion or transpositioning of the gene to an upstream or downstream intergenic or other noncoding region. Thus, methods are provided for altering levels of RSV gene expression by changing gene order or position in the genome or antigenome. Decreased levels of expression of downstream genes are expected to specify attenuation phenotypes, whereas increased expression can achieve the opposite effects in recombinant RSV in permissive hosts, e.g., chimpanzees and humans.

In another example described in the above-incorporated references, expression of the NS2 gene is ablated by introduction of stop codons into the translational open reading frame (ORF). The rate of release of infectious virus was reduced for this NS2 knock out virus compared to wild-type. In addition, comparison of the plaques of the mutant and wild-type viruses showed that those of the NS2 knock out were greatly reduced in size. This type of mutation can thus be incorporated within viable recombinant RSV engineered to express a cytokine or other immune modulator to yield altered phenotypes, in this case reduced rate of virus growth and reduced plaque size in vitro. These and other knock out methods and mutants will therefore provide for yet additional recombinant RSV vaccine agents, based on the correlation between reduced plaque size in vitro and attenuation in vivo. Expression of the NS2 gene also was ablated by complete removal of the NS2 gene, yielding a virus with a similar phenotype.

Other RSV genes which have been successfully deleted include the NS1 and G genes. The former was deleted by removal of the polynucleotide sequence encoding the respective protein, and the latter by introducing a frame-shift or altering translational start sites and introducing stop codons. Specifically, the NS1 gene was deleted by removal of nucleotides 122 to 630 in the antigenomic cDNA, thereby joining the upstream nontranslated region of NS1 to the translational initiation codon of NS2. This virus, designated rA2ΔNS1, exhibited reduced RNA replication, plaque size, growth kinetics and approximately 10-fold lower yield of infectious virus in vitro. Interestingly, recovered NS1-minus virus produce small plaques in tissue culture albeit not as small as those of the NS2 deletion virus. The fact that the NS1-minus virus can grow, albeit with reduced efficiency, identifies the NS1 protein as an accessory protein, one that is dispensable to virus growth. The plaque size of the NS1-minus virus was similar to that of NS2 knock out virus in which expression of the NS2 protein was ablated by introducing translational stop codons into its coding sequence. The small plaque phenotype is commonly associated with attenuating mutations. This type of mutation can thus be incorporated within viable recombinant RSV to yield altered phenotypes. These and other knock out methods and mutants will therefore provide for yet additional recombinant RSV vaccine agents within the present invention, based on the known correlation between plaque size in vitro and attenuation in vivo. The NS2 knock out mutant exhibited a moderately attenuated phenotype in the upper respiratory tract and a highly attenuated phenotype in the lower respiratory tract in naive chimpanzees. This mutant also elicited greatly reduced disease symptoms in chimps while stimulating significant resistance to challenge by the wild-type virus (Whitehead et al., *J. Virol.* 73:3438-3442, 1999, incorporated herein by reference).

As noted above, another useful knock out mutation for incorporation within recombinant RSVs of the invention expressing an immune modulator involves deletion or ablation of the M2 ORF2, newly characterized herein to encode a transcription/replication regulatory factor M2-2 (see, U.S. Patent Application entitled PRODUCTION OF ATTENUATED RESPIRATORY SYNCYTIAL VIRUS VACCINES INVOLVING MODIFICATION OF M2 ORF2, filed by Collins et al. on Jul. 9, 2000 and identified by, and priority U.S. Provisional Application No. 60/143,097; Bermingham et al., *Proc. Natl. Acad. Sci. USA* 96:11259-11264, 1999; and Jin et al., *J. Virol.* 74:74-82, 2000, each incorporated herein by reference). In this aspect of the invention, expression of M2 ORF2 is preferably reduced or ablated by modifying the recombinant RSV genome or antigenome to incorporate a frame shift mutation, one or more stop codons in M2 ORF2, or by alteration of an initiation codon. Other alterations to achieve disruption of M2 ORF2 expression or M2-2 protein expression or function to generate attenuated RSV vaccine candidates include partial or complete deletion of the M2 ORF2 coding sequence, in whole or in part, to render the M2-2 protein partially or entirely non-functional or terminate its expression. Alternatively, expression of the M2-2 gene can be up-regulated or down-regulated in a recombinant RSV, for example by placing the M2-2 ORF in a more promoter-proximal or promoter-distal position, respectively in the recombinant genome or antigenome. Upregulation of M2-2 can also be achieved by constructing the genome or antigenome to include the M2-2 ORF as a separate gene with its own gene start end gene end signals. In preferred embodiments, M2 ORF2 deletion and knock out mutants exhibit attenuated viral growth compared to growth of a corresponding wild-type or mutant parental RSV strain. In addition, these recombinants exhibit delayed kinetics of viral growth. Furthermore, as M2-2 is a regulatory protein, alterations in virus growth and the pattern of gene expression can also be achieved by increasing rather than decreasing M2-ORF2 expression. As described above, this can be readily achieved by expression M2-ORF2 as a separate gene and, if necessary, moving the gene to a more promoter-proximal or promoter-distal location. Recombinant vaccine viruses bearing M2 ORF2 deletion and knock out mutations also preferably exhibit a change in mRNA transcription. One aspect of this change is delayed kinetics of viral mRNA synthesis compared to kinetics of mRNA synthesis of a corresponding wild-type or mutant parental RSV strain. However, after a period of time (e.g., at 24 hours post-infection) M2 ORF2 deletion and knock out mutants exhibit an increase in cumulative mRNA synthesis. This increase of cumulative mRNA synthesis can be achieved to levels of about 50-100%, 100-200%, 200-300% or greater compared to mRNA accumulation in the corresponding wild-type or mutant parental RSV strain.

Also provided within the invention are immune modulator-expressing RSV incorporating M2 ORF2 deletion and knock out mutations which exhibit a reduction in viral RNA replication compared to viral RNA replication (synthesis of genome/antigenome) of the corresponding wild-type or mutant parental RSV strain. Thus, accumulation of genomic RNA (e.g., after a post-infection period of 24 hours) is about 25-30%, 15-25%, 10-15% or lower compared to genomic RNA accumulation in the corresponding wild-type or mutant parental RSV strain. In preferred aspects, a cumulative molar ratio of mRNA to genomic RNA is increased 2- to 5-fold, 5-to 10-fold, 10- to 20-fold or greater compared to a cumulative molar ratio of mRNA to genomic RNA observed for the corresponding wild-type or mutant parental RSV strain.

In addition to these beneficial phenotype changes, incorporation of an M2 ORF2 deletion or knock out mutation within a recombinant RSV of the invention confers and increase in viral protein accumulation in infected cells compared to viral protein accumulation in cells infected with a corresponding wild-type or mutant parental RSV strain. Increased viral protein levels (e.g., at 36 hours post-infection) may be 50-100%, 100-200%, 200-300% or greater. This is particularly desirable because increased expression of viral antigens compared to expression of the antigen(s) in the corresponding wild-type or mutant parental RSV strain results in enhanced immunogenicity, thereby countering reduced antigen expression and immunogenicity resulting from desired attenuating mutations in the recombinant virus. This surprising assemblage of phenotypic traits is highly desired for vaccine development because the vaccine candidates can be suitably attenuated without sacrificing immunogenic potential, and may indeed exhibit increased immunogenic activity.

Yet additional methods and compositions provided within the incorporated references and useful within the invention involve different nucleotide modifications within RSV recombinants modified to express an immune modulator that alter different cis-acting regulatory sequences within the recombinant genome or antigenome. For example, a translational start site for a secreted form of the RSV G glycoprotein can be deleted to disrupt expression of this form of the G glycoprotein. The RSV G protein is synthesized in two forms: as an anchored type II integral membrane protein and as a N-terminally resected form which lacks essentially all of the membrane anchor and is secreted (Hendricks et al., *J. Virol.* 62:2228-2233, 1988). The two forms have been shown to be derived by translational initiation at two different start sites: the longer form initiates at the first AUG of the G ORF, and the second initiates at the second AUG of the ORF at codon 48 and is further processed by proteolysis (Roberts et al., *J. Virol.* 68: 4538-4546 1994). The presence of this second start site is highly conserved, being present in all strains of human, bovine and ovine RSV sequenced to date. It has been suggested that the soluble form of the G protein might mitigate host immunity by acting as a decoy to trap neutralizing antibodies. Also, soluble G has been implicated in preferential stimulation of a Th2-biased response, which in turn appears to be associated with enhanced immunopathology upon subsequent exposure to RSV. With regard to an RSV vaccine virus, it is highly desirable to minimize antibody trapping or imbalanced stimulation of the immune system, and so it would be desirable to ablate expression of the secreted form of the G protein. This has been achieved in recombinant virus. Thus, this mutation is particularly useful to qualitatively and/or quantitatively alter the host immune response elicited by the recombinant virus, rather than to directly attenuate the virus. Also the G protein gene may be deleted altogether. The resulting virus exhibits a host range effect, growing inefficiently on HEp-2 cells but growing as efficiently as wild type virus on Vero cells. Presumably, attachment function can also be provided by another protein or can be dispensed with altogether. Thus, the invention also provides live-attenuated RSV vaccine virus lacking the G protein and expressing an immune modulator to enhance immunogenicity.

The incorporated references also describe modulation of the phenotype of recombinant RSV by altering cis-acting transcription signals of other exemplary genes, e.g., NS1 and NS2. The results of these nucleotide modifications are consistent with modification of gene expression by altering cis-regulatory elements, for example to decrease levels of readthrough mRNAs and increase expression of proteins from downstream genes. The resulting recombinant viruses will preferably exhibit increased growth kinetics and increased plaque size. Exemplary modifications to cis-acting regulatory sequences include modifications to gene end (GE) and gene start (GS) signals associated with RSV genes. In this context, exemplary changes include alterations of the GE signals of the NS1 and NS2 genes rendering these signals identical to the naturally-occurring GE signal of the RSV N gene. The resulting recombinant virus exhibits increased growth kinetics and plaque size and therefore provide yet additional means for beneficially modifying phenotypes of RSV vaccine candidates expressing immune modulatory molecules.

Also useful within the instant invention are methods and compositions provided in the above-incorporated references that allow production of attenuated RSV expressing an immune modulator comprising sequences from both RSV subgroups A and B, e.g., to yield a RSV A or B vaccine or a bivalent RSV A/B vaccine. Thus, methods and compositions provided in the above-incorporated references that allow production of attenuated RSV vaccine viruses that express cytokine(s) and comprise sequences from both RSV subgroups A and B, e.g., to yield a RSV A or B vaccine or a bivalent RSV A/B vaccine (see, e.g., U.S. patent application Ser. No. 09/291,894, filed by Collins et al. on Apr. 13, 1999, incorporated herein by reference). In one example a RSV subgroup B-specific vaccine virus is provided in which an attenuated subgroup A virus is used to express the F and/or G glycoproteins of a subgroup B RSV. Because the F and G proteins are the major protective antigens and confer most of the RSV subgroup specificity, this chimeric virus will stimulate a strong immune response against subgroup B. This strategy may be implemented using two alternative approaches. One is to insert the G glycoprotein gene of a subgroup B virus into the subgroup A background (or vice-versa) as an additional gene. However, since the F protein also exhibits significant subgroup-specificity, it would be preferable to express both subgroup B glycoproteins in a subgroup B-specific vaccine. Moreover, it is desirable to further modify a subgroup B virus to achieve proper attenuation and immunogenicity in accordance with the teachings herein. Thus, the second, more desirable strategy to achieve an RSV subgroup B vaccine is to remove the G and F genes from a subgroup A recombinant cDNA background genome or antigenome, and replace them with the G and F genes of a subgroup B RSV. The resulting A/B chimeric RSV contains the internal proteins of subgroup A and the external protective antigens of subgroup B. This virus can then be attenuated to a desired level by systematic incorporation of attenuating mutations as described above. For example, specific attenuating mutations that have been incorporated into chimeric RSV A/B viruses include: (i) three of the five cp mutations, namely the mutation in N (V267I) and the two in L (C319Y and H1690Y), but not the two in F since these are removed by substitution with the B1 F gene;

(ii) the 248 (Q831L), 1030 (Y1321N) and, optionally, 404-L (D1183E) mutations which have been identified in attenuated strain A2 viruses; (iii) the single nucleotide substitution at position 9 in the gene-start signal of the M2 gene, and (iv) deletion of the SH gene. Other immediately available mutations in chimeric RSV A/B include, but are not limited to, NS1, NS2, SH, or G gene deletions, and the 530 and 1009 mutations, alone or in combination.

As noted above, the invention also embraces construction and use of recombinant RSV that express an immune modulatory molecule within a chimeric human-bovine recombinant virus. Chimeric human-bovine RSV for use within this aspect of the invention are generally described in U.S. patent application entitled PRODUCTION OF ATTENUATED, HUMAN-BOVINE CHIMERIC RESPIRATORY SYNCYTIAL VIRUS VACCINES, filed by Bucholz et al. on Jun. 23, 2000 and identified by, and in its priority U.S. Provisional Patent Application Ser. No. 60/143,132 (each incorporated herein by reference). These chimeric recombinant RSV include a partial or complete "background" RSV genome or antigenome derived from or patterned after a human or bovine RSV strain or subgroup virus combined with one or more heterologous gene(s) or genome segment(s) of a different RSV strain or subgroup virus to form the human-bovine chimeric RSV genome or antigenome. In certain aspects of the invention, chimeric RSV incorporate a partial or complete bovine RSV background genome or antigenome combined with one or more heterologous gene(s) or genome segment(s) from a human RSV. In alternate aspects of the invention chimeric RSV incorporate a partial or complete human RSV background genome or antigenome combined with one or more heterologous gene(s) or genome segment(s) from a bovine RSV.

In exemplary embodiments, the invention is directed to an infectious, cytokine-expressing RSV that comprises a major nucleocapsid (N) protein, a nucleocapsid phosphoprotein (P), a large polymerase protein (L), a RNA polymerase elongation factor, and a partial or complete RSV background genome or antigenome of a human or bovine RSV combined with one or more heterologous gene(s) and/or genome segment(s) of a different RSV to form a human-bovine chimeric RSV genome or antigenome. The heterologous gene(s) and/or genome segment(s) that are useful within the invention include one or more RSV NS1, NS2, N, P, M, SH, M2(ORF1), M2(ORF2), L, F or G gene(s) or genome segment(s). Alternatively, heterologous genes and genome segments for incorporation within human-bovine chimeric RSV may include a leader, trailer or intergenic region of the RSV genome, or a segment thereof. Various polynucleotides encoding one or more cytokines can be incorporated within the chimeric genome or antigenome.

Within more detailed embodiments, recombinant RSV of the invention incorporate one or more heterologous genes and/or genome segments that encode a RSV F, G and/or SH glycoprotein or an immunogenic domain or epitope thereof. Alternatively, the recombinant RSV may incorporate a chimeric glycoprotein having both human and bovine glycoprotein domains or immunogenic epitopes. For example, the latter type of chimera may be constructed by incorporation into a bovine background genome or antigenome a heterologous genome segment encoding a glycoprotein ectodomain in proper reading frame with a genome segment encoding a functional remaining portion of the corresponding glycoprotein in the bovine genome or antigenome, whereby the resultant chimeric virus expresses a functional chimeric glycoprotein.

In other alternative embodiments of the invention, human-bovine chimeric RSV modified to express an immune modulatory molecule are provided wherein a human RSV "backbone" is attenuated by incorporation of a selected bovine gene, genome segment, or plurality of genes or genome segments. In certain embodiments selected heterologous gene sets from BRSV are coordinately transferred into a HRSV background genome or antigenome. Exemplary bovine RSV genes from which individual or coordinately transferred groups of genes may be selected include the RSV N, P, NS1, NS2, M2-1 and M genes, which may be replaced singly or in any combination in a human RSV background genome or antigenome by one or more heterologous gene(s) from a bovine RSV to yield an attenuated chimeric derivative. In more detailed aspects, both N and P genes of a human RSV are replaced coordinately by counterpart N and P genes from a bovine RSV. This coordinate gene replacement is facilitated by functional cooperativity between certain genes in the RSV genome, which often arises in the case of neighboring gene pairs in the genome. Thus, in other alternative embodiments, both NS1 and NS2 genes of a human RSV are replaced by counterpart NS1 and NS2 genes from a bovine RSV. In yet additional embodiments, two or more of the M2-1, M2-2 and L genes of a HRSV are replaced by counterpart genes from a bovine RSV. For certain vaccine candidates within the invention for which a high level of host-range restriction is desired, each of the N, P, NS1, NS2, M2-1 and M genes of a human RSV are replaced by counterpart N, P, NS1, NS2, M2-1 and M genes from a bovine RSV. Within these various constructs, any selected modification relating to cytokine expression disclosed herein can be incorporated in the chimeric genome or antigenome.

Within a different aspect of the invention, human-bovine chimeric RSV modified to express a cytokine as disclosed herein are constructed wherein the chimeric genome or antigenome comprises a partial or complete bovine RSV background genome or antigenome combined with one or more heterologous gene(s) and/or genome segment(s) from a human RSV. In certain embodiments, one or more human RSV glycoprotein genes selected from F, G and SH, or one or more genome segment(s) encoding cytoplasmic domain, transmembrane domain, ectodomain or immunogenic epitope portion(s) of F, G, and/or SH is/are added or substituted within a partial or complete bovine RSV background genome or antigenome. For example, one or both human RSV glycoprotein genes F and G may be substituted to replace one or both counterpart F and G glycoprotein genes in a partial bovine RSV background genome or antigenome. Within these and related embodiments, the human-bovine chimeric genome or antigenome can incorporate antigenic determinants from one or both subgroup A and subgroup B human RSV. In more detailed aspects, both human RSV glycoprotein genes F and G are substituted to replace counterpart F and G glycoprotein genes in the bovine RSV background genome or antigenome. An exemplary human-bovine chimeric RSV bearing these features described in the incorporated references is rBRSV/A2. In combination with one or more of the modifications provided in this chimeric virus, the vaccine candidate virus will incorporate a modification directing cytokine expression as disclosed herein.

Yet additional human-bovine chimeric RSV of the invention having a modification to direct expression of an immune modulatory molecule incorporate one or more human RSV glycoprotein genes selected from F, G and SH which are added or substituted at a position that is more promoter-proximal compared to a wild-type gene order position of a counterpart gene or genome segment within a partial or complete bovine RSV background genome or antigenome. In one such embodiment, both human RSV glycoprotein genes G and F are substituted at gene order positions 1 and 2, respectively, to replace counterpart G and F glycoprotein genes deleted at wild type positions 7 and 8, respectively in a partial bovine RSV background genome or antigenome. An exemplary human-bovine chimeric RSV bearing these features described in the above-incorporated disclosures is rBRSV/A2-G1F2.

Coordinate gene transfers within human-bovine chimeric RSV are also directed to introduction of human antigenic genes within a bovine background genome or antigenome. In certain embodiments, one or more human RSV envelope-associated genes selected from F, G, SH, and M is/are added or substituted within a partial or complete bovine RSV background genome or antigenome. For example, one or more human RSV envelope-associated genes selected from F, G, SH, and M may be added or substituted within a partial bovine RSV background genome or antigenome in which one or more envelope-associated genes selected from F, G, SH, and M is/are deleted. In more detailed aspects, one or more genes from a gene set defined as human RSV envelope-associated genes F, G, and M are added within a partial bovine RSV background genome or antigenome in which envelope-associated genes F, G, SH, and M are deleted. An exemplary human-bovine chimeric RSV bearing these features described in the incorporated references is rBRSV/A2-MGF. In combination with one or more of the modifications provided in this chimeric virus, the invention will incorporate a selected modification to direct cytokine expression by the recombinant virus.

The introduction of heterologous immunogenic proteins, domains and epitopes to produce chimeric RSV that also express immune modulatory molecules is particularly useful to generate novel immune responses in an immunized host. Addition or substitution of an immunogenic gene or genome segment from one, donor RSV subgroup or strain within a recipient genome or antigenome of a different RSV subgroup or strain can generate an immune response directed against the donor subgroup or strain, the recipient subgroup or strain, or against both the donor and recipient subgroup or strain. To achieve this purpose, recombinant RSV expressing an immune modulator may also be constructed that express a chimeric protein, e.g., an immunogenic glycoprotein having a cytoplasmic tail and/or transmembrane domain specific to one RSV fused to an ectodomain of a different RSV to provide, e.g., a human-bovine fusion protein, or a fusion protein incorporating domains from two different human RSV subgroups or strains. In a preferred embodiment, an RSV expressing an immuno-modulatory molecule has its genome or antigenome further modified to encode a chimeric glycoprotein in the recombinant virus or subviral particle having both human and bovine glycoprotein domains or immunogenic epitopes. For example, a heterologous genome segment encoding a glycoprotein ectodomain from a human RSV F, SH or G glycoprotein may be joined with a polynucleotide sequence (i.e., a genome segment) encoding the corresponding bovine F, SH or G glycoprotein cytoplasmic and endodomains to form the human-bovine chimeric RSV genome or antigenome.

In other embodiments, recombinant RSVs useful in a vaccine formulation can be conveniently modified to accommodate antigenic drift in circulating virus. Typically the modification will be in the G and/or F proteins. An entire G or F gene, or a genome segment encoding a particular immunogenic region thereof, from one RSV strain is incorporated into a chimeric RSV genome or antigenome cDNA by replacement of a corresponding region in a recipient clone of a different RSV strain or subgroup, or by adding one or more copies of the gene, such that several antigenic forms are represented. Progeny virus produced from the modified RSV clone can then be used in vaccination protocols against emerging RSV strains.

In yet additional aspects of the invention, recombinant RSVs modified to express an immune modulatory molecule can be readily designed as "vectors" to incorporate antigenic determinants from different pathogens, including more than one RSV strain or group (e.g., both human RSV A and RSV B subgroups), human parainfluenza virus (HPIV) including HPIV3, HPIV2 and HPIV1, measles virus and other pathogens (see, e.g., U.S. Provisional Patent Application Ser. No. 60/170,195; U.S. patent application Ser. No. 09/458,813; and 09/459,062, each incorporated herein by reference). Within various embodiments, the recombinant genome or antigenome comprises a partial or complete RSV "vector genome or antigenome" combined with one or more heterologous genes or genome segments encoding one or more antigenic determinants of one or more heterologous pathogens. The heterologous pathogen may be a heterologous RSV (i.e., a RSV of a different strain or subgroup), and the heterologous gene or genome segment may encode a RSV NS1, NS2, N, P, M, SH, M2(ORF1), M2(ORF2), L, F or G protein or fragment (e.g., a immunogenic domain or epitope) thereof. For example, the vector genome or antigenome may be a partial or complete RSV A genome or antigenome and the heterologous gene(s) or genome segment(s) may encode antigenic determinant(s) of a RSV B subgroup virus.

In alternative embodiments, the RSV vector genome or antigenome is a partial or complete bovine RSV (BRSV) genome or antigenome and the heterologous gene(s) or genome segment(s) encoding the antigenic determinant(s) is/are of one or more human RSVs (HRSVs). For example, the partial or complete BRSV genome or antigenome may incorporate one or more gene(s) or genome segment(s) encoding one or more HRSV glycoprotein genes selected from F, G and SH, or one or more genome segment(s) encoding cytoplasmic domain, transmembrane domain, ectodomain or immunogenic epitope portion(s) of F, G, and/or SH of HRSV.

In other alternate embodiments, RSV modified to express an immune modulatory molecule which are designed as "vectors" for carrying heterologous antigenic determinants incorporate one or more antigenic determinants of a non-RSV pathogen, such as a human parainfluenza virus (HPIV). In one exemplary embodiment, one or more HPIV1, HPIV2, or HPIV3 gene(s) or genome segment(s) encoding one or more HN and/or F glycoprotein(s) or antigenic domain(s), fragment(s) or epitope(s) thereof is/are added to or incorporated within the partial or complete HRSV vector genome or antigenome. In more detailed embodiments, a transcription unit comprising an open reading frame (ORF) of an HPIV1, HPIV2, or HPIV3 HN or F gene is added to or incorporated within the chimeric HRSV vector genome or antigenome.

In yet additional alternate embodiments, the recombinant genome or antigenome of an RSV modified to express an immune modulatory molecule comprises a partial or complete HRSV or BRSV genome or antigenome and the heterologous pathogen is selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses. Based on this exemplary list of candidate pathogens, the selected heterologous antigenic determinant(s) may be selected from measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, Flavivirus E and NS1 proteins, and alphavirus E protein, and antigenic domains, fragments and epitopes thereof. In one embodiment, the heterologous pathogen is measles virus and the heterologous antigenic determinant(s) is/are selected from the measles virus HA and F proteins and antigenic domains, fragments and epitopes thereof. To achieve such a chimeric construct, a transcription unit comprising an open reading frame (ORF) of a measles virus HA gene may be added to or incorporated within a HRSV vector genome or antigenome.

In all embodiments of the invention that involve construction of a chimeric RSV, the addition or substitution of a heterologous or "donor" polynucleotide to a recipient or "background" genome or antigenome can involve only a portion of a donor gene of interest. Commonly, non-coding nucleotides such as cis-acting regulatory elements and intergenic sequences need not be transferred with the donor gene coding region. Thus, a coding sequence (e.g., a partial or complete open reading frame (ORF)) of a particular gene may be added or substituted to the partial or complete background genome or antigenome under control of a heterologous promoter (e.g., a promoter existing in the background genome or antigenome) of a counterpart gene or different gene as compared to the donor sequence. A variety of additional genome segments provide useful donor polynucleotides for inclusion within a chimeric genome or antigenome to express chimeric RSV having novel and useful properties. For example, heterologous genome segments may encode part or all of a glycoprotein cytoplasmic tail region, transmembrane domain or ectodomain, an epitopic site or region, a binding site or region containing a binding site, an active site or region containing an active site, etc., of a selected protein from a human or bovine RSV. These and other genome segments can be added to a complete background genome or antigenome or substituted therein for a counterpart genome segment to yield novel chimeric RSV recombinants. Certain recombinants will express a chimeric protein, e.g., a protein having a cytoplasmic tail and/or transmembrane domain of one RSV fused to an ectodomain of another RSV.

In other detailed aspects of the invention, RSV modified to express an immune modulatory molecule are created or modified by shifting a relative gene order or spatial position of one or more genes or genome segments within a recombinant RSV genome or antigenome—to generate a recombinant vaccine virus that is infectious, attenuated and immunogenic in humans and other mammals (see, U.S. Provisional Patent Application entitled RESPIRATORY SYNCYTIAL VIRUS VACCINES EXPRESSING PROTECTIVE ANTIGENS FROM PROMOTOR-PROXIMAL GENES, filed by Krempl et al., Jun. 23, 2000 and identified by Appl. Ser. No. 60/213,708, incorporated herein by reference). These recombinant RSVs of the invention typically comprise a major nucleocapsid (N) protein, a nucleocapsid phosphoprotein (P), a large polymerase protein (L), a RNA polymerase elongation factor, and a partial or complete recombinant RSV genome or antigenome having one or more positionally shifted RSV genes or genome segments within the recombinant genome or antigenome. In certain aspects of the invention, the recombinant RSV features one or more positionally shifted genes or genome segments that may be shifted to a more promoter-proximal or promoter-distal position by insertion, deletion, or rearrangement of one or more displacement polynucleotides within the partial or complete recombinant RSV genome or antigenome. Displacement polynucleotides may be inserted or rearranged into a non-coding region (NCR) of the recombinant genome or antigenome, or may be incorporated in the recombinant RSV genome or antigenome as a separate gene unit (GU).

In exemplary embodiments of the invention, isolated infectious recombinant RSV are constructed by addition, deletion, or rearrangement of one or more displacement polynucleotides that may be selected from one or more RSV gene(s) or genome segment(s) selected from RSV NS1, NS2, N, P, M, SH, M2(ORF1), M2(ORF2), L, F and G genes and genome segments and leader, trailer and intergenic regions of the RSV genome and segments thereof. In more detailed embodiments, polynucleotide inserts, and deleted or rearranged elements within the recombinant RSV genome or antigenome are selected from one or more bovine RSV (BRSV) or human RSV (HRSV) gene(s) or genome segment(s) selected from RSV NS1, NS2, N, P, M, SH, M2(ORF1), M2(ORF2), L, F and G gene(s) or genome segment(s) and leader, trailer and intergenic regions of the RSV genome or segments thereof.

In certain aspects of the invention, displacement polynucleotides are inserted to form the recombinant RSV genome or antigenome, to create or supplement the mutation introducing the polynucleotide that encodes the cytokine. Insertion of a displacement polynucleotide in this manner causes a positional shift of one or more "shifted" RSV genes or genome segments within the recombinant genome or antigenome to a more promoter-distal position relative to a position of corresponding gene(s) or genome segment(s) within a wild type RSV (e.g., HRSV A2 or BRSV kansas strain) genome or antigenome.

Alternatively, displacement polynucleotides may be deleted within recombinant RSV of the invention to in this manner to form the recombinant RSV genome or antigenome to accommodate or supplement the introduction of a cytokine-encoding gene. Deletion of a displacement polynucleotide in this context causes a positional shift of one or more "shifted" RSV genes or genome segments within the recombinant genome or antigenome to a more promoter-proximal position relative to a position of corresponding gene(s) or genome segment(s) within a wild type RSV. Displacement polynucleotides for deletion from recombinant RSV encoding a cytokine may be selected from one or more RSV NS1, NS2, SH, M2(ORF2), or G gene(s) or genome segment(s) thereof.

In more detailed embodiments of the invention, a displacement polynucleotide comprising a RSV NS1 gene is deleted to form the recombinant RSV genome or antigenome. Alternatively, a displacement polynucleotide comprising a RSV NS2 gene may be deleted to form the recombinant RSV genome or antigenome. Alternatively, a displacement polynucleotide comprising a RSV SH gene may be deleted to form the recombinant RSV genome or antigenome. Alternatively, a displacement polynucleotide comprising RSV M2(ORF2) can be deleted to form the recombinant RSV genome or antigenome. Alternatively, a displacement polynucleotide comprising a RSV G gene may be deleted to form the recombinant RSV genome or antigenome or antigenome.

In yet additional embodiments, multiple displacement polynucleotides comprising RSV genes or genome segments may be deleted within a mutant RSV encoding a cytokine. For example, RSV F and G genes may both be deleted to further modify the recombinant RSV genome or antigenome or antigenome having a gene insert encoding an immune modulatory molecule. Alternatively, the RSV NS1 and NS2 genes may both be deleted in the recombinant RSV genome or antigenome. Alternatively, the RSV SH and NS2 genes may both be deleted in the recombinant RSV genome or antigenome or antigenome. Alternatively, the RSV SH, NS1 and NS2 genes can all be deleted in the recombinant RSV genome or antigenome or antigenome.

In different embodiments of the invention, isolated infectious recombinant RSV encoding a cytokine or other immune modulatory molecule are provided wherein one or more displacement polynucleotides is/are added, substituted, or rearranged within the recombinant RSV genome or antigenome to cause a positional shift of one or more shifted RSV gene(s) or genome segment(s). Among these modifications, gene and genome segment insertions and rearrangements may introduce or rearrange the subject genes or genome segments to a more promoter-proximal or promoter-distal position relative to a respective position of each subject (inserted or rearranged) gene or genome segment within a corresponding (e.g., bovine or human) wild type RSV genome or antigenome. Displacement polynucleotides which may be added, substituted, or rearranged within the recombinant RSV genome or antigenome can be selected from one or more of the RSV NS1, NS2, SH, M2(ORF2), F, and/or G gene(s) or genome segment(s) thereof.

In more detailed embodiments, displacement polynucleotides are selected for insertion or rearrangement within the recombinant genome or antigenome which comprises one or more RSV genes or genome segments that encode one or more RSV glycoproteins or immunogenic domains or epitopes of RSV glycoproteins. In exemplary embodiments, these displacement polynucleotides are selected from genes or genome segments encoding RSV F, G, and/or SH glycoproteins or immunogenic domains or epitopes thereof. For example, one or more RSV glycoprotein gene(s) selected from F, G and SH may be added, substituted or rearranged within the recombinant RSV genome or antigenome to a position that is more promoter-proximal or promoter-distal compared to the wild type gene order position of the gene(s).

In exemplary embodiments, the RSV glycoprotein gene G is rearranged within the recombinant RSV genome or antigenome to a gene order position that is more promoter-proximal compared to the wild type gene order position of G. In more detailed aspects, the RSV glycoprotein gene G is shifted to gene order position 1 within said recombinant RSV genome or antigenome. In other exemplary embodiments, the RSV glycoprotein gene F is rearranged within the recombinant RSV genome or antigenome to a more promoter-proximal position, for example by shifting the F gene to gene order position 1 within the recombinant genome or antigenome. In yet additional exemplary embodiments, both RSV glycoprotein genes G and F are rearranged within the recombinant RSV genome or antigenome to gene order positions that are more promoter-proximal compared to their respective wild type gene order positions. In more detailed aspects, the RSV glycoprotein gene G is shifted to gene order position 1 and the RSV glycoprotein gene F is shifted to gene order position 2.

In yet additional constructs featuring glycoprotein gene shifts, recombinant M2 ORF2 deletion and knock out RSV are produced having one or more RSV glycoprotein gene(s) selected from F, G and SH, or a genome segment thereof, added, substituted or rearranged within the recombinant RSV genome or antigenome, wherein one or more RSV NS1, NS2, SH, M2(ORF2), or G gene(s) or genome segment(s) thereof is/are deleted. Thus, a gene or genome segment of RSV F, G, or SH may be added, substituted or rearranged in a background wherein a displacement polynucleotide comprising a RSV NS1 gene is deleted to form the recombinant RSV genome or antigenome. Alternatively, a gene or genome segment of RSV F, G, or SH may be added, substituted or rearranged in a background wherein a displacement polynucleotide comprising a RSV NS2 gene is deleted to form the recombinant RSV genome or antigenome. Alternatively, a gene or genome segment of RSV F, G, or SH may be added, substituted or rearranged in a background wherein a displacement polynucleotide comprising a RSV SH gene is deleted to form the recombinant RSV genome or antigenome.

In one embodiment, the RSV glycoprotein gene G is rearranged within a recombinant RSV genome or antigenome having an SH gene deletion to a gene order position that is more promoter-proximal compared to the wild type gene order position of G. In more detailed aspects, the RSV glycoprotein gene G is shifted to gene order position 1 within the recombinant RSV genome or antigenome, as exemplified by the recombinant vaccine candidate G1/ΔSH described in the above-incorporated references. In another embodiment, the RSV glycoprotein gene F is rearranged within a recombinant RSV genome or antigenome having an SH gene deletion to a more promoter-proximal proximal position. In more detailed aspects, the F gene is shifted to gene order position 1, as exemplified by the recombinant F1ΔΔSH. In yet another embodiment, both RSV glycoprotein genes G and F are rearranged within a ΔSH recombinant RSV genome or antigenome to gene order positions that are more promoter-proximal compared to the wild type gene order positions of G and F. In more detailed aspects, the RSV glycoprotein gene G is shifted to gene order position 1 and the RSV glycoprotein gene F is shifted to gene order position 1 within the recombinant RSV genome or antigenome, as exemplified by the recombinant G1F1/ΔSH.

Yet additional examples of gene position-shifted RSV are provided for use within the invention featuring shifts of glycoprotein gene(s) selected from F, G and SH, which are produced within a recombinant RSV genome or antigenome having multiple genes or genome segments selected from RSV NS1, NS2, SH, M2(ORF2), and G gene(s) or genome segment(s) deleted (see, U.S. Patent Application entitled RESPIRATORY SYNCYTIAL VIRUS VACCINES EXPRESSING PROTECTIVE ANTIGENS FROM PROMOTOR-PROXIMAL GENES, filed by Krempl et al., Jun. 23, 2000 and identified by Appl. Ser. No. 60/213,708, incorporated herein by reference). In one example, the RSV SH and NS2 genes are both deleted to form the recombinant RSV genome or antigenome or antigenome, and one or both RSV glycoprotein genes G and F are rearranged within the recombinant RSV genome to more promoter-proximal gene order positions. In more detailed aspects, G is shifted to gene order position 1 and F is shifted to gene order position 2, as exemplified by the recombinant G1F1/ΔNS2ΔSH. In another example, all of the RSV SH, NS1 and NS2 genes are deleted to form the recombinant RSV genome or antigenome or antigenome, and one or both RSV glycoprotein genes G and F are rearranged within the recombinant RSV genome or antigenome to more promoter-proximal positions, as exemplified by the recombinant vaccine candidate G1F1/ΔNS2ΔNS2ΔSH.

In yet additional aspects of the invention, gene position-shifted RSV modified to express a cytokine or other immune modulatory molecule are combined with or incorporated within human-bovine chimeric RSV (see, U.S. Patent Application entitled PRODUCTION OF ATTENUATED, HUMAN-BOVINE CHIMERIC RESPIRATORY SYNCYTIAL VIRUS VACCINES, filed by Bucholz et al. on Jun. 23, 2000 and identified by, and in its priority U.S. Provisional Patent Application Ser. No. 60/143,132 (each incorporated herein by reference). Within these aspects, the recombinant genome or antigenome comprises a partial or complete human RSV (HRSV) or bovine RSV (BRSV) background genome or antigenome combined with one or more heterologous gene(s) or genome segment(s) from a different RSV to for a human-bovine chimeric RSV genome or antigenome. The heterologous gene or genome segment of the different, HRSV or BRSV may be added or substituted at a position that is more promoter-proximal or promoter-distal compared to a wild type gene order position of a counterpart gene or genome segment within the partial or complete HRSV or BRSV background genome or antigenome. In one such example, both human RSV glycoprotein genes G and F are substituted at gene order positions 1 and 2, respectively, to replace counterpart G and F glycoprotein genes deleted at wild type positions 7 and 8, respectively in a partial bovine RSV background genome or antigenome, as exemplified by the recombinant virus rBRSV/A2-G1F2. In other embodiments, one or more human RSV envelope-associated genes selected from F, G, SH, and M is/are added or substituted within a partial or complete bovine RSV background genome or antigenome. In more detailed aspects, one or more human RSV envelope-associated genes selected from F, G, SH, and M is/are added or substituted within a partial bovine RSV background genome or antigenome in which one or more envelope-associated genes selected from F, G, SH, and M is/are deleted. In one embodiment, human RSV envelope-associated genes F, G, and M are added within a partial bovine RSV background genome or antigenome in which all of the envelope-associated genes F. G, SH, and M are deleted, as exemplified by the recombinant virus rBRSV/A2-MGF.

Desired phenotypic changes that are engineered into recombinant RSV of the invention include, but are not limited to, attenuation in cell culture or in a selected host environment, resistance to reversion from the attenuated phenotype, enhanced immunogenic characteristics (e.g., as determined by enhancement, or diminution, of an elicited immune response), upregulation or downregulation of transcription and/or translation of selected viral products, etc. In preferred aspects of the invention, RSV engineered to express an immune modulator are produced in which the recombinant genome or antigenome is further modified by introducing one or more attenuating mutations specifying an attenuating or further attenuating phenotype. These mutations may be generated de novo and tested for attenuating effects according to a rational design mutagenesis strategy as described in the above-incorporated references. Alternatively, the attenuating mutations can be identified in a biologically derived mutant RSV and thereafter incorporated into a recombinant RSV of the invention.

Attenuating mutations in biologically derived RSV for incorporation within RSV vaccine strains expressing one or more immune modulatory molecules may occur naturally or may be introduced into wild-type RSV strains by well known mutagenesis procedures. For example, attenuated RSV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) or exhibit temperature sensitive (ts) phenotypes in cell culture, as generally described herein and in U.S. Ser. No. 08/327,263, incorporated herein by reference.

By "biologically derived RSV" is meant any RSV not produced by recombinant means. Thus, biologically derived RSV include naturally occurring RSV of all subgroups and strains, including, e.g., naturally occurring RSV having a wild-type genomic sequence and RSV having genomic variations from a reference wild-type RSV sequence, e.g., RSV having a mutation specifying an attenuated phenotype. Likewise, biologically derived RSV include RSV mutants derived from a parental RSV strain by, inter alia, non-recombinant mutagenesis and selection procedures (see, e.g., International Publication WO 93/21310, incorporated herein by reference).

The level of temperature sensitivity of replication in exemplary attenuated RSV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of RSV correlate with the mutant's shutoff temperature. Replication of mutants with a shutoff temperature of 39° C. is moderately restricted, whereas mutants with a shutoff of 38° C. replicate less well and symptoms of illness are mainly restricted to the upper respiratory tract. A virus with a shutoff temperature of 35° C. to 37° C. will typically be fully attenuated in chimpanzees and substantially attenuated in humans. Thus, attenuated RSV of the invention which are ts will have a shutoff temperature in the range of about 35° C. to 39° C., and preferably from 35° C. to 38° C. The addition of a ts mutation into a partially attenuated strain produces a multiply attenuated virus useful within vaccine compositions of the invention.

A number of attenuated RSV strains as candidate vaccines for intranasal administration have been developed using multiple rounds of chemical mutagenesis to introduce multiple mutations into a virus which had already been attenuated during cold-passage (e.g., Connors et al., *Virology* 208: 478-484, 1995; Crowe et al., *Vaccine* 12: 691-699, 1994; and Crowe et al., *Vaccine* 12: 783-790, 1994, incorporated herein by reference). Evaluation in rodents, chimpanzees, adults and infants indicate that certain of these candidate vaccine strains are relatively stable genetically, are highly immunogenic, and may be satisfactorily attenuated. Nucleotide sequence analysis of some of these attenuated viruses indicates that each level of increased attenuation is associated with specific nucleotide and amino acid substitutions. The above-incorporated references also disclose how to routinely distinguish between silent incidental mutations and those responsible for phenotype differences by introducing the mutations, separately and in various combinations, into the genome or antigenome of infectious RSV clones. This process coupled with evaluation of phenotype characteristics of parental and derivative virus identifies mutations responsible for such desired characteristics as attenuation, temperature sensitivity, cold-adaptation, small plaque size, host range restriction, etc.

Mutations thus identified are compiled into a "menu" and are then introduced as desired, singly or in combination, to adjust a recombinant RSV vaccine that also expresses a cytokine to an appropriate level of attenuation, immunogenicity, genetic resistance to reversion from an attenuated phenotype, etc., as desired. Preferably, the recombinant RSV of the invention are attenuated by incorporation of at least one, and more preferably two or more, attenuating mutations identified from such a menu, which may be defined as a group of known mutations within a panel of biologically derived mutant RSV strains. Preferred panels of mutant RSV strains described herein are cold passaged (cp) and/or temperature sensitive (ts) mutants, for example a panel comprised of RSV mutants designated cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579) (each deposited under the terms of the Budapest Treaty with the American Type Culture Collection (ATCC) of 10801 University Boulevard, Manassas, Va. 20110-2209, U.S.A., and granted the above identified accession numbers).

From this exemplary panel of biologically derived mutants, a large menu of attenuating mutations are provided which can each be combined with any other mutation(s) within the panel for calibrating the level of attenuation in a recombinant RSV expressing an immune modulator, for vaccine use. Additional mutations may be derived from RSV having non-ts and non-cp attenuating mutations as identified, e.g., in small plaque (sp), cold-adapted (ca) or host-range restricted (hr) mutant strains. Attenuating mutations may be selected in coding portions of a donor or recipient RSV gene or in non-coding regions such as a cis-regulatory sequence. For example, attenuating mutations may include single or multiple base changes in a gene start sequence, as exemplified by a single or multiple base substitution in the M2 gene start sequence at nucleotide 7605.

RSV expressing an immune modulator that are designed and selected for vaccine use within the invention often have at least two and sometimes three or more attenuating mutations to achieve a satisfactory level of attenuation for broad clinical use. In one embodiment, at least one attenuating mutation occurs in the RSV polymerase gene and involves a nucleotide substitution specifying an amino acid change in the polymerase protein specifying a temperature-sensitive (ts) phenotype. Exemplary recombinants in this context incorporate one or more nucleotide substitutions in the large polymerase gene L resulting in an amino acid change at amino acid Asn 43, Phe521, Gln831, Met1169, or Tyr1321, as exemplified by the changes, Ile for Asn43, Leu for Phe521, Leu for Gln831, Val for Met1169, and Asn for Tyr1321. Alternately or additionally, recombinant RSV of the invention may incorporate a ts mutation in a different RSV gene, e.g., in the M2 gene. Preferably, two or more nucleotide changes are incorporated in a codon specifying an attenuating mutation, e.g., in a codon specifying a ts mutation, thereby decreasing the likelihood of reversion from an attenuated phenotype.

In accordance with the methods of the invention, recombinant RSVs that express an immune modulator(s) can be readily constructed and characterized that incorporate at least one and up to a full complement of attenuating mutations present within a panel of biologically derived mutant RSV strains. Thus, mutations can be assembled in any combination from a selected panel of mutants, for example, cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579). In this manner, attenuation of vaccine candidates can be finely adjusted for use in one or fewer classes of patients, including seronegative infants.

In more specific embodiments, recombinant RSV of the invention selected for vaccine use incorporate at least one and up to a full complement of attenuating mutations specifying a temperature-sensitive or other attenuating amino acid substitution at Asn43, Phe521, Gln831, Met1169 or Tyr1321 in the RSV polymerase gene L, or a temperature-sensitive nucleotide substitution in the gene-start sequence of gene M2. Alternatively or additionally, the recombinant RSV of the invention may incorporate at least one and up to a full complement of mutations from cold-passaged attenuated RSV, for example one or more mutations specifying an amino acid substitution at Val267 in the RSV N gene, Glu218 or Thr523 in the RSV F gene, Cys319 or His1690 in the RSV polymerase gene L.

In other detailed embodiments, recombinant RSVs of the invention are further modified to incorporate attenuating mutations selected from (i) a panel of mutations specifying temperature-sensitive amino acid substitutions Gln831 to Leu, and Tyr1321 to Asn in the RSV polymerase gene L; (ii) a temperature-sensitive nucleotide substitution in the gene-start sequence of gene M2; (iii) an attenuating panel of mutations adopted from cold-passaged RSV specifying amino acid substitutions Val267 to Ile in the RSV N gene, and Cys319 to Tyr and His1690 to Tyr in the RSV polymerase gene L; or (iv) deletion or ablation of expression of one or more of the RSV SH, NS1, NS2, G and M2-2 genes. Preferably, these and other examples of RSVs expressing an immune modulator incorporate at least two attenuating mutations adopted from biologically derived mutant RSV, which may be derived from the same or different biologically derived mutant RSV strains. Also preferably, these exemplary mutants have one or more of their attenuating mutations stabilized by multiple nucleotide changes in a codon specifying the mutation.

In accordance with the foregoing description, the ability to produce infectious RSV from cDNA permits introduction of specific engineered changes within RSV recombinants that express a cytokine or other immune modulator. In particular, infectious, recombinant RSV are employed for identification of specific mutation(s) in biologically derived, attenuated RSV strains, for example mutations which specify ts, ca, att and other phenotypes. Desired mutations are thus identified and introduced into recombinant RSV vaccine strains. The capability of producing virus from cDNA allows for routine incorporation of these mutations, individually or in various selected combinations, into a full-length cDNA clone, whereafter the phenotypes of rescued recombinant viruses containing the introduced mutations can be readily determined.

By identifying and incorporating specific, biologically derived mutations associated with desired phenotypes, e.g., a cp or ts phenotype, into infectious RSV clones, the invention provides for other, site-specific modifications at, or within close proximity to, the identified mutation. Whereas most attenuating mutations produced in biologically derived RSV are single nucleotide changes, other "site specific" mutations can also be incorporated by recombinant techniques into biologically derived or recombinant RSV. As used herein, site-specific mutations include insertions, substitutions, deletions or rearrangements of from 1 to 3, up to about 5-15 or more altered nucleotides (e.g., altered from a wild-type RSV sequence, from a sequence of a selected mutant RSV strain, or from a parent recombinant RSV clone subjected to mutagenesis). Such site-specific mutations may be incorporated at, or within the region of, a selected, biologically derived mutation. Alternatively, the mutations can be introduced in various other contexts within an RSV clone, for example at or near a cis-acting regulatory sequence or nucleotide sequence encoding a protein active site, binding site, immunogenic epitope, etc. Identification of useful mutations is facilitated by the use of minireplicon systems.

Site-specific RSV mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant RSV designed to incorporate additional, stabilizing nucleotide mutations in a codon specifying an attenuating mutation. Where possible, two or more nucleotide substitutions are introduced at codons that specify attenuating amino acid changes in a parent mutant or recombinant RSV clone, yielding a biologically derived or recombinant RSV having genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5-10 and up to 15 nucleotides or more 5' or 3', relative to a targeted nucleotide position, e.g., to construct or ablate an existing cis-acting regulatory element.

In addition to single and multiple point mutations and site-specific mutations, changes to recombinant RSVs expressing an immune modulator may include deletions, insertions, substitutions or rearrangements of whole genes or genome segments. These mutations may alter small numbers of bases (e.g., from 15-30 bases, up to 35-50 bases or more), large blocks of nucleotides (e.g., 50-100, 100-300, 300-500, 500-1,000 bases), or nearly complete or complete genes (e.g., 1,000-1,500 nucleotides, 1,500-2,500 nucleotides, 2,500-5,000, nucleotides, 5,00-6,5000 nucleotides or more) in the donor or recipient genome or antigenome, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In yet another aspect of the invention, recombinant RSVs expressing an immune modulator are employed as a vector for transient gene therapy of the respiratory tract. According to this embodiment the recombinant RSV genome or antigenome is further modified to incorporate a polynucleotide sequence encoding a gene product of interest. The gene product of interest is under control of the same or a different promoter from that which controls RSV expression. The infectious RSV produced by coexpressing the recombinant RSV genome or antigenome with the N, P, L and M2(ORF1) proteins and containing a sequence encoding the gene product of interest is administered to a patient. This can involve a recombinant RSV which is fully infectious (i.e., competent to infect cultured cells and produce infectious progeny), or can be a recombinant RSV which, for example, lacks one or more of the G, F and SH surface glycoprotein genes and is propagated in cells which provide one or more of these proteins in trans by stable or transient expression. In such a case, the recombinant virus produced will be competent for efficient infection, but would be highly inefficient in producing infectious particles. The lack of expressed cell surface glycoproteins also would reduce the efficiency of the host immune system in eliminating the infected cells. These features will increase the durability and safety of expression of the foreign gene.

In additional aspects, the invention provides for supplementation of mutations adopted into a recombinant RSV clone from biologically derived RSV, e.g., cp and ts mutations, with additional types of mutations involving the same or different genes in a further modified RSV. RSV encodes ten mRNAs and eleven proteins. Three of these are transmembrane surface proteins, namely the attachment G protein, fusion F protein involved in penetration, and small hydrophobic SH protein. G and F are the major viral neutralization and protective antigens. Four additional proteins are associated with the viral nucleocapsid, namely the RNA binding protein N, the phosphoprotein P, the large polymerase protein L, and the transcription elongation factor M2 ORF1. The M2 ORF2 also encodes a protein, M2-2 which is a transcription/translation regulatory factor. The matrix M protein is part of the inner virion and probably mediates association between the nucleocapsid and the envelope. Finally, there are two nonstructural proteins, NS1 and NS2, of unknown function. Each of these proteins can be selectively altered in terms of expression levels, or can be added deleted, substituted or rearranged, in whole or in part, alone or in combination with other desired modifications, in a recombinant RSV expressing an immune modulator to yield novel vaccine candidates.

Thus, in addition to or in combination with attenuating mutations adopted from biologically derived RSV mutants, the present invention also provides a range of additional methods for attenuating or otherwise modifying the phenotype of recombinant RSV engineered to express an immune modulator(s)—based on recombinant engineering of infectious RSV clones. A variety of alterations can be produced in an isolated polynucleotide sequence encoding the donor gene or genome segment or the background genome or antigenome for incorporation into infectious clones. More specifically, to achieve desired structural and phenotypic changes in recombinant RSV, the invention allows for introduction of modifications which delete, substitute, introduce, or rearrange a selected nucleotide or plurality of nucleotides from a parent genome or antigenome, as well as mutations which delete, substitute, introduce or rearrange whole gene(s) or genome segment(s), within the recombinant RSV engineered to express an immune modulator(s).

Desired modifications of infectious RSV according to the invention are typically selected to specify a desired phenotypic change, e.g., a change in viral growth, temperature sensitivity, ability to elicit a host immune response, attenuation, etc. These changes can be brought about either in a donor or recipient genome or antigenome by, e.g., mutagenesis of a parent RSV clone to ablate, introduce or rearrange a specific gene(s) or genome region(s) (e.g., a genome segment that encodes a protein structural domain, such as a cytoplasmic, transmembrane or extracellular domain, an immunogenic epitope, binding region, active site, etc. or a cis-acting signal). Genes of interest in this regard include all of the genes of the RSV genome:3'-NS1-NS2-N-P-M-SH-G-F-M21/M2-2-L-5', as well as heterologous genes from other RSV, other viruses and a variety of other non-RSV sources as indicated herein.

Also provided are modifications in recombinant RSV engineered to express an immune modulator(s) which modify expression of a selected gene, e.g., by introducing a termination codon within a selected RSV coding sequence, changing the position of an RSV gene relative to an operably linked promoter, introducing or removing an upstream start codon to alter rates of expression, modifying a translational start site, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes, e.g., in viral replication, transcription of selected gene(s), or translation of selected protein(s).

The ability to analyze and incorporate other types of attenuating mutations into recombinant RSV engineered to express an immune modulator(s) vaccine development extends to a broad assemblage of targeted changes in RSV clones. For example, deletion of the SH gene yields a recombinant RSV having novel phenotypic characteristics, including enhanced growth. In the present invention, an SH, NS1, NS2 or G gene (or any other selected, non-essential gene or genome segment) is deleted in a recombinant RSV, which may also have one or more additional mutations specifying an attenuated phenotype, e.g., one or more mutation(s) adopted from a biologically derived attenuated RSV mutant. In exemplary embodiments, an SH, NS1, NS2 or G gene is deleted in combination with one or more cp and/or ts mutations adopted from cpts248/404, cpts530/1009, cpts530/1030, or another selected mutant RSV strain or with other changes determined empirically, to yield a recombinant RSV having increased yield of virus, enhanced attenuation, and resistance to phenotypic reversion, due to the combined effects of the different mutations.

Any RSV gene which is not essential for growth, for example the SH, NS1 NS2 or G genes, can be ablated or otherwise modified in a recombinant RSV to yield desired effects on virulence, pathogenesis, immunogenicity and other phenotypic characters. For example, ablation by deletion of a non-essential gene such as SH results in enhanced viral growth in culture. Without wishing to be bound by theory, this effect is likely due in part to a reduced nucleotide length of the viral genome. In the case of one exemplary SH-minus clone, the modified viral genome is 14,825 nt long, 398 nucleotides less than wild-type. By engineering similar mutations that decrease genome size, e.g., in other coding or noncoding regions elsewhere in the RSV genome, such as in the P, M, F and M2 genes, the invention provides several readily obtainable methods and materials for improving RSV growth.

In addition, a variety of other genetic alterations can be produced in a RSV genome or antigenome for incorporation into infectious recombinant RSV engineered to express an immune modulator(s), alone or together with one or more attenuating mutations adopted from a biologically derived mutant RSV. Additional heterologous genes and genome segments (e.g. from different RSV genes, different RSV strains or types, or non-RSV sources) may be inserted in whole or in part, the order of genes changed, gene overlap removed, an RSV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Also provided within the invention are genetic modifications in recombinant RSV engineered to express an immune modulator(s) which alter or ablate the expression of a selected gene or genome segment without removing the gene or genome segment from the RSV clone. For example, this can be achieved by introducing a frame shift mutation or termination codon within a selected coding sequence, changing the position of a gene or introducing an upstream start codon to alter its rate of expression, or changing GS and/or GE transcription signals to alter phenotype (e.g., growth, temperature restrictions on transcription, etc.). In more detailed aspects of the invention, recombinant RSV engineered to express an immune modulator(s) are provided in which expression of the NS2 gene is ablated at the translational level without deletion of the gene or of a segment thereof, by, e.g., introducing two tandem translational termination codons into a translational open reading frame (ORF). This yields viable virus in which a selected gene has been silenced at the level of translation without deleting its gene. These forms of knock out virus will often exhibit reduced growth rates and small plaque sizes in tissue culture. Thus, these methods provide yet additional, novel types of attenuating mutations which ablate expression of a viral gene that is not one of the major viral protective antigens. In this context, knock out virus phenotypes produced without deletion of a gene or genome segment can be alternatively produced by deletion mutagenesis, as described herein, to effectively preclude correcting mutations that may restore synthesis of a target protein. Several other gene knock outs for incorporation within a recombinant RSV engineered to express an immune modulator(s) can be made using alternate designs and methods that are well known in the art (as described, for example, in (Kretschmer et al., *Virology* 216: 309-316, 1996; Radicle et al., *Virology* 217:418-412, 1996; and Kato et al., *EMBOSS J.* 16:178-587, 1987; and Schneider et al., *Virology* 277:314-322, 1996, each incorporated herein by reference).

Other mutations that are useful in recombinant RSV of the invention include mutations directed toward cis-acting signals, which can be identified, e.g., by mutational analysis of RSV minigenomes. For example, insertional and deletional analysis of the leader and trailer and flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into an antigenome or genome as described herein to further modify recombinant RSV engineered to express an immune modulator(s). Evaluation and manipulation of trans-acting proteins and cis-acting RNA sequences using the complete antigenome cDNA is assisted by the use of RSV minigenomes (see, e.g., Grosfeld et al., *J. Virol.* 69:5677-5686, 1995, incorporated herein by reference), whose helper-dependent status is useful in the characterization of those mutants which are too inhibitory to be recovered in replication-independent infectious virus.

Additional mutations that may be incorporated in recombinant RSV engineered to express an immune modulator(s) involve replacement of the 3' end of genome with its counterpart from antigenome, which is associated with changes in RNA replication and transcription. In addition, the intergenic regions (Collins et al., *Proc. Natl. Acad. Sci. USA* 83:4594-4598, 1986, incorporated herein by reference) can be shortened or lengthened or changed in sequence content, and the naturally-occurring gene overlap (Collins et al., *Proc. Natl. Acad. Sci. USA* 84:5134-5138, 1987, incorporated herein by reference) can be removed or changed to a different intergenic region by the methods described herein. In one exemplary embodiment, the level of expression of specific RSV proteins, such as the protective F and G antigens, can be increased by substituting the natural sequences with ones which have been made synthetically and designed to be consistent with efficient translation. In this context, it has been shown that codon usage can be a major factor in the level of translation of mammalian viral proteins (Haas et al., *Current Biol.* 6:315-324, 1996, incorporated herein by reference). Examination of the codon usage of the mRNAs encoding the F and G proteins of RSV, which are the major protective antigens, shows that the usage is consistent with poor expression. Thus, codon usage can be improved by the recombinant methods of the invention to achieve improved expression for selected genes. In another exemplary embodiment, a sequence surrounding a translational start site (preferably including a nucleotide in the −3 position) of a selected RSV gene is modified, alone or in combination with introduction of an upstream start codon, to modulate RSV gene expression by specifying up- or down-regulation of translation.

Alternatively, or in combination with other RSV modifications disclosed herein, recombinant RSV engineered to express an immune modulator(s) can be modulated by altering a transcriptional GS signal of a selected gene(s) of the virus. In one exemplary embodiment, the GS signal of NS2 is modified to include a defined mutation (e.g., the 404(M2) mutation described herein) to superimpose a ts restriction on viral replication.

In alternative embodiments, levels of gene expression in recombinant RSV engineered to express an immune modulator(s) are modified at the level of transcription. In one aspect, the position of a selected gene in the RSV gene map can be changed to a more promoter-proximal or promotor-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels often attended by a commensurate decrease in expression levels for reciprocally, positionally substituted genes. In one example, the NS2 gene (second in order in the RSV gene map) is substituted in position for the SH gene (sixth in order), yielding a predicted decrease in expression of NS2. In other exemplary embodiments, the F and G genes are transpositioned singly or together to a more promoter-proximal or promoter-distal site within the RSV gene map to achieve higher or lower levels of gene expression, respectively. These and other transpositioning changes yield novel immune modulator-expressing mutants of RSV having attenuated phenotypes, for example due to decreased expression of selected viral proteins involved in RNA replication, or having other desirable properties such as increased antigen expression.

Infectious recombinant RSV engineered to express an immune modulator(s) clones of the invention can also be engineered according to the methods and compositions disclosed herein to enhance immunogenicity and induce a level of protection greater than that provided by infection with a wild-type RSV or a parent RSV. For example, an immunogenic epitope from a heterologous RSV strain or type, or from a non-RSV source such as PIV, can be added to a recombinant clone by appropriate nucleotide changes in the polynucleotide sequence encoding the genome or antigenome. Alternatively, RSV can be engineered to add or ablate (e.g., by amino acid insertion, substitution or deletion) immunogenic proteins, protein domains, or forms of specific proteins (such as the secreted form of G) associated with desirable or undesirable immunological reactions.

Within the methods of the invention, additional genes or genome segments may be inserted into or proximate to the recombinant RSV genome or antigenome. These genes may be under common control with recipient genes, or may be under the control of an independent set of transcription signals. Genes of interest include the RSV genes identified above, as well as non-RSV genes, among others. This provides the ability to modify and improve the immune responses against RSV both quantitatively and qualitatively. In exemplary embodiments of the invention, insertion of foreign genes or genome segments, and in some cases of non-coding nucleotide sequences, within a recombinant RSV genome or antigenome results in a desired increase in genome length causing yet additional, desired phenotypic effects. Increased genome length results in attenuation of the resultant RSV, dependent in part upon the length of the insert.

Deletions, insertions, substitutions and other mutations involving changes of whole viral genes or genome segments within recombinant RSV engineered to express an immune modulator(s) yield genetically stable vaccine candidates, which are particularly important in the case of immunosuppressed individuals. Many of these changes will result in attenuation of resultant vaccine strains, whereas others will specify different types of desired phenotypic changes. For example, accessory (i.e., not essential for in vitro growth) genes are excellent candidates to encode proteins that specifically interfere with host immunity (see, e.g., Kato et al., *EMBO. J.* 16:578-87, 1997, incorporated herein by reference). Ablation of such genes in vaccine viruses is expected to reduce virulence and pathogenesis and/or improve immunogenicity.

In alternative aspects of the invention, the infectious immune modulator-expressing RSV produced from a cDNA-expressed genome or antigenome can be any of the RSV or RSV-like strains, e.g., human, bovine, murine, etc., or of any pneumovirus, e.g., pneumonia virus of mice avian pneumovirus (previously called turkey rhinotracheitis virus). To engender a protective immune response, the RSV strain may be one which is endogenous to the subject being immunized, such as human RSV being used to immunize humans. The genome or antigenome of endogenous RSV can be modified, however, to express RSV genes or genome segments from a combination of different sources, e.g., a combination of genes or genome segments from different RSV species, subgroups, or strains, or from an RSV and another respiratory pathogen such as PIV.

In certain embodiments of the invention, recombinant RSV engineered to express an immune modulator(s) are provided wherein genes or genome segments within a human or bovine RSV (e.g., a human RSV background genome or antigenome) are replaced with counterpart heterologous genes or genome segments from a non-human, non-bovine RSV, e.g., a murine RSV. Substitutions, deletions, and additions of RSV genes or genome segments in this context can include part or all of one or more of the NS1, NS2, N, P, M, SH, M2(ORF1), M2(ORF2) and L genes, or part or all of the G and F genes which preferably does not include the major neutralization and protective epitopes. Also, human or bovine RSV cis-acting sequences, such as promoter or transcription signals, can be replaced with non-human, non-bovine counterpart sequences. Thus, infectious recombinant RSV intended for administration to humans can be a human RSV that has been modified to contain genes from a murine RSV in addition to bovine RSV.

Replacement of a human RSV coding sequence (e.g., of NS1, NS2, SH, or G) or non-coding sequence (e.g., a promoter, gene-end, gene-start, intergenic or other cis-acting element) with a counterpart bovine RSV sequence yields chimeric RSV having a variety of possible attenuating and other phenotypic effects. In particular, host range and other desired effects arise from substituting a bovine RSV gene imported within a human RSV background, wherein the bovine gene does not function efficiently in a human cell, e.g., from incompatibility of the heterologous sequence or protein with a biologically interactive human RSV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In one such embodiment, a chimeric bovine-human RSV incorporates a substitution of the human RSV NP gene or genome segment with a counterpart bovine NP gene or genome segment, which chimera can optionally be constructed to incorporate additional genetic changes, e.g., point mutations or gene deletions. In exemplary embodiments, bovine RSV sequences are selected for introduction into human RSV based on known aspects of bovine RSV structure and function, as provided in, e.g., Pastey et al., *J. Gen. Viol.* 76:193-197, 1993; Pastey et al., *Virus Res.* 29:195-202, 1993; Zamora et al., *J. Gen. Virol.* 73:737-741, 1992; Mallipeddi et al., *J. Gen. Virol.* 74:2001-2004, 1993; Mallipeddi et al., *J. Gen. Virol.* 73:2441-2444, 1992; and Zamora et al., *Virus Res.* 24:115-121, 1992, each incorporated herein by reference, and in accordance with the teachings disclosed herein.

In other embodiments of the invention, mutations of interest for introduction within recombinant RSV engineered to express an immune modulator(s) are modeled after a tissue culture-adapted nonpathogenic strain of pneumonia virus of mice (the murine counterpart of human RSV) which lacks a cytoplasmic tail of the G protein (Randhawa et al., *Virology* 207:240-245, 1995). Accordingly, in one aspect of the invention the cytoplasmic and/or transmembrane domains of one or more of the human RSV glycoproteins, F, G and SH, are added, deleted, modified, or substituted within a chimeric RSV using a heterologous counterpart sequence (e.g., a sequence from a cytoplasmic, or transmembrane domain of a F, G, or SH protein of a bovine or murine RSV) to achieve a desired attenuation. As another example, a nucleotide sequence at or near the cleavage site of the F protein, or the putative attachment domain of the G protein, can be modified by point mutations, site-specific changes, or by alterations involving entire genes or genome segments to achieve novel effects on viral growth in tissue culture and/or infection and pathogenesis.

In more detailed aspects of the invention, recombinant RSV engineered to express an immune modulator(s) are employed as vectors for protective antigens of other pathogens, particularly respiratory tract pathogens such as parainfluenza virus (PIV). For example, recombinant RSV may be engineered which incorporate sequences that encode protective antigens from PIV to produce infectious, attenuated vaccine virus. The cloning of PIV cDNA and other disclosure supplemental to the instant invention is provided in U.S. Patent Application entitled PRODUCTION OF PARAINFLUENZA VIRUS VACCINES FROM CLONED NUCLEOTIDE SEQUENCES, filed May 22, 1998, Ser. No. 09/083,793 (corresponding to International Publication No. WO 98/53078) and its priority, provisional application filed May 23, 1997, Ser. No. 60/047,575, U.S. Provisional Patent Application entitled ATTENUATED HUMAN-BOVINE CHIMERIC PARAINFLUENZA VIRUS VACCINES, filed by Bailly et al. on Jul. 9, 1999 and identified by Appl. Ser. No. 60/143,134; and U.S.Patent Application entitled RECOMBINANT PARAINFLUENZA VIRUS VACCINES ATTENUATED BY DELETION OR ABLATION OF A NON-ESSENTIAL GENE, filed by Durbin et al. on Jul. 9, 1999 and identified by application Ser. No. 09/350,821; each incorporated herein by reference. This disclosure includes description of the following plasmids that may be employed to produce infectious PIV viral clones or to provide a source of PIV genes or genome segments for use within the invention: p3/7 (131) (ATCC 97990); p3/7(131)2G (ATCC 97989); and p218 (131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers.

According to this aspect of the invention, recombinant RSV engineered to express an immune modulator(s) are provided which incorporate at least one PIV sequence, for example a polynucleotide containing sequences from either or both PIV1 and PIV2 or PIV1 and PIV3. Individual genes of RSV may be replaced with counterpart genes from human PIV, such as the F glycoprotein genes of PIV1, PIV2, or PIV3. Alternatively, a selected, heterologous genome segment, such as a cytoplasmic tail, transmembrane domain or ectodomain of substituted for a counterpart genome segment in, e.g., the same gene in RSV, within a different gene in RSV, or into a non-coding sequence of the RSV genome or antigenome. In one embodiment, a genome segment from an F gene of HPIV3 is substituted for a counterpart human RSV genome segment to yield constructs encoding chimeric proteins, e.g. fusion proteins having a cytoplasmic tail and/or transmembrane domain of RSV fused to an ectodomain of PIV to yield a novel attenuated virus, and/or a multivalent vaccine immunogenic against both PIV and RSV. Alternatively, one or more PIV3 gene(s) or genome segment(s) can be added to a partial or complete, chimeric or non-chimeric RSV genome or antigenome.

In addition to the above described modifications to recombinant RSV engineered to express an immune modulator(s), different or additional modifications in RSV clones can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

In another aspect of the invention, compositions (e.g., isolated polynucleotides and vectors incorporating one or more cDNA(s) encoding a recombinant RSV engineered to express an immune modulator(s) are provided for producing isolated infectious vaccine viruses. Using these compositions and methods, infectious RSV are generated from a RSV genome or antigenome, a nucleocapsid (N) protein, a nucleocapsid phosphoprotein (P), a large (L) polymerase protein, and an RNA polymerase elongation factor. In related aspects of the invention, compositions and methods are provided for introducing the aforementioned structural and phenotypic changes into a recombinant RSV to yield infectious, attenuated vaccine viruses.

Introduction of the foregoing defined mutations into an infectious clone of a recombinant RSV engineered to express an immune modulator(s) can be achieved by a variety of well known methods. By "infectious clone" with regard to DNA is meant cDNA or its product, synthetic or otherwise, which can be transcribed into genomic or antigenomic RNA capable of serving as template to produce an infectious virus or subviral particle. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. This can be through the intermediate of a single-stranded phagemid form, such as using the Muta-gene® kit of Bio-Rad Laboratories (Richmond, Calif.) or a method using a double-stranded plasmid directly as template such as the Chameleon mutagenesis kit of Stratagene (La Jolla, Calif.), or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the RSV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of an RSV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome fragment is then amplified, its sequence is confirmed, and the mutated piece is then reintroduced into the full-length genome or antigenome clone.

The ability to introduce defined mutations into infectious RSV has many applications, including the analyses of RSV molecular biology and pathogenesis. For example, the functions of RSV proteins can be investigated and manipulated by introducing mutations which ablate or reduce their level of expression, or which yield mutant protein. In one exemplary embodiment hereinbelow, recombinant RSV is constructed in which expression of a viral gene, namely the SH gene, is ablated by deletion of the mRNA coding sequence and flanking transcription signals. Surprisingly, not only could this virus be recovered, but it grew efficiently in tissue culture. In fact, its growth was substantially increased over that of the wild-type, based on both yield of infectious virus and on plaque size. This improved growth in tissue culture from the SH deletion and other RSV derivatives of the invention provides useful tools for developing RSV vaccines, which overcome the problem of RSV's poor yield in tissue culture that had complicated production of vaccine virus in other systems. These deletions are highly stable against genetic reversion, rendering the RSV clones derived therefrom particularly useful as vaccine agents.

The invention also provides methods for producing recombinant RSV engineered to express an immune modulator(s) from one or more isolated polynucleotides, e.g., one or more cDNAs. According to the present invention cDNA encoding a RSV genome or antigenome is constructed for intracellular or in vitro coexpression with the necessary viral proteins to form infectious RSV. By "RSV antigenome" is meant an isolated positive-sense polynucleotide molecule which serves as the template for the synthesis of progeny RSV genome. Preferably a cDNA is constructed which is a positive-sense version of the RSV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, L and M2(ORF1) protein. In an RSV minigenome system, genome and antigenome were equally active in rescue, whether complemented by RSV or by plasmids, indicating that either genome or antigenome can be used and thus the choice can be made on methodological or other grounds.

A native RSV genome typically comprises a negative-sense polynucleotide molecule which, through complementary viral mRNAs, encodes eleven known species of viral proteins, i.e., the nonstructural species NS1 and NS2, N, P, matrix (M), small hydrophobic (SH), glycoprotein (G), fusion (F), M2(ORF1), M2(ORF2), and L, substantially as described in (Mink et al., *Virology* 185:615-624, 1991; Stec et al., *Virology* 183:273-287, 1991; and Connors et al., *Virol.* 208:478-484, 1995; Collins et al., *Proc. Nat. Acad. Sci. USA* 93:81-85, 1996), each incorporated herein by reference. It is recognized that one or more of these 11 proteins may be expressed in structural-distinct forms which might have functional differences, and one or more distinct protein species may remain to be identified.

For purposes of the present invention the genome or antigenome of the recombinant RSV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule, or can be expressed directly from the genome or antigenome cDNA.

By recombinant RSV is meant a RSV or RSV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in RSV gene expression, for example, a promoter, a structural or coding sequence which is transcribed into RSV RNA, and appropriate transcription initiation and termination sequences.

To produce infectious RSV from cDNA-expressed genome or antigenome, the genome or antigenome is coexpressed with those RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Alternatively, additional RSV proteins needed for a productive infection can be supplied by coexpression.

An RSV antigenome may be constructed for use in the present invention by assembling cloned cDNA segments, representing in aggregate the complete antigenome, by polymerase chain reaction (PCR; described in, e.g., U.S. Pat. Nos. 4,683,195 and 4,683,202, and *PCR Protocols: A Guide to Methods and Applications*, Innis et al., eds., Academic Press, San Diego, 1990, incorporated herein by reference) of reverse-transcribed copies of RSV mRNA or genome RNA. For example, cDNAs containing the left-hand end of the antigenome, spanning from an appropriate promoter (e.g., T7 RNA polymerase promoter) and the leader region complement to the SH gene, are assembled in an appropriate expression vector, such as a plasmid (e.g., pBR322) or various available cosmid, phage, or DNA virus vectors. The vector may be modified by mutagenesis and/or insertion of synthetic polylinker containing unique restriction sites designed to facilitate assembly. For example, a plasmid vector described herein was derived from pBR322 by replacement of the PstI-EcoR1 fragment with a synthetic DNA containing convenient restriction enzyme sites. Use of pBR322 as a vector stabilized nucleotides 3716-3732 of the RSV sequence, which otherwise sustained nucleotide deletions or insertions, and propagation of the plasmid was in bacterial strain DH10B to avoid an artifactual duplication and insertion which otherwise occurred in the vicinity of nt 4499. For ease of preparation the G, F and M2 genes can be assembled in a separate vector, as can be the L and trailer sequences. The right-hand end (e.g., L and trailer sequences) of the antigenome plasmid may contain additional sequences as desired, such as a flanking ribozyme and tandem T7 transcriptional terminators. The ribozyme can be hammerhead type (e.g., Grosfeld et al., *J. Virol.* 69:5677-

5686, 1995), which would yield a 3' end containing a single nonviral nucleotide, or can any of the other suitable ribozymes such as that of hepatitis delta virus (Perrotta et al., *Nature* 350:434-436, 1991) which would yield a 3' end free of non-RSV nucleotides. A middle segment (e.g., G-to-M2 piece) is inserted into an appropriate restriction site of the leader-to-SH plasmid, which in turn is the recipient for the L-trailer-ribozyme-terminator piece, yielding a complete antigenome. In an illustrative example described herein, the leader end was constructed to abut the promoter for T7 RNA polymerase which included three transcribed G residues for optimal activity; transcription donates these three nonviral G's to the 5' end of the antigenome. These three nonviral G residues can be omitted to yield a 5' end free of nonviral nucleotides. To generate a nearly correct 3' end, the trailer end was constructed to be adjacent to a hammerhead ribozyme, which upon cleavage would donate a single 3'-phosphorylated U residue to the 3' end of the encoded RNA.

In certain embodiments of the invention, complementing sequences encoding proteins necessary to generate a transcribing, replicating RSV nucleocapsid are provided by one or more helper viruses. Such helper viruses can be wild-type or mutant. Preferably, the helper virus can be distinguished phenotypically from the virus encoded by the RSV cDNA. For example, it is desirable to provide monoclonal antibodies which react immunologically with the helper virus but not the virus encoded by the RSV cDNA. Such antibodies can be neutralizing antibodies. In some embodiments, the antibodies can be used to neutralize the helper virus background to facilitate identification and recovery of the recombinant virus, or in affinity chromatography to separate the helper virus from the recombinant virus. Mutations can be introduced into the RSV cDNA which render the recombinant RSV nonreactive or resistant to neutralization with such antibodies.

A variety of nucleotide insertions and deletions can be made in genome or antigenome of a recombinant RSV engineered to express an immune modulator(s) to generate a properly attenuated clone. The nucleotide length of the genome of wild-type human RSV (15,222 nucleotides) is a multiple of six, and members of the Paramyxovirus and Morbillivirus genera typically abide by a "rule of six," i.e., genomes (or minigenomes) replicate efficiently only when their nucleotide length is a multiple of six (thought to be a requirement for precise spacing of nucleotide residues relative to encapsidating NP protein). Alteration of RSV genome length by single residue increments had no effect on the efficiency of replication, and sequence analysis of several different minigenome mutants following passage showed that the length differences were maintained without compensatory changes. Thus, RSV lacks the strict requirement of genome length being a multiple of six, and nucleotide insertions and deletions can be made in the RSV genome or antigenome without defeating replication of the recombinant RSV of the present invention.

Alternative means to construct cDNA encoding a genome or antigenome of a recombinant RSV engineered to express an immune modulator(s) include by reverse transcription-PCR using improved PCR conditions (e.g., as described in Cheng et al., *Proc. Natl. Acad. Sci. USA* 91:5695-5699, 1994; Samal et al., *J. Virol* 70:5075-5082, 1996, each incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the large size genome or antigenome.

The N, P and L proteins, necessary for RNA replication, require an RNA polymerase elongation factor such as the M2(ORF1) protein for processive transcription. Thus M2(ORF1) or a substantially equivalent transcription elongation factor for negative strand RNA viruses is required for the production of infectious RSV and is a necessary component of functional nucleocapsids during productive infection. The need for the M2(ORF1) protein is consistent with its role as a transcription elongation factor. The need for expression of the RNA polymerase elongation factor protein for negative strand RNA viruses is a feature of the present invention. M2(ORF1) can be supplied by expression of the complete M2-gene, either by the genome or antigenome or by coexpression therewith, although in this form the second ORF2 may also be expressed and can have an inhibitory effect on virus recovery. Therefore, for production of infectious virus using the complete M2 gene the activities of the two ORFs should be balanced to permit sufficient expression of M(ORF1) to provide transcription elongation activity yet not so much of M(ORF2) to inhibit RNA replication. Alternatively, the ORF1 protein is provided from a cDNA engineered to lack ORF2 or which encodes a defective ORF2. Efficiency of virus production may also be improved by co-expression of additional viral protein genes, such as those encoding envelope constituents (i.e., SH, M, G, F proteins).

To generate infectious recombinant RSV engineered to express an immune modulator(s), isolated polynucleotides (e.g., cDNA) encoding the recombinant M2 ORF2 deletion and knock out mutant RSV genome or antigenome are expressed, separately, or in cis, including expression from the antigenome or genome cDNA, with the N, P, L and M2(ORF1) proteins. These polynucleotides are inserted by transfection, electroporation, mechanical insertion, transduction or the like, into cells which are capable of supporting a productive RSV infection, e.g., HEp-2, FRhL-DBS2, MRC, and Vero cells. Transfection of isolated polynucleotide sequences may be introduced into cultured cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), DEAE-dextran mediated transfection (Ausubel et al., (ed.) *Current Protocols in Molecular Biology*, John Wiley and Sons, Inc., NY, 1987, cationic lipid-mediated transfection (Hawley-Nelson et al., *Focus* 15:73-79, 1993) or a commercially available transfection regent, e.g., LipofectACE® (Life Technologies) (each of the foregoing references are incorporated herein by reference).

The N, P, L and M2(ORF1) proteins are encoded by one or more cDNAs and expression vectors which can be the same or separate from that which encodes the genome or antigenome, and various combinations thereof. Furthermore, one or more proteins, and particularly the M2-1 protein, can be supplied directly from the antigenome or genome (Collins et al., *Virology* 259:251-258, 1999, incorporated herein by reference). Additional proteins may be included as desired, encoded by its own vector or by a vector encoding a N, P, L, or M2(ORF1) protein and/or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology,* 210:202-205, 1995, incorporated by reference). The viral proteins, and/or T7 RNA polymerase, can also be provided from transformed mammalian cells, or by transfection of preformed mRNA or protein.

Alternatively, synthesis of antigenome or genome can be conducted in vitro (cell-free) in a combined transcription-translation reaction, followed by transfection into cells. Or, antigenome or genome RNA can be synthesized in vitro and transfected into cells expressing RSV proteins.

To select candidate vaccine viruses according to the invention, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccinee sufficient to confer protection against serious disease caused by subsequent infection from wild-type virus. Contrary to expectations based on the results reported for other known attenuated RSVs, viruses of the invention are not only viable and more appropriately attenuated than previous mutants, but are more stable genetically in vivo than those previously studied mutants—retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like. Prior to the invention, genetic instability of the ts phenotype following replication in vivo has been common for ts viruses (Murphy et al., *Infect. Immun.* 37:235-242, 1982).

To propagate recombinant RSV engineered to express an immune modulator(s) for vaccine use and other purposes, a number of cell lines which allow for RSV growth may be used. RSV grows in a variety of human and animal cells. Preferred cell lines for propagating attenuated RS virus for vaccine use include DBS-FRhL-2, MRC-5, and Vero cells. Highest virus yields are usually achieved with epithelial cell lines such as Vero cells. Cells are typically inoculated with virus at a multiplicity of infection ranging from about 0.001 to 1.0 or more, and are cultivated under conditions permissive for replication of the virus, e.g., at about 30-37° C. and for about 3-5 days, or as long as necessary for virus to reach an adequate titer. Virus is removed from cell culture and separated from cellular components, typically by well known clarification procedures, e.g., centrifugation, and may be further purified as desired using procedures well known to those skilled in the art.

Recombinant RSVs engineered to express an immune modulator(s) and which have been satisfactorily attenuated and otherwise modified as described herein can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically derived or recombinant RSV) is tested for temperature sensitivity of virus replication, i.e. ts phenotype, and for the small plaque phenotype. Modified viruses are further tested in animal models of RSV infection. A variety of animal models have been described and are summarized in (Meignier et al., eds., Animal Models of Respiratory Syncytial Virus Infection, Merieux Foundation Publication, 1991, which is incorporated herein by reference). A cotton rat model of RSV infection is described in (U.S. Pat. No. 4,800,078 and Prince et al., *Virus Res.* 3:193-206, 1985), which are incorporated herein by reference, and is considered predictive of attenuation and efficacy in humans and non-human primates. In addition, a primate model of RSV infection using the chimpanzee is predictive of attenuation and efficacy in humans, as is described in detail in (Richardson et al., *J. Med. Virol.* 3:91-100, 1978; Wright et al., *Infect. Immun.* 37:397-400, 1982; Crowe et al., *Vaccine* 11:1395-1404, 1993, each incorporated herein by reference).

RSV model systems, including rodents and chimpanzees for evaluating attenuation and infectivity of RSV vaccine candidates are widely accepted in the art and the data obtained therefrom correlate well with RSV infection and attenuation. The mouse and cotton rat models are especially useful in those instances in which candidate RSV viruses display inadequate growth in chimpanzees, for example in the case of RSV subgroup B viruses.

In accordance with the foregoing description and based on the Examples below, the invention also provides compositions containing isolated, infectious recombinant RSV engineered to express an immune modulator(s) for vaccine use. The attenuated virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium where it can be propagated and characterized in a controlled setting. For example, attenuated RSV of the invention may be produced by an infected cell culture, separated from the cell culture and added to a stabilizer.

RSV vaccines of the invention contain as an active ingredient an immunogenically effective amount of RSV produced as described herein. Biologically derived or recombinant RSV can be used directly in vaccine formulations, or lyophilized. Lyophilized virus will typically be maintained at about 4° C. When ready for use the lyophilized virus is reconstituted in a stabilizing solution, e.g., saline, SPG, Mg++ and HEPES, with or without adjuvant, as further described below. The recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art. Preferred adjuvants also include Stimulon® QS-21 (Aquila Biopharmaceuticals, Inc., Farmingham, Mass.), MPL® (3-0-deacylated monophosphoryl lipid A; RIBI ImmunoChem Research, Inc., Hamilton, Mont.), and interleukin-12 (Genetics Institute, Cambridge, Mass.).

Upon immunization with a recombinant RSV vaccine composition as described herein, via aerosol, droplet, oral, topical or other route, the immune system of the host responds to the vaccine by producing antibodies specific for one or more RSV virus proteins, e.g., F and/or G glycoproteins. As a result of the vaccination the host becomes at least partially or completely immune to RSV infection, or resistant to developing moderate or severe RSV disease, particularly of the lower respiratory tract.

RSV vaccines of the invention may comprise attenuated virus that elicits an immune response against a single RSV strain or antigenic subgroup, e.g. A or B, or against multiple RSV strains or subgroups. In this context, the RSV can elicit a monospecific immune response or a polyspecific immune response against multiple RSV strains or subgroups. Alternatively, RSV having different immunogenic characteristics can be combined in a vaccine mixture or administered separately in a coordinated treatment protocol to elicit more effective protection against one RSV strain, or against multiple RSV strains or subgroups.

The host to which the vaccine is administered can be any mammal susceptible to infection by RSV or a closely related virus and capable of generating a protective immune response to antigens of the vaccinizing virus. Thus, suitable hosts include humans, non-human primates, bovine, equine, swine, ovine, caprine, lagamorph, rodents, etc. Accordingly, the invention provides methods for creating vaccines for a variety of human and veterinary uses.

The vaccine compositions containing the attenuated recombinant RSV engineered to express an immune modulator(s) are administered to a patient susceptible to or otherwise at risk of RSV infection in an "immunogenically effective dose" which is sufficient to induce or enhance the individual's immune response capabilities against RSV. In the case of human subjects, the attenuated virus of the invention is administered according to well established human RSV vaccine protocols, as described in, e.g., (Wright et al., *Infect. Immun.* 37:397-400, 1982; Kim et al., *Pediatrics* 52:56-63, 1973; and Wright et al., *J. Pediatr.* 88:931-936, 1976), which are each incorporated herein by reference. Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has never been observed with a live virus.

In all subjects, the precise amount of RSV vaccine administered and the timing and repetition of administration will be determined based on the patient's state of health and weight, the mode of administration, the nature of the formulation, etc. Dosages will generally range from about $10^3$ to about $10^6$ plaque forming units (PFU) or more, e.g., $10^7$ to $10^8$ PFU of virus per patient, more commonly from about $10^4$ to $10^5$ PFU virus per patient. In any event, the vaccine formulations should provide a quantity of attenuated RSV of the invention sufficient to effectively stimulate or induce an anti-RSV immune response, e.g., as can be determined by complement fixation, plaque neutralization, and/or enzyme-linked immunosorbent assay, among other methods. In this regard, individuals are also monitored for signs and symptoms of upper respiratory illness. As with administration to chimpanzees, the attenuated virus of the vaccine grows in the nasopharynx of vaccinees at levels approximately 10-fold or more lower than wild-type virus, or approximately 10-fold or more lower when compared to levels of incompletely attenuated RSV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered RSV strain expressing a cytokine or an additional protein rich in T cell epitopes may be particularly advantageous for adults rather than for infants. Alternatively, a lower level of attenuation may be selected for older vaccinees. RSV vaccines produced in accordance with the present invention can be combined with viruses expressing antigens of another subgroup or strain of RSV to achieve protection against multiple RSV subgroups or strains. Alternatively, the vaccine virus may incorporate protective epitopes of multiple RSV strains or subgroups engineered into one RSV clone as described herein.

Typically when different vaccine viruses are used they will be administered in an admixture simultaneously, but they may also be administered separately. For example, as the F glycoproteins of the two RSV subgroups differ by only about 10% in amino acid sequence, this similarity is the basis for a cross-protective immune response as observed in animals immunized with RSV or F antigen and challenged with a heterologous strain. Thus, immunization with one strain may protect against different strains of the same or different subgroup. However, optimal protection probably will require immunization against both subgroups.

The recombinant RSV engineered to express an immune modulator(s) elicit production of an immune response that is protective against serious lower respiratory tract disease, such as pneumonia and bronchiolitis when the individual is subsequently infected with wild—type RSV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

Preferred RSV recombinants of the present invention exhibit a very substantial diminution of virulence when compared to wild-type virus that is circulating naturally in humans. The virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation recombinant RSV engineered to express an immune modulator(s) may be determined by, for example, quantifying the amount of virus present in the respiratory tract of an immunized host and comparing the amount to that produced by wild-type RSV or other attenuated RSV which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 5- to 10-fold, 20-50 fold, 100- to 1000-fold or more less. Also, the level of replication of the attenuated RSV vaccine strain in the upper respiratory tract of the chimpanzee should be less than that of the RSV A2 ts-1 mutant, which was demonstrated previously to be incompletely attenuated in seronegative human infants. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RSV in the nasopharynx of an infected host are well known in the literature. Specimens are obtained by aspiration or washing out of nasopharyngeal secretions and virus quantified in tissue culture or other by laboratory procedure. See, for example, (Belshe et al., *J. Med. Virology* 1:157-162, 1977; Friedewald et al., *J. Amer. Med. Assoc.* 204:690-694, 1968; Gharpure et al., *J. Virol.* 3:414-421, 1969; and Wright et al., *Arch. Ges. Virusforsch.* 41:238-247, 1973), each incorporated herein by reference. The virus can conveniently be measured in the nasopharynx of host animals, such as chimpanzees.

In some instances it may be desirable to combine the RSV vaccines of the invention containing a recombinant RSV engineered to express an immune modulator(s) with vaccines that induce protective responses to other agents, particularly other childhood viruses. For example, a recombinant RSV vaccine of the present invention can be administered simultaneously with a PIV vaccine, such as described in Clements et al., *J. Clin. Microbiol.* 29:1175-1182, 1991, incorporated herein by reference. In another aspect of the invention the recombinant RSV can be employed as a vector for protective antigens of other respiratory tract pathogens, such as PIV, by incorporating the sequences encoding those protective antigens into the RSV genome or antigenome which is used to produce infectious RSV, as described herein.

The following examples are provided by way of illustration, not limitation. In brief, these examples describe.

EXAMPLE I

Construction and Characterization of a Recombinant RSV Expressing Interferon Gamma Interferon gamma (IFNγ), a type II interferon, is produced by T cells and natural killer (NK) cells and has diverse biological effects (for review, see refs. 1 and 2). IFNγ has intrinsic antiviral activity, up-regulates expression of major histocompatibility class I and II molecules, activates macrophages and NK cells, and has an important regulatory role in T helper (Th) cell proliferation. Two subsets of murine Th cells have been distinguished on the basis of the pattern of cytokine secretion: the Th1 subset, whose marker cytokines include IL-2 and IFNγ, and the Th2 subset, whose markers include IL-4, IL-5, IL-6 and IL-10. IFNγ preferentially inhibits the proliferation of Th2 cells, thus favoring a Th1 response.

In the present example, an infectious recombinant (r) human RSV (rRSV/mIFNγ) was constructed which encodes murine (m) IFNγ as a separate gene inserted into the G-F intergenic region. Cultured cells infected with rRSV/mIFNγ secreted 22 mg of mIFNγ per $10^6$ cells. The replication of rRSV/mIFNγ, but not that of a control chimeric rRSV containing the chloramphenicol acetyl transferase (CAT) gene as an additional gene, was 63- and 20-fold lower than that of wild type (wt) RSV in the upper and lower respiratory tract, respectively, of mice. Thus, the attenuation of rRSV/mIFNγ in vivo could be attributed to the activity of mIFNγ and not to the presence of the additional gene per se. The mice were completely resistant to subsequent challenge with wt RSV. Despite its growth restriction, infection of mice with rRSV/mIFNγ induced a level of RSV-specific antibodies which on day 56 was comparable to or greater than that induced by infection with wt RSV. Mice infected with rRSV/mIFNγ developed a high level of IFNγ mRNA and an increased amount of IL-12 p40 mRNA in their lungs, whereas other cytokine mRNAs tested were unchanged compared to those induced by wt RSV. Since attenuation of RSV typically is accompanied by a reduction in immunogenicity, expression of IFNγ by a rRSV represents a method of attenuation in which immunogenicity can be maintained rather than be reduced.

Plasmid Construction.

RSV gene-start and gene-end signals were attached to the mIFNγ cDNA by PCR with oligonucleotides TATACCCGG-GAT<u>GGGGCAAAT</u>*ATGAACGCTACACACTGCAT* (SEQ ID NO. 1) (positive-sense, the XmaI site is in bold, the RSV gene-start sequence is underlined, sequence specific to 5'-terminal part of mIFNγ gene is italicized, and the initiation codon is shown in bold italics) and ATTACCCGGGAA<u>TTTTTAATAACTT</u>*CAGCAGCGACTCCTTTTCC* (SEQ ID NO. 2) (negative-sense, the XmaI site is in bold, the RSV gene-end sequence is underlined, sequence specific to 3'-terminal part of mIFNγ gene is italicized, and the termination codon complement is shown in bold italics). The PCR product was cloned in plasmid pUC 19 and its sequence confirmed, and it was then cloned into the XmaI site of the previously described antigenome plasmid D46/1024 (13, FIG. 1).

RSV-Specific and Ig Isotype-Specific Enzyme-Linked Immunoadsorbent Assay (ELISA).

96-well plates coated with purified RSV F glycoprotein (4 µg/ml) were incubated with four-fold dilutions of mouse serum followed by one of the following biotinylated isotype-specific rat anti-mouse antibodies: (i) IgG1 kappa against IgG1 heavy chain, (ii) IgG2a kappa, allotype IgK-1A, against IgG2a heavy chain, and (iii) IgM monoclonal antibody clone LO-MA-7 against IgA heavy chain (Accurate Chemical and Scientific Company, NY). The plates were then incubated with streptavidin linked to alkaline phosphatase (Life Technologies, MD) and reacted with p-nitrophenyl phosphate solution (Sigma, MO). The specificity of the reagents for the indicated isotypes was confirmed by ELISA against the following commercially-obtained purified murine monoclonal antibodies, SC): IgG1 (MOPC 21), IgG2a (RPC 5), IgG3 (FLOPC 21) (Cappel/Organon Teknika, Pa.), IgG2b (MOPC 141), IgA (TEPC 15), and IgM (MOPC 104E) (Litton Bionetics, SC). Total IgG was detected by incubating F-coated plates with dilutions of the test sera followed by incubation with goat IgG specific to mouse IgG and conjugated to alkaline phosphatase (Cappel), which was then reacted with p-nitrophenyl phosphate. ELISA measurement was with a Vmax kinetic microtiter reader (Molecular Devices).

Construction and Recovery of rRSV Expressing mIFNγ.

Figure 1:
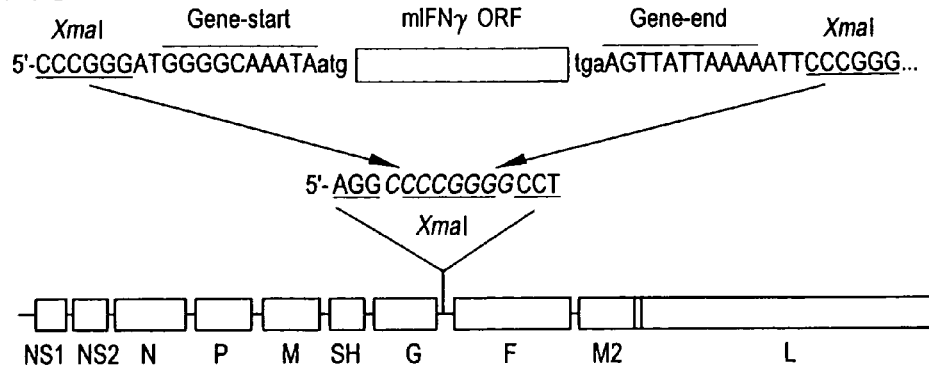
FIG. 1 illustrates construction of a recombinant RSV interferon gamma (rRSV/mIFNγ) chimeric genome modified to express murine IFNγ. The mIFNγ cDNA (shaded rectangle, with initiation and termination codons shown on either side in lower case) was modified to be flanked by RSV gene-start and gene-end signals as an XmaI fragment. This transcription cassette was inserted into an antigenome cDNA which had previously been modified by the insertion of an 8-nucleotide XmaI linker (bold, italicized) into the unique StuI site (the two halves of the StuI site, AGG and CCT, are underlined) present in the G-F intergenic region. XmaI sites are underlined.

A cDNA clone encoding mIFNγ was modified to be flanked by RSV gene-start and gene-end transcription signals (FIG. 1). This chimeric transcription cassette was inserted into the G-F intergenic region of the antigenome cDNA D46 which had been modified to contain a unique XmaI site 13. Bukreyev et al., *J. Virol.* 70, 6634-6641, 1996. The chimeric RSV antigenome RNA containing the mIFNγ insert would be 15,729 nucleotides in length and encode eleven mRNAs, with the mIFNγ gene being eighth in the 3' to 5' order. rRSV/mIFNγ was recovered from transfected cDNA as described previously, Collins et al., *Proc. Natl. Acad. Sci. USA* 92, 11563-11567, 1995.

rRSV/mIFNγ formed plaques which were comparable in size to those of a previously-described chimeric virus, rRSV/CAT (previously called D46/1024CAT), Bukreyev et al., *J. Virol.* 70, 6634-6641, 1996, which is identical to rRSV/mIFNγ except that its foreign gene encodes chloramphenicol acetyl transferase (CAT) rather than mIFNγ and its insert length is slightly greater (762 versus 507 nucleotides). The plaque size for each of these chimeric viruses was slightly smaller that of wt RSV, but otherwise the plaque morphology was indistinguishable.

Northern blot analysis (not shown) of poly($A^+$) mRNA isolated from cells infected with rRSV/mIFNγ or wt RSV demonstrated that the former expressed an mIFNγ mRNA of the expected size. Previously it has been shown that foreign sequences placed in nonsegmented negative stranded RNA viruses are remarkably stable in cell culture, Bukreyev et al., *J. Virol.* 70, 6634-6641, 1996; Schnell et al., *Proc. Natl. Acad. Sci. USA* 93, 11359-11365, 1996. Consistent with this, Northern blot and reverse transcription-PCR analysis of the mIFNγ gene during eight passages of rRSV/mIFNγ provided no evidence of deletion.

Growth of rRSV/mIFNγ and Production of mIFNγ In Vitro.

The growth characteristics of rRSV/mIFNγ, rRSV/CAT, and wt RSV were compared in HEp-2 cells (FIG. 2). rRSV/CAT was chosen as an additional control because it contained a similarly-sized insert in the same genome location. The two chimeric viruses grew more slowly and to a lower final titer than did wt RSV. For example, rRSV/mIFNγ achieved a peak titer of $10^{6.4}$ PFU (plaque forming units)/ml at 40 h post-infection, compared to a maximal titer of $10^{7.6}$ PFU/ml for wt RSV (48 h post-infection), indicating a 16-fold reduction.

The medium overlaying HEp-2 cells infected with rRSV/mIFNγ or rRSV/CAT was analyzed for mIFNγ at different times post-infection (FIG. 3). The concentration of mIFNγ was 0.1 ng/ml 8 h post-infection, the earliest time tested, 1.8 mg/ml at 40 h, and reached a maximum 4.4 mg/ml at 120 h, which corresponds to 22 mg per $10^6$ cells.

Replication, Immunogenicity, and Protective Efficacy of rRSV/mIFNγ in BALB/c Mice.

To evaluate replication of rRSV/mIFNγ in vivo, mice were infected intranasally with $10^6$ PFU of rRSV/mIFNγ, rRSV/CAT, or wt RSV. Animals were sacrificed on day 3, 4 or 5 post infection and the concentration of the virus in the upper (nasal turbinates) and lower (lungs) respiratory tract was determined by plaque assay. Replication of rRSV/mIFNγ was reduced relative to wt RSV by up to 63- and 20-fold in the upper and lower respiratory tracts, respectively (FIG. 4). In contrast, replication of rRSV/CAT was not significantly different from that of wt RSV, showing that the presence of an additional foreign gene of comparable size per se did not attenuate RSV replication in mice.

Serum samples were collected on days 0, 28 and 56 from mice infected with rRSV/mIFNγ, rRSV/CAT, or wt RSV and were analyzed by an RSV-specific and antibody isotype-specific ELISA and by an RSV neutralization assay (Table 1). The levels of IgA antibodies induced by the viruses were not significantly different. There was a significant increase (four fold) of the total IgG specific to RSV F protein in mice vaccinated with rRSV/mIFNγ compared to animals vaccinated with wt RSV or rRSV/CAT on day 56, but not on day 28. The titer of IgG1 antibodies was not significantly different between viruses on day 28, but on day 56 the mean titer of IgG1 from mice immunized with rRSV/mIFNγ was higher than that of mice immunized with wt RSV (reciprocal 12.1 $\log_2$ versus 9.3 $\log_2$; $p<0.05$) or rRSV/CAT. In contrast, the mean titer of IgG2a on day 56 was decreased for mice immunized with rRSV/mIFNγ compared with wt RSV (9.6 $\log_2$ versus 11.6 $\log_2$; $p<0.001$). Neutralizing antibody titers of mice infected with RSV/mIFNγ compared with wt RSV and rRSV/CAT were marginally lower on day 28 but were modestly higher on day 56 (12.3 versus 11.2, $\log_2$; $p<0.2$).

To evaluate protective efficacy, five mice from the groups described above were challenged on day 56 by the intranasal instillation of $10^6$ PFU per animal of wt RSV. Four days later, the mice were sacrificed and nasal turbinates and lungs were harvested for virus quantitation. Challenge virus was not detectable in animals which had been infected previously with rRSV/mIFNγ, and only a very low level of replication was observed in the upper respiratory tract in animals previously infected with wt RSV.

TABLE 1

RSV serum antibody titers (reciprocal mean $\log_2$ ± standard error) on days 0 (prior to immunization), 28 and 56[a]

| | Serum ELISA antibodies to RSV F protein | | | | | | | | | | | | RSV serum neutralizing antibodies | | |
|---|---|---|---|---|---|---|---|---|---|---|---|---|---|---|---|
| | IgA | | | IgG1 | | | IgG2A | | | Total IgG | | | | | |
| Virus | 0 | 28 | 56 | 0 | 28 | 56 | 0 | 28 | 56 | 0 | 28 | 56 | 0 | 28 | 56 |
| rRSV/mIFNγ | 7.3 | 10.8 ± 0.5[b] | 10.3 ± 0.6[b] | <5.3 | 7.3 ± 1.3[b] | 12.1 ± 1.0[c] | <5.3 | 10.8 ± 0.5 | 9.6 ± 0.3[d] | <5.3 | 11.3 ± 0.4 | 12.6 ± 0.6[e] | <3.3 | 9.1 ± 0.3[f] | 12.3 ± 0.6[f] |
| rRSV/CAT | 7.3 | 12.1 ± 0.7 | 7.3 ± 1.3 | <5.3 | 10.3 ± 0.5 | 6.3 ± 1.2 | <5.3 | 10.1 ± 0.4 | 10.1 ± 0.4 | <5.3 | 10.8 ± 0.3 | 10.3 ± 0.4 | <3.3 | 9.9 ± 1.2 | 11.7 ± 0.7 |
| wt RSV | 7.3 | 11.8 ± 0.8 | 9.1 ± 1.1 | <5.3 | 10.3 ± 1.2 | 9.3 ± 0.9 | <5.3 | 11.1 ± 0.3 | 11.6 ± 0.3 | <5.3 | 11.8 ± 0.3 | 10.6 ± 0.4 | <3.3 | 9.8 ± 0.3 | 11.2 ± 0.5 |
| Placebo | 7.3 | 7.8 ± 0.3 | 4.1 ± 0.4 | <5.3 | <5.3 | <5.3 | <5.3 | <5.3 | <5.3 | <5.3 | 7.32 ± 0.0 | <5.3 | <3.3 | <3.3 | <3.3 |

[a]Eight mice per group were used. Antibody titers on day 56 were determined in a separate assay.

[b]Difference relative to the wt RSV control is not statistically significant (Student's t-test) due to a high variability of individual samples.

[c,d,e,f]Statistical significance calculated by Student's t-test compared to wt RSV control: [c]$p < 0.05$; [d]$p < 0.001$; [e]$p < 0.02$; [f]$p < 0.2$.

Pulmonary Cytokine mRNAs.

The levels of mRNAs encoding selected cytokines were determined in the lungs of mice infected with rRSV/mIFNγ or wt RSV to determine if the level of mIFNγ mRNA synthesis was increased and if its synthesis affected the level of other Th1 or Th2 cytokine mRNAs. Five mice each from groups infected with rRSV/mIFNγ, wt RSV or placebo were sacrificed on days 1 and 4 after infection or days 1 and 4 after challenge with wt RSV on day 28 (days 29 and 32). Total lung RNA was isolated and analyzed for selected cytokine mRNAs by a commercial ribonuclease protection assay (FIG. 5). This direct assay reflects the concentration of an mRNA at the site of interest at a given time and precludes possible artifacts due to in vitro manipulation of harvested cells. The mRNA levels were determined for the Th1 marker cytokines IL-2 and IFNγ, the Th2 marker cytokines IL-4, IL-6 and IL-10, and the IL-12 p40 protein, which is the inducible component of the IL-12 heterodimer.

FIG. 5 shows an autoradiograph of an assay of IFNγ and IL-12 p40 mRNAs in lungs of five individual animals harvested 4 days after immunization with the indicated virus. Increased accumulation of mIFNγ was seen in the rRSV/mIFNγ-infected animals, and a slight, but statistically significant, increase in IL-12 p40 mRNA was seen in the rRSV/mIFNγ-infected animals compared to those infected with wt RSV. The results from this and other gels were quantitated with a phosphorimager and the mean value for each set of five mice was expressed as a percentage of the mouse L-32 housekeeping gene mRNA in the same gel lane (FIG. 6).

On day 1 or 4 post infection with wt RSV it was observed that: (i) the expression of the Th1 cytokine IFNγ mRNA, but not that of IL-2; (ii) an increase in the level of IL-12 p40 mRNA; and (iii) the expression of the Th2 cytokine IL-6 and IL-10 mRNAs. Infection with rRSV/mIFNγ induced a cytokine profile similar to that induced by wt RSV except that the levels of IFNγ mRNA were higher on both days 1 and 4, but especially so on day 4, and the level of IL-12 p40 mRNA also was higher on days 1 and 4. Thus, apart from the quantitative differences in IFNγ and IL-12 p40, wt RSV and rRSV/mIFNγ induced a similar profile of Th1 and Th2 cytokines. After virus challenge (days 29 and 32), the level of IFNγ, IL-2, IL-10, and IL-12 p40, but not IL-6, was also increased in mice immunized with wt RSV or with rRSV/mIFNγ compared to mock-immunized mice.

As an additional control, another group of animals in the same experiment was immunized parenterally with formalin-inactivated RSV (Connors et al., *J. Virol.* 66, 7444-7451, 1992) and subjected to the same harvest and challenge schedule. IL-4 mRNA was not detected in this or any other group following the initial immunization or infection. Upon challenge, IL-4 mRNA was greatly increased in the group which had received the formalin-treated vaccine, but was not detectable in the other groups.

The foregoing example details construction of a chimeric virus, rRSV/mIFNγ, that expresses the mIFNγ gene as a separate mRNA from an additional transcriptional unit placed eighth in the gene order, between the G and F genes. This virus directed the synthesis of high levels of mIFNv in cell culture. Growth of rRSV/mIFNγ in cell culture was reduced 16-fold compared to wt RSV. However, the magnitude of this effect was comparable to that observed for rRSV/CAT, which contains the CAT gene in the same genome location. Thus, the growth restriction in vitro to the is specified by presence of the foreign gene rather than by virtue of the activity its encoded product. That the expression of mIFNγ did not inhibit viral growth in human HEp-2 cells is not surprising since human IFNγ and mIFNγ share only 40% amino acid sequence identity.

Replication of rRSV/mIFNγ in BALB/c mice was reduced 63- and 20-fold in the upper and lower respiratory tract, respectively, compared to wt RSV. In contrast, rRSV/CAT assayed in parallel was not restricted compared to wt RSV, indicating that the attenuation of rRSV/mIFNγ in vivo was not due to the presence of the additional gene per se, but rather was a consequence of expression of mIFNγ. Since the growth restriction in vivo operated early in infection, it seems likely that it was due to effects of the expressed mIFNγ on innate immunity, such as induction of oligoadenylate synthetase and the resulting antiviral cascade or possibly the activation of NK cells and macrophages, rather than to effects on adaptive immunity. That the growth of rRSV/mIFNγ was restricted only 63-fold or less suggests that IFNγ is not the major effector of resistance to RSV. For another respiratory virus, influenza A virus, expression of IFNγ by the host was not needed for an efficient immune response, although its absence resulted in a Th2-biased antibody and cytokine response (Graham et al., *J. Exp. Med.* 178, 1725-1732, 1993).

The question of whether the coexpression of IFNγ during RSV infection could further bias T cell proliferation in favor of a Th1 response was addressed by analyzing the pattern of cytokine mRNA and RSV-specific antibody isotypes. Infection with wt RSV was associated with increases in mRNA for the Th1 marker IFNγ but not IL-2, for the Th2 markers IL-6 and IL-10, and for IL-12 p40, which is produced primarily by monocytes and macrophages. Infection with rRSV/mIFNγ resulted in an increased level of IFNγ mRNA and a slightly increased (less than two-fold) level of IL-12 p40 mRNA over that observed with wt RSV. The increase in mIFNγ mRNA presumably was due at least in part to that expressed by the recombinant virus. The increase in the IL-12 p40 mRNA probably was a result of IFNγ-mediated activation of its monocyte/macrophage source, although this was not observed previously in vitro (D'Andrea et al., *J. Exp. Med.* 176, 1387-1398, 1992).

Animals infected with rRSV/mIFNγ did not exhibit differences from wt RSV in the level of mRNAs for the other Th1 marker, IL-2, or for the Th2 markers IL-6 or IL-10. There were modest increases in total IgG and IgG1 RSV-specific antibodies in mice immunized with rRSV/mIFNγ compared to wt RSV, with the latter antibodies being a marker for a Th2 response (Snapper et al., *Fundamental Immunology*, ed. Paul, W. E. (Raven Press, New York), pp. 837-863, 1993). There also was a modest decrease in IgG2a, a marker for a Th1 response (Snapper et al., *Fundamental Immunology*, ed. Paul, W. E. (Raven Press, New York), pp. 837-863, 1993). Thus, neither the cytokine nor the antibody response was consistent with an increased bias towards Th1 markers either upon the initial infection with rRSV/mIFNγ or following challenge with wt RSV.

Mice immunized with wt RSV or rRSV/mIFNγ were highly resistant to RSV challenge. Despite its growth restriction in vivo, rRSV/mIFNγ induced titers of total IgG against RSV F protein and RSV-neutralizing serum antibodies which were higher than that induced by wt RSV. Previous studies (Crowe et al., *Vaccine* 12, 783-790, 1994) showed that chimpanzees vaccinated with RSV cpts248/404, a candidate live-attenuated virus vaccine, developed lower titers of RSV-neutralizing antibodies compared to wt RSV-immunized animals (7.9 $\log_2$ versus 11.1 $\log_2$, a 9.2-fold difference), suggesting a correlation between the level of RSV replication and its immunogenicity. That the antibody response to rRSV/IFNγ was moderately increased overall despite its reduced level of virus replication marks a highly desirable phenotype for developing a live-attenuated RSV vaccine.

Rodents such as mice or cotton rats mount extremely efficient immune responses to RSV antigens (Collins et al., Vaccine 8, 164-168, 1990), whereas immunogenicity is usually much less when evaluated in nonhuman primates or human volunteers. This might be especially important for young infants, whose antibody response to RSV has been shown to be reduced (Murphy et al., J. Clin. Microbiol. 24, 894-898, 1986). Thus, differences in antigenicity which could be very significant in humans are often not detected in rodents because of their greater immuno-responsiveness to RSV antigen. Furthermore, replication of RSV in rodents is very restricted, such that only a small percentage of pulmonary cells are infected and disease typically does not occur. It is very likely that the effect of IFNγ on attenuation, immunogenicity, or reactogenicity will be greater in a fully permissive host. To evaluate this, the invention provides for construction of recombinant RSVs that express human rather than murine IFNγ. Evaluation of this virus in chimpanzees, which is the animal that most resembles humans with regard to RSV replication, disease and immunogenicity will allow for adjustment of attenuation and other features of candidate vaccines. One possible complication, namely that expression of the human cytokine in infected cultured primate cells may hinder the preparation of vaccine lots, can be obviated by using cells from a different species.

As noted above, a number of cytokine genes have been inserted into recombinant DNA viruses, mostly vaccinia virus, revealing effects on attenuation, pathogenicity, and immunogenicity (Ramshaw et al., Nature 329, 545-546, 1987; Flexner et al., Nature 330, 259-262, 1987; Rolf et al., Curr. Opin. Immunol. 9, 517-524, 1997, for review, see Rolf et al., Curr. Opin. Immunol. 9, 517-524, 1997). In a poxvirus, expression of IFNγ or type 1 IFN attenuated the virus for the host, but this attenuation was accompanied by a decreased humoral immune response (Leong et al., J. Virol. 68, 8125-8130, 1994; Bembridge et al., J. Virol. 72, 4080-4087, 1998; Karaca et al., Vaccine 16, 1496-1503, 1998). Expression of IFNγ by a simian immunodeficiency virus (SIV) lacking the nef gene resulted in further attenuation of the SIV mutant for monkeys, but the cytokine insert was very unstable after several weeks of replication, and the attenuation was accompanied by a decrease in the humoral immune response to SIV glycoprotein (Giavedoni et al., J. Virol. 71, 866-872, 1997). The present invention extends this strategy to provide vaccines against a negative-stranded virus. The results presented herein demonstrate that it is possible to attenuate the virus even while maintaining immunogenicity, a result previously attained only in the distinct case of expression of IL-2 by a vaccinia virus vector (Flexner et al., Vaccine 8, 17-21, 1990). Thus, the coexpression of IFNγ in recombinant RSV represents a new type of attenuation of nonsegmented negative stranded RNA viruses, one which reduces virus growth without compromising immunogenicity.

EXAMPLE II

Construction and Characterization of Recombinant RSV Encoding Murine IL-2

In the present example, a recombinant RSV was constructed containing the coding sequence of murine interleukin-2 (mIL-2) in a transcription cassette inserted into the G-F intergenic region. The recovered virus (rRSV/mIL-2) expressed high levels (up to 2.8 μg/ml) of mIL-2 in cell culture. Replication of rRSV/mIL-2 in vitro was reduced up to 13.6-fold compared to wild type (wt) recombinant RSV (rRSV), an effect that was due to the presence of the foreign insert but was not specific to mIL-2. Replication of the rRSV/mIL-2 virus in the upper and lower respiratory tracts of BALB/c mice was reduced up to 6.3-fold, an effect that was specific to mIL-2. The antibody response, including the levels of RSV-specific serum IgG1, IgG2a, IgA, and total IgG, and the level of protective efficacy against wt RSV challenge were not significantly different from those of wt rRSV. Analysis of total pulmonary cytokine mRNA isolated 1 and 4 days following infection with rRSV/mIL-2 revealed elevated levels of mRNA for IL-2, IFNγ, IL-4, IL-5, IL-6, IL-10, IL-13 and IL-12 p40, compared to wt rRSV. Flow cytometry of total pulmonary mononuclear cells isolated 10 days following infection with rRSV/mIL-2 revealed increased levels of CD4+ T lymphocytes separately expressing IFNγ or IL-4, compared to wt rRSV. These elevations in cytokine mRNA or cytokine-expressing CD4+ cells relative to wt rRSV-primed animals were not observed following challenge with wt RSV on day 28. Thus, the expression of mIL-2 by recombinant RSV was associated with a modest attenuation of virus growth in vivo, induction of serum antibodies at levels comparable to wt rRSV, and transient increases in both the Th1 and Th2 CD4+ lymphocytes and cytokine mRNAs compared to wt rRSV.

IL-2 is one of the prototype cytokines known formerly as a "T-cell growth factor". It is produced by Th1 and Th2 CD4+ cells (Th1 produce a higher level) as well as by CD8+ cells upon stimulation with antigen or mitogen (Gaffen et al., The Cytokine Handbook, A. W. Thomson (ed.), p 73-103, Academic Press, 1998; and Thorpe, Cytokines, A. Mire-Sluis and R. Thore (eds.), p 19-33, 1998). Human IL-2 protein is synthesized as a precursor that is 153 amino acids long and is processed, by cleavage of a 20-amino acid signal peptide, into a mature protein of 133 amino acids. Its murine analog has a similar size and share 63% amino acid similarity (Kashima et al., Nature 313: 402-4, 1985; Yokota et al., Proc. Natl. Acad. Sci. USA 82:68-72, 1985, each incorporated herein by reference). Naive T cells express a low-affinity receptor for IL-2 consisting of β and γ chains; association with the α chain modifies it to be a high-affinity receptor. Upon binding of IL-2, the receptor triggers activation of numerous transcription factors by JAK1 kinase associated with the receptor.

The regulatory network of IL-2 is very complex. IL-2 has pleiotropic biological effects, limited chiefly but not exclusively to leukocytes. IL-2 stimulates dramatic growth and proliferation of activated T cells and, at high concentrations, can cause proliferation of resting T cells. Il-2 stimulates T cell cytolytic activity. It also stimulates proliferation of activated B cells and promotes induction of immunoglobulin secretion. IL-2 stimulates activity of natural killer (NK cells) and lymphocyte-activated killer (LAK) cells. It also promotes proliferation and differentiation of monocytes. Chemokine receptors CCR1, CCR2, and CCR5 are induced by IL-2. IL-2 has been used to treat certain viral infections, including hepatitis B virus, human immunodeficiency virus and, herpes simplex virus (Gaffen et al., The Cytokine Handbook, A. W. Thomson (ed.), p 73-103, Academic Press, 1998; and Thorpe, Cytokines, A. Mire-Sluis and R. Thore (eds.), p 19-33, 1998). IL-2 administered to AIDS patients induced substantial and sustained increases in CD4+ cells (Kovacs et al. New Eng. J. Med. 335: 1350-1356, 1996, incorporated herein by reference).

The present example demonstrates construction and evaluation of a recombinant RSV modified to contain the gene encoding murine interleukin-2 (mIL-2) flanked with RSV-specific gene-start (GS) and gene-end (GE) transcription signals. FIG. 7 illustrates a map of the genome of rRSV/mIL-2. Plasmid containing a cDNA copy of the murine IL-2 gene was linearized and amplified by PCR with the primers TATACCCGGGAT GGGGCAAATATGTACAGCATGCAGCTCGC (SEQ ID NO. 3) (XmaI restriction endonuclease site is shown in italics, RSV gene-start sequence is underlined, IL-2 translation initiation codon is bolded) and ATTACCCGGGAA TTTTTAATAACTTTATTGAGGGCTTGTTGAGA (SEQ ID NO. 4) (XmaI restriction endonuclease site is shown in italics, RSV gene-end sequence complement is underlined, IL-2 translation termination codon complement is in bold). Naturally-occurring IL-2 mRNA contains an "instability sequence" within the 3'-nontranslated region of the mRNA which mediates regulation at the post-transcriptional level. The IL-2 cDNA for insertion into rRSV was specifically designed to lack this sequence. The amplified fragment was digested with XmaI restriction endonuclease, purified by agarose gel electrophoresis, cloned in the XmaI site of plasmid pUC 19, and sequenced completely to confirm the correct primary structure. The plasmid was digested with XmaI and the insert was purified and cloned into the unique XmaI site of the previously-described RSV antigenomic plasmid D46/1024 (Bukreyev et al., *J. Virol.* 70:6634-41, 1996) which encodes an RSV antigenome of 15,231 nt long with the XmaI linker inserted into G-F intergenic region. The RSV/mIL-2 antigenomic plasmid would encode an antigenomic RNA of 15,772 nucleotides, 549-550 nucleotides longer than the 15,222- and 15,223-nucleotide antigenomes of biologically-derived and recombinant RSV, respectively.

The antigenomic plasmid was used to direct the recovery of recombinant virus recovery as described previously (Collins et al., *Proc. Natl. Acad. Sci. USA,* 92:11563-11567, 1995, incorporated herein by reference). The virus was passaged in HEp-2 cells and quantitated by plaque assay was described earlier (Murphy et al., *Vaccine,* 8:497-502, 1990). The rRSV/mIL-2 virus formed plaques which were slightly smaller than those of wild type RSV, but otherwise were indistinguishable with regard to morphology. The slightly-diminished size of the rRSV/mIL-2 viral plaques was comparable to that of the previously described rRSV/CAT and rRSV/mIFNγ plaques (Bukreyev et al., *J. Virol.* 70:6634-6641, 1996, and *Proc. Natl. Acad. Sci. USA* 96:2367-2372, 1999, each incorporated herein by reference).

The IL-2-containing virus (rRSV/mIL-2) was found to express high levels (up to 2.8 micrograms/ml) of IL-2 in the medium of infected tissue culture cells. This corresponded to 14 micrograms of IL-2 per $10^6$ cells, which is comparable to the yield of 22 micrograms of IFNγ per $10^6$ cells obtained with the rRSV/mIFNγ virus (Bukreyev et al. *Proc. Natl. Acad. Sci. USA* 96:2367-2372, 1999).

To examine the kinetics of growth of the rRSV/mIL-2 virus, HEp-2 cells were infected at a moi of 2 pfu per cell with this recombinant or with wild type RSV. Aliquots of medium were taken at 8 h time points, frozen, and analyzed later by plaque assay. The rRSV/mIL-2 virus was found to be attenuated for growth in HEp-2 cells, with the maximum yield being approximately 14- to 17-fold lower than that of wild type. This level of attenuation is very similar to that observed for rRSV containing either the CAT gene or the mIFNγ gene in the same antigenome location (Bukreyev et al., *J. Virol.* 70:6634-6641, 1996, and *Proc. Natl. Acad. Sci. USA* 96:2367-2372, 1999, each incorporated herein by reference). Hence, this effect of attenuation in cell culture appears to be due to the presence of the insert but was independent of the nature of the insert. It is not surprising that mIL-2 and mIFNγ do not have a biological effect in vitro in HEp-2 cells, since the cytokines are of murine origin and the cells of human origin.

Northern blot hybridization was used to analyze transcription of the foreign mIL-2 gene, as well as the G, F and L genes. HEp-2 cells were infected with rRSV/mIL-2 or wt RSV, and after 5 days the cells were harvested, total RNA was purified, and the poly(A)$^+$ fraction was isolated. Northern blot analysis confirmed that the rRSV/IL-2 virus directed the expression of mIL-2 mRNA as well as of minor species which were of the appropriate sizes to be IL-2-G and F-IL-2 bicistronic mRNAs derived by transcriptional readthrough of adjoining genes. The identifications of these bicistronic mRNAs were confirmed by hybridization with the F and G probes. Hybridization with the F, G and L probes showed that both viruses expressed these mRNAs, as would be expected.

The stability of the foreign gene was analyzed. The rRSV/mIL-2 virus was subjected to 8 passages in HEp-2 cells. Total cellular RNA from passage 8 was isolated, and RT-PCR was performed using the direct and reverse primers corresponding to the fragments of the genome located upstream and downstream of the site of insertion (G and F gene), respectively. This resulted in the production of a single detectable PCR product corresponding to the predicted length of 867 nucleotides, and there were no detectable PCR products of shorter length which might reflect partial or complete deletion of the insert. This is consistent with previous findings that each of 25 rRSV/CAT plaque isolates recovered following 8 passages retained the CAT gene in a form capable of expressing enzymatically-active CAT (Bukreyev et al., *J. Virol.* 70:6640-6641, 1996, incorporated herein by reference).

To quantitate the expression of mIL-2, HEp-2 cells were infected with rRSV/mIL-2 (passage 8) at an MOI of 2 PFU per cell and aliquots of harvested medium were assayed by ELISA using the Quantikine M Mouse IL-2 Immunoassay (R&D systems). The concentration of secreted mIL-2 was 1.7 ng/ml at 8 hours post-infection and increased more than 1000-fold to a maximum of 2.8 μg/ml at 120 h post-infection.

Replication of the rRSV/IL-2 virus was evaluated in BALB/c mice. Mice were inoculated intranasally on day 0 with $10^6$ PFU of rRSV/mIL-2, rRSV/CAT, or wt RSV in a 0.1 ml inoculum, or mock-infected with 0.1 ml of Opti-MEM medium. Five mice from each group were sacrificed on days 3, 4 and 5 and nasal turbinates and lung tissues were harvested and assayed for infectious RSV by plaque assay of the diluted tissue extracts (Murphy et al., *Vaccine* 8:497-502, 1990, incorporated herein by reference). Compared to wild type RSV, replication of the rRSV/mIL-2 virus was found to be attenuated in a moderate but statistically significantly fashion in both the upper and lower respiratory tracts, with the sole exception being that the titer in the nasal turbinates on day 5 was not significantly different from that of wild type RSV (FIG. 8). The maximum difference in replication was 5-fold and 6.3-fold, on day 3 in the upper respiratory tract and day 5 in the lungs, respectively. In contrast, the rRSV/CAT was not significantly different than wild type RSV except on day 3 in the lungs, where it was comparable to rRSV/mIL-2. The one exception was that, in the lungs on day 3, the titer of RSV/CAT was reduced compared to wt rRSV and was similar to that of rRSV/mIL2.

The rRSV/CAT virus contains a genome of 15,984 nucleotides, compared to 15,222 nucleotides for the wild type RSV and 15,772 for the rRSV/IL-2 virus. Thus, the close correspondence between the titers of rRSV/CAT and wild type RSV indicates that the presence of an insert alone does not significantly attenuate RSV in mice, at least for inserts in this size range. Similar findings were reported in previous work (Bukreyev et al., *Proc. Natl. Acad. Sci. USA* 96:2367-2372, 1999, incorporated herein by reference). In contrast, the titer of rRSV/IL-2 was significantly reduced in five of the six in vivo samples. Hence, the attenuation of rRSV/IL2 bearing the 549 nucleotide inserted mIL 2 gene at the same genome position appeared to be specific to mIL 2.

To evaluate the immunogenicity of rRSV/mIL-2, mice were infected with rRSV/mIL-2, rRSV/CAT or wt rRSV as described above, and serum samples were taken on days 0 (immediately before infection), 28 and 56 (Table 2). Each of the viruses induced a high titer of RSV-neutralizing serum antibodies, and the three viruses were indistinguishable on this basis. In addition, there were no significant differences between the three viruses with regard to the induction of RSV-specific serum IgA, IgG1, IgG2a, and total IgG, as determined by ELISA with purified RSV F protein as antigen (Table 2). The mice in each group were then challenged on day 56 by the intranasal inoculation of $10^6$ PFU of wt RSV per animal. Four days later, on day 60, the mice were sacrificed and virus titers in the upper and lower respiratory tract were determined. All of the previously-infected animals exhibited a high level of resistance to challenge virus replication. Replication of the challenge virus was undetectable in animals which had been previously infected with rRSV/CAT or rRSV/mIL-2 (mean titers of <2.0 $log_{10}$ PFU/g in the nasal turbinates and <1.7 $log_{10}$ PFU/g in the lungs), whereas a low level of RSV was detected in animals which had been immunized with wt rRSV (mean titers of 2.3 $log_{10}$ PFU/g in the nasal turbinates and <1.7 $log_{10}$ PFU/g in the lungs). In contrast, animals which had not been previously infected had mean titers of 4.7 $log_{10}$ PFU/g in the nasal turbinates and lungs. Thus, the three viruses were indistinguishable with regard to the ability to induce a high level of resistance to reinfection.

The levels of pulmonary mRNAs for selected cytokines were measured in mice following infection with $10^6$ PFU of rRSV/mIL-2 or wt rRSV, or mock-infection. This assay has the advantage that it does not require in vitro stimulation or manipulation of cells, and measures the aggregate response of all pulmonary cells. 4 or 5 mice from each group were sacrificed and lungs harvested on days 1 and 4 post-infection. These days were chosen because they coincide with the period of active RSV replication, and abundant expression of cytokine mRNA had been demonstrated in this time period (Graham et al., *J. Immunol.* 151:2032-2040, 1993, incorporated herein by reference). Total lung RNA was isolated and analyzed by an RNAse protection assay, using previously described methods (Bukreyev et al., *Proc. Natl. Acad. Sci. USA*. 96:2367-2372, 1999, incorporated herein by reference). RNA from each individual animal was assayed separately. The cytokine-specific gel bands displayed on sequencing gels were quantitated by phosphorimagery, and the amount of each band for each mouse was expressed as a percentage of the L-32 housekeeping gene mRNA from the same gel lane for the same mouse. Then, the mean value and standard deviation for each group of mice were determined (FIG. 9).

TABLE 2

RSV serum antibody response to infection with rRSV/mIL-2[a]

| | Serum ELISA antibody titer(reciprocal mean $log_2$ ± SE) to RSV F protein[b] | | | | | | | | | | | | RSV serum neutralizing antibodies[c] | | |
|---|---|---|---|---|---|---|---|---|---|---|---|---|---|---|---|
| | IgA | | | IgG1 | | | IgG2A | | | Total IgG | | | | | |
| Virus | 0 | 28 | 56 | 0 | 28 | 56 | 0 | 28 | 56 | 0 | 28 | 56 | 0 | 28 | 56 |
| rRSV/mIL-2 | 7.3 | 10.6 ± 0.7 | 9.6 ± 1.1 | <5.3 | 9.6 ± 0.5 | 8.8 ± 1.4 | <5.3 | 10.6 ± 0.5 | 10.3 ± 0.4 | <5.3 | 10.8 ± 0.6 | 11.1 ± 0.3 | <3.3 | 9.9 ± 0.1 | 11.3 ± 0.4 |
| rRSV-CAT | 7.3 | 12.1 ± 0.7 | 7.3 ± 1.3 | <5.3 | 11.3 ± 0.5 | 7.8 ± 1.1 | <5.3 | 10.1 ± 0.4 | 10.1 ± 0.4 | <5.3 | 10.8 ± 0.3 | 10.3 ± 0.4 | <3.3 | 9.9 ± 1.2 | 11.7 ± 0.7 |
| wt RSV | 7.3 | 11.8 ± 0.8 | 9.1 ± 1.1 | <5.3 | 10.8 ± 1.2 | 10.1 ± 0.6 | <5.3 | 11.1 ± 0.3 | 11.6 ± 0.3 | <5.3 | 11.8 ± 0.3 | 10.6 ± 0.4 | <3.3 | 9.8 ± 0.3 | 11.2 ± 0.5 |
| Mock | 7.3 | 7.8 ± 0.3 | 4.1 ± 0.4 | <5.3 | <5.3 | <5.3 | <5.3 | <5.3 | <5.3 | <5.3 | 7.32 ± 0.0 | <5.3 | <3.3 | <3.3 | <3.3 |

[a]Eight mice per group were infected on day 0 with $10^6$ PFU per animal of the indicated virus in a 0.1 ml inoculum. Antibody titers on day 56 were determined in a separate assay.
[b]The titer of isotype-specific serum ELISA antibodies specific to the RSV F protein was determined as described (Bukreyev et al., Proc. Natl. Acad. Sci. USA. 96: 2367-2372, 1999).
[c]RSV-neutralizing serum antibodies were measured by a complement-enhanced 60% plaque-reduction assay (Crowe et al., Vaccine 11: 1395-1404, 1993).

This analysis showed that infection with wt rRSV stimulated the abundant accumulation of mRNA for the Th1 cytokine IFNγ and the Th2 cytokine IL-6, and also stimulated the accumulation mRNA for IL-12 p40, which is the inducible subunit of the IL-12 heterodimer. IL-12 is produced by monocytes and macrophages, among other cells, but not by T lymphocytes, and its production is enhanced by IFNγ. These three abundant mRNAs also were observed in rRSV/IL-2-infected mice, and accumulated to somewhat higher levels than with wt rRSV. Infection with rRSV/mIL-2 also resulted in the accumulation of IL-2 mRNA, which was not observed in wt rRSV-infected animals and likely was encoded directly by the virus. Infection with rRSV/mIL-2, but not wt rRSV, also stimulated the accumulation of several less abundant Th2 cytokine mRNAs, namely IL-4, IL-5, IL-10 and IL-13. Thus, coexpression of IL-2 from recombinant RSV was associated with an increase in the accumulation of mRNAs for both Th1 and Th2 marker cytokines.

Mice from each of the same groups were challenged with wt RSV on day 28, and lungs were harvested for analysis on days 29 and 32 (1 or 4 days post-challenge). Mice that had been infected with wt rRSV and challenged 28 days later with wt RSV exhibited elevated levels of mRNAs for IL-6, IFNγ and IL-12 p40, and to a lesser extent elevated amounts of mRNAs for IL-2 and IL-10, whereas mRNAs for IL-4, IL-5 and IL-13 were not detected. Mice that had been infected with rRSV/mIL-2 and challenged with wt RSV exhibited the same pattern with one exception: with regard to IL-12 p40 mRNA, there was no significant difference on day 29, but on day 32 the rRSV/mIL-2-primed group had a small decrease (32%, P<0.01) compared to the wt rRSV-primed group.

Also examined was the total pulmonary CD4+ T lymphocyte response to rRSV/mIL-2 versus wt rRSV. Specifically, intracellular cytokine immunostaining and flow cytometry was used to quantitate pulmonary CD4+ lymphocytes expressing the Th1 marker IFNγ or the Th2 marker IL-4 (Hussell et al., *J. Gen. Virol.* 77:2447-2455, 1996; Openshaw et al., *J. Exp. Med.* 182:1357-1367, 1995; Prussin et al., *J. Immunol. Methods* 188:117-128, 1995; each incorporated herein by reference). Mice were infected with $10^6$ PFU of rRSV/mIL-2 or wt rRSV, or were mock-infected. 4 animals from each group were sacrificed each on days 4 and 10, and lungs were harvested and processed as described below. The remaining mice in each group were challenged intranasally on day 28 with $10^6$ PFU of wt RSV, and 4 mice from each group were sacrificed 4 and 10 days later (days 32 and 38) and their lungs were harvested and processed. The lungs were minced and digested with DNAse I and collagenase, and total pulmonary mononuclear cells were isolated by centrifugation and banding in Ficoll-Paque Plus medium (Amersham Pharmacia Biotech), with material from each animal processed separately. The cells were stimulated in vitro by incubation at 37° C. for 4 h with nonspecific mitogen (2.5 ng/ml phorbol 12-myristate 13-acetate and 250 ng/ml ionomycin) in the presence of monensin, which blocks exocytosis and causes cytokines to accumulate intracellularly. Fc receptors were blocked by preincubating cells with purified rat anti-mouse CD16/CD32 (FcγIII/II receptor) for 15 min at 4° C. The cells were fixed with paraformaldehyde solution (Cytofix Buffer, PharMingen, 20 min at 4° C.), permeabilized (PermWash, PharMingen, 20 min at 4° C.) and stained for CD4+ (Tri-Color conjugated rat IgG2a clone CT-CD4, Caltag Laboratories), IFNγ (FITC-conjugated rat IgG1 clone XMG1.2, PharMingen), and IL-4 (R-PE-conjugated rat IgG2b clone BVD4-ID11, PharMingen) molecules. The immunostaining was for 30 min at 4° C. in the dark using a pre-optimized amount of each labeled antibody. The specificity of staining was confirmed with controls in which (i) reactivity was blocked by preincubation for 30 min at 4° C. with an unconjugated preparation of the same antibody, and (ii) reactivity was lost when the primary antibody was replaced with one of the same isotype but having a heterologous specificity. Published work indicated that the in vitro stimulation step does not alter the pattern of cytokine expression (Hussell et al., *J. Gen. Virol.* 77:2447-2455, 1996, incorporated herein by reference). The lymphocyte fraction was gated as described (Hussell. et al., 1996, supra) and analyzed by three-color flow cytometry using a FACSCalibur flow cytometer (Becton Dickinson). Approximately 60,000 gated lymphocytes were analyzed per sample. It is noteworthy that total pulmonary lymphocytes were examined, rather than a subpopulation such as isolated by lavage.

Approximately half of the total pulmonary mononuclear cells gated as lymphocytes, and this percentage was not significantly altered in response to a primary infection or challenge with either rRSV/mIL-2 or wt rRSV, compared to uninfected controls. The percentage of the mononuclear cells identified as CD4+ lymphocytes was essentially unchanged following the initial infection with either virus (mean percentages of 7.6 and 7.9 on days 4 and 10, respectively, for wt rRSV; 7.5 and 10.7 on days 4 and 10, respectively, for rRSV/mIL-2), compared to the uninfected controls (mean percentages of 9.0 and 7.2 on days 4 and 10, respectively). However, that percentage was nearly doubled on days 32 and 38 following the challenge (mean percentages of 18.2 and 15.4 on days 32 and 38, respectively, for wt rRSV; 15.7 and 14 on days 32 and 38, respectively, for rRSV/mIL-2), compared to the uninfected control (as above). This is indicative of a strong secondary immune response despite the very restricted replication of the challenge virus. The CD4+ population was then examined for expression of IFNγ versus IL-4. FIG. 10 shows examples of data for three individual animals that were infected with rRSV/mIL-2, wt rRSV, or were mock-treated, and were analyzed on day 10. The complete experiment is summarized in Table 3.

TABLE 3

Flow cytometric analysis of pulmonary CD4+ lymphocytes expressing IFNγ, IL-4, or both from mice infected with wt RSV or rRSV/mIL-2[a]

| Virus | Day 4 | | | Day 10 | | | Day 32 | | | Day 38 | | |
|---|---|---|---|---|---|---|---|---|---|---|---|---|
| | IFNγ+ | IL-4+ | Dbl+ | IFNγ+ | IL-4+ | Dbl+ | IFNγ+ | IL-4+ | Dbl+ | IFNγ+ | IL-4+ | Dbl+ |
| rRSV/mIL-2 | 3.3 ± 0.32 | 0.99 ± 0.21 | 0.20 ± 0.06 | 838 ± 1.10[b] | 2.4 ± 0.09[c] | 0.61 ± 0.01[c] | 1.3 ± 0.34 | 0.78 ± 0.12 | 0.04 ± 0.02 | 20 ± 3.83 | 0.56 ± 0.07 | 0.22 ± 0.06 |
| wt rRSV | 2.7 ± 0.66 | 0.95 ± 0.28 | 0.14 ± 0.05 | 4.2 ± 1.11 | 0.65 ± 0.18 | 0.15 ± 0.06 | 4.1 ± 0.66 | 1.1 ± 0.28 | 0.09 ± 0.04 | 19.3 ± 1.35 | 0.43 ± 0.05 | 0.14 ± 0.00 |
| Mock | 0.48 ± 0.03 | 0.28 ± 0.00 | 0.03 ± 0.00 | 1.7 ± 0.25 | 1.1 ± 0.21 | 0.31 ± 0.10 | ND | ND | ND | 5.8 ± 0.10[d] | 0.70 ± 0.14[d] | 0.10 ± 0.02[d] |

[a]Mice were infected intranasally on day 0 with $10^6$ PFU per animal of the indicated virus, or were mock-infected. Animals from each group were sacrificed on days 4 and 10, as indicated. The remaining animals (including the mock-infected group) were challenged on day 28 with $10^6$ PFU of wt RSV per animal, and the animals were sacrificed on days 32 and 38, (4 and 10 days post-challenge) as indicated. Total pulmonary mononuclear cells were analyzed by flow cytometry using immunostaining for CD4, IFNγ and IL-4. Values are expressed as the percentage of CD4+ lymphocytes. Each group contained 4 mice per day with the following exceptions: the wt RSV group on day 4 has 3 animals; the mock-infected group on day 4 had 2 animals, and the mock-infected group on days 10 and 38 had 3 animals each. The cells of each animal were processed separately, and each group is expressed as the mean of the individual data for the 2-4 mice with the SE indicated.
[b,c]Statistical significance calculated by Student's t-test compared to wt rRSV control: [b]$p < 0.005$; [c]$p < 0.001$.
[d]Note that the animals in the Mock group were mock-infected on day 0, but received the RSV challenge on day 28. Hence, the day 38 point corresponds to the day 10 point for the wt RSV group.

Figure 9:
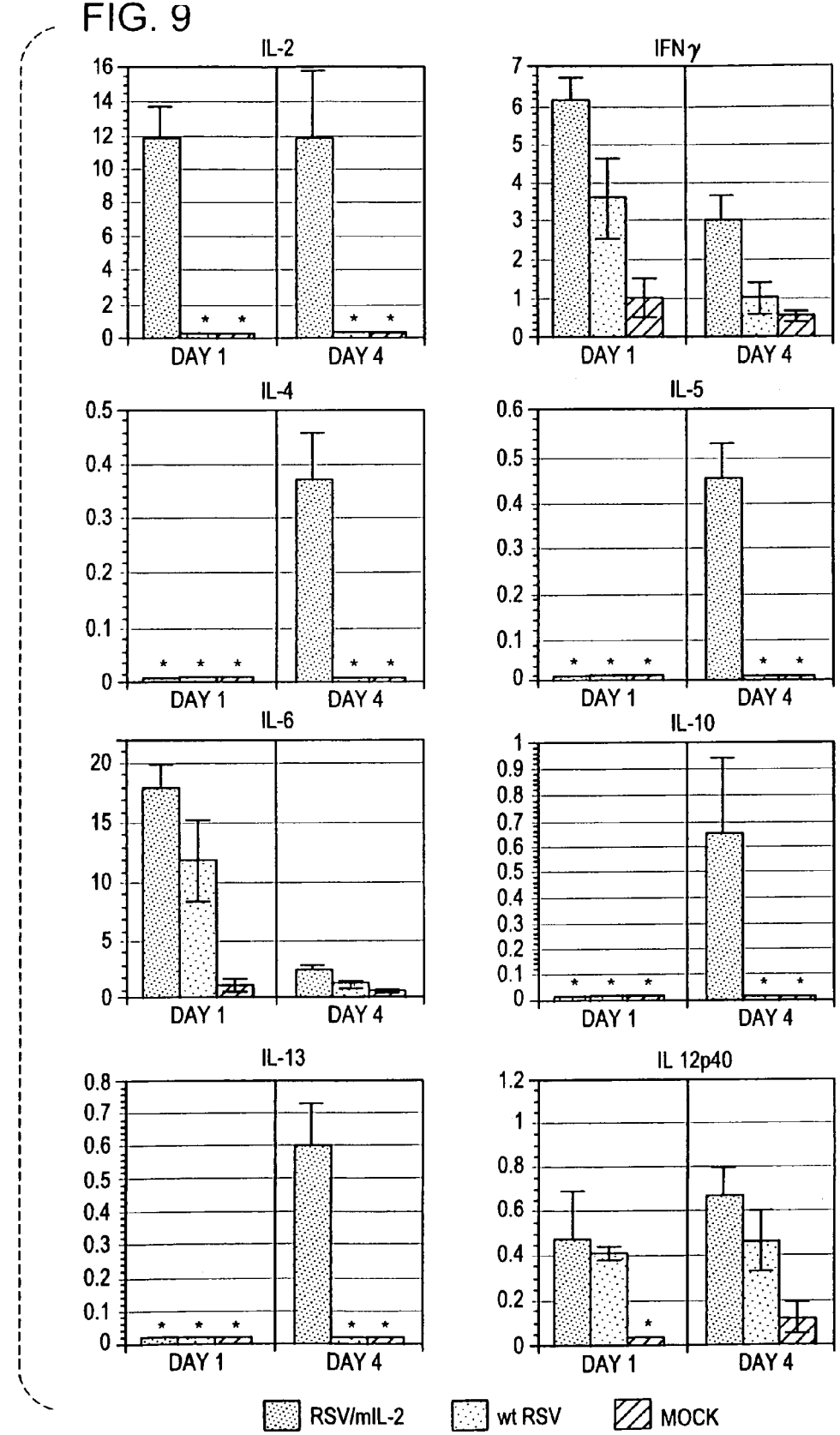

On day 4 following the initial infection, animals which received rRSV/mIL-2 or wt rRSV exhibited increased levels of CD4+ lymphocytes which were IFNγ-positive, IL-4-positive, or double-positive, but the magnitude of the response was very similar for the two viruses. On day 10, the average number of the cells which were IFNγ-positive, IL-4-positive, or double-positive was statistically significantly increased in rRSV/mIL-2-infected mice compared to wt rRSV-infected mice:2.1-fold ($P<0.05$), 3.6-fold ($P<0.001$), and 4.1-fold ($P<0.001$), respectively. Thus, the increase in Th1 and Th2 cytokine mRNAs noted above on day 4 (FIG. 9) was reflected by cytokine synthesis by CD4+ lymphocytes on day 10 but not day 4. This delay might reflect lower sensitivity for the latter assay, or a lag in expression, or, in the case of IFNγ, synthesis by a source other than CD4+ lymphocytes such as NK cells (Hussell et al., *J Gen Virol.* 79:2593-2601, 1998, incorporated herein by reference).

When animals were challenged on day 28 and pulmonary CD4+ cells examined on day 32, the amount of IFNγ-positive cells in animals which had been primed with rRSV/mIL-2 was 3-fold lower compared to wt rRSV-immunized mice (P<0.001). The percentages of IL-4-positive and double-positive cells were similar in the both groups of mice. The observed reduction in IFNγ-expressing CD4+ cells was not reflected in the amount of total pulmonary IFNγ mRNA, indicating that cells other than CD4+ lymphocytes contribute to the overall level of this mRNA, such as NK cells. The reduction in IFNγ-positive cells was transient, and on day 38 there were no significant differences in the number of IFNγ- or IL-4-expressing cells between mice which had originally been primed with rRSV/mIL-2 or wt rRSV. At this time point, the percentage of total pulmonary CD4+ cells expressing IFNγ or IL-4 were ~19% and ~0.5, respectively.

In summary, coexpression of mIL-2 by recombinant RSV in the BALB/c mouse model (i) resulted in a modest attenuation of virus growth, (ii) increased the expression of Th1 and Th2 cytokines as detected by analysis of total pulmonary mRNA, and (iii) increased the response of total pulmonary CD4+ T lymphocytes expressing IFNγ or IL-4. The elevated immune response to rRSV/mIL-2 likely accounts for the modest attenuation compared to wt rRSV. Attenuation of virus growth might be a consequence of the observed increase in the CD4+ T lymphocyte response or the observed increase in IFNγ production, or might involve other factors that were not monitored here such as activation and proliferation of CD8+ or NK cells, or stimulation of the secretion of other antiviral cytokines such as type I IFNs or TNF alpha (Karupiah et al., *J. Exp. Med.* 172:1495-1503, 1990; Karupiah et al., *J. Immunol.* 144:290-298, 1990; Karupiah et al., *J. Immunol.* 147:4327-4332, 1991, each incorporated herein by reference). The augmentation in the accumulation of Th1 and Th2 cytokine mRNAs and CD4+ T lymphocytes was observed only during the initial infection by rRSV/mIL-2, and was not observed during the subsequent challenge with wt RSV. Indeed, there was a modest reduction in IFNγ-positive CD4+ T lymphocytes and IL-12 p40 mRNA 4 days after challenge, effects that likely are related. However, the diminution in IFNγ-positive CD4+ T lymphocytes was transient and was not observed on day 10 following challenge.

The elevated immune response during the initial infection by rRSV/mIL-2, evidenced by increased cytokine mRNAs and CD4+ T lymphocytes, was not reflected in increased RSV-specific serum antibodies or increased protective efficacy. However, the titer of RSV-specific antibodies and level of protective immunity induced by RSV infection in mice are so high that it is unclear whether they would be sensitive to further stimulation. For example, when mice that were previously infected with RSV are challenged, little or no challenge virus replication is observed, and hence a further increase in protective immunity might not be observed. To resolve this effect more specifically, the replication and immunogenicity of rRSV/mIL-2 will be further evaluated in non-human primates, where the immune response to RSV is less robust. The available rRSV/mIL-2 virus can be readily employed for this purpose, since there appears to be considerable cross-species IL-2 activity between humans and mice (Flexner et al., *Nature* 330:259-262, 1987; Hugin et al., *Cell*

*Immunol.* 152:499-509, 1993, each incorporated herein by reference). Alternatively, a recombinant RSV expressing human IL-2 can be readily constructed in accordance with the teachings herein.

EXAMPLE III

Construction and Characterization of Recombinant RSV Encoding Murine Granulocyte-Macrophage Colony Stimulating Factor (mGM-CSF)

In the present example, the effect of coexpression of murine GM-CSF (mGM-CSF) by RSV on the immune response to RSV in mice was determined. Following the general strategy described above for the rRSV/mIFNγ and rRSV/mIL-2 viruses, an antigenomic cDNA was constructed which contained the mGM-CSF gene under the control of RSV gene-start and gene-end signals inserted in the G-F intergenic region. This antigenomic cDNA was used to recover the rRSV/mGM-CSF virus. This recombinant virus was moderately attenuated for growth in cell culture and replicated with an efficiency which was essentially indistinguishable from that of the rRSV/CAT, rRSV/IL-2 and rRSV/ mIFNγ viruses. When cultured cells were infected with the rRSV/mGM-CSF virus, high levels of mGM-CSF were secreted into the culture medium. When inoculated into BALB/c mice, the rRSV/GM-CSF virus was marginally attenuated, showing a growth phenotype which was intermediate between the rRSV/IL-2 virus (which was attenuated approximately 5-fold as described above) and the rRSV/CAT and wild type RSV viruses, which were not attenuated in vivo. Mice which were immunized with the rRSV/GM-CSF virus were highly resistant to subsequent challenge with wild type RSV. Interestingly, when the serum antibody response was analyzed with an F-specific ELISA assay as described above, the RSV/mGM-CSF virus induced titers of serum IgG1 and total serum IgG which were more than 10-fold and 6-fold higher, respectively, than that induced by wild type RSV. Thus, coexpression of mGM-CSF by RSV was associated with enhanced immunogenicity.

GM-CSF is produced by wide variety of cells, including T and B lymphocytes, macrophages, epithelial and endothelial cells and fibroblasts, often in response to stimulation by antigen in the case of T and B lymphocytes or inflammatory agents in the case of macrophages, epithelial cells and fibroblasts (for a review, see Quesniaux and Jones, pp. 35-670, in *The Cytokines*, A. W. Thomas (ed.), Academic Press, 1998, incorporated herein by reference). GM-CSF plays important roles in hematopoietic cell proliferation and differentiation, host defense, and immune responses. For example, it stimulates the differentiation and proliferation of granulocyte-macrophage precursors, induces neutrophil migration and antimicrobial activities, and induces the production of dendritic cells. It also has been shown to increase both primary and secondary immune responses when used as an adjuvant, although its application has been primarily in the area of anti-tumor immunity (Tarr et al., pp. 219-232, in *Manual of GM-CSF*, M. Marty (ed.), Blackwell Science, 1996, incorporated herein by reference). However, these prior examples provide little information on the possible effect on host immune responses of coexpression of GM-CSF by an RSV vaccine virus replicating in the respiratory tract.

The mature form of mGM-CSF is a glycoprotein of 124 amino acids. It can be synthesized as a precursor with a cleaved N-terminal signal sequence of 17 amino acids. A cDNA of the GM-CSF ORF was available cloned in pUC 18, and was modified at both ends using unique restriction sites in the plasmid and insert to replace short restriction fragments with DNA duplexes made from synthetic oligonucleotides. In the GM-CSF plasmid, the ORF is preceded by a HindIII site and contains an mluI site shortly downstream of the ATG start codon. This HindIII-mluI restriction fragment was excised and replaced with a synthetic HindIII-mluI fragment that restored the GM-CSF coding sequence and placed it under the control of an RSV gene-start signal that in turn was preceded by an XmaI site. At the downstream end of the GM-CSF ORF, a BsrI site preceded the termination codon, and this codon was followed by a BamHI site. This BsrI-BamHI fragment was excised and replaced with a synthetic BsrI-BamHI fragment that restored the coding sequence and added a downstream RSV gene-end signal and an XmaI site (FIG. 11). This transcription cassette was inserted into the G-F intergenic region of a complete RSV antigenomic cDNA that was modified by the insertion of an XmaI site. This increased the length of the recombinant RSV genome by 465 nucleotides, from 15,223 to 15,688, and the number of encoded mRNAs from 10 to 11.

Recombinant RSV expressing mGMCSF (rRSV/mGMCSF) virus was recovered, grown and analyzed using the experimental strategy and methods described above for the rRSV/mIFNγ and rRSV/mIL-2 viruses. The presence of the GM-CSF transcription cassette in the genome of the recovered rRSV/mGMCSF virus, and the stability of the insert during serial passage in vitro, was confirmed by RT-PCR analysis of intracellular RNA from infected cells. The expression of mGM-CSF as a separate, abundant mRNA was confirmed by Northern blot analysis. In addition, HEp-2 cells infected with rRSV/mGMCSF expressed secreted mGM-CSF in an amount approaching 1 μg per ml of medium supernatant.

The recovered chimeric rRSV/mGMCSF virus formed plaques that were slightly smaller (10%-15% reduction in size) than those of wt rRSV. The in vitro growth of the rRSV/mGMCSF, rRSV/CAT and wt rRSV viruses was examined by infecting HEp-2 cells at an MOI of 2 PFU and measuring the kinetics of production and release of infectious virus (FIG. 12). This showed that the growth of the rRSV/mGMCSF and rRSV/CAT viruses was essentially indistinguishable and was somewhat delayed and reduced compared to wt recombinant RSV (maximum difference of 52-fold at 40 hours post-infection between rRSV/CAT and wt rRSV). These results are consistent with the general observation that insertion of an additional gene into the RSV genome attenuates its growth in vitro, as described in greater detail in the preceding examples.

The effect might be due to the increase in genome length, or increased number of transcription cassettes, or both, but does not appear to be specific to the GM-CSF protein. Furthermore, human and murine GM-CSF are not cross-reactive in biological activity or receptor binding (Quesniaux and Jones, pp. 35-670, in *The Cytokines*, A. W. Thomas (ed.), Academic Press, 1998), and hence this murine cytokine should not be active in HEp-2 cells, a human cell line.

To evaluate the replication of rRSV/mGMCSF in vivo, BALB/c mice were infected intranasally with $10^6$ PFU per animal of rRSV/mGMCSF, rRSV/CAT or wt rRSV. Note that the rRSV/mIFNγ and rRSV/mIL-2 viruses were analyzed in parallel in this same experiment, and the results for those viruses were described above. Animals from each group were sacrificed on days 3, 4 and 5 post infection, and the concentration of virus in the upper (nasal turbinates) and the lower (lungs) respiratory tract was determined by plaque assay (Table 4). As described above, the replication of rRSV/CAT was not significantly different than that of wt rRSV at either location for all of the time points except for in the lungs in day 3, where it was $0.4 \log_{10}$ lower, a difference that was small but statistically significant (p<0.01). The titer of rRSV/mGMCSF was consistently lower than the other two viruses at both locations at all time points, but only on day 5 in the lungs was the difference statistically significant compared to both wt rRSV and rRSV/CAT (approximately 5-fold reduced compared to wt rRSV and rRSV/CAT, p<0.01 and 0.001, respectively).

TABLE 4

Replication of wild type rRSV, rRSV/CAT, and rRSV/mGMCSF in the upper (nasal turbinates) and lower (lungs) respiratory tract of BALB/c mice[a]

| | Mean titer in mice[b] ($\log_{10}$ pfu/g tissue) | | | | | |
|---|---|---|---|---|---|---|
| | Day 3 | | Day 4 | | Day 5 | |
| Virus | Nasal turb. | Lungs | Nasal turb. | Lungs | Nasal turb. | Lungs |
| rRSV/mGMCSF | 3.50 ± 0.15[c] | 3.40 ± 0.21[e] | 3.34 ± 0.10[d,e] | 4.16 ± 0.08[e] | 3.46 ± 0.07[d] | 3.98 ± 0.10[d,f] |
| rRSV/CAT | 3.96 ± 0.07[c] | 3.66 ± 0.07[d] | 3.98 ± 0.11[d] | 4.36 ± 0.06 | 3.98 ± 0.02[d] | 4.68 ± 0.06[f] |
| wt rRSV | 3.78 ± 0.08 | 4.06 ± 0.07[d,e] | 3.74 ± 0.08[e] | 4.50 ± 0.08[e] | 3.76 ± 0.14 | 4.50 ± 0.04[d] |

[a]Mice were administered $10^6$ PFU per animal of the indicated virus intranasally under light anesthesia on day 0 and sacrificed on days 3, 4 and 5.
[b]Virus titer was determined in the nasal turbinate and lung tissues and is shown as mean titer ± standard error ($\log_{10}$ pfu/g tissue), n = 5.
[c-f]Statistical significance by Student's t test between values in the same column: [c]p < 0.05; [d]<0.01; [e]p < 0.02; [f]p < 0.001. Other p values exceeded 0.05.

To evaluate the immunogenicity of rRSV/mGMCSF, mice were infected with rRSV/mGMCSF, rRSV/CAT or wt rRSV as described above, and serum samples were taken on days 0 (immediately before infection), 28 and 56 (Table 5). Each of the viruses induced a high titer of RSV-neutralizing serum antibodies. The titer associated with the rRSV/mGMCSF virus was 1.5- to 2-fold greater than that observed for the wt rRSV or rRSV/CAT virus. In addition, the titers of RSV-specific serum IgA, IgG1, IgG2a, and total IgG, were determined by ELISA with purified RSV F protein as antigen (Table 5). There were no significant differences in antibody titer between the wt rRSV and rRSV/CAT viruses. In contrast, the rRSV/mGMCSF virus induced a 9.2-fold and 4.9-fold higher titer of IgG1 and total IgG antibodies, respectively, compared to wt rRSV. For comparison, in a previous example, the rRSV/IFNγ virus induced titers of IgG1 and total IgG that were 7-fold and 4-fold higher, respectively, than those of wt rRSV. Thus, RSV immunogenicity in mice was increased by coexpression of mIFNγ or mGM-CSF.

TABLE 5

RSV serum antibody titers
(reciprocal mean log$_2$ ± standard error) on days 0 (prior to immunization), 28 and 56[a]

| | Serum ELISA antibodies to RSV F protein | | | | | | | | | | | | RSV serum neutralizing antibodies | | |
|---|---|---|---|---|---|---|---|---|---|---|---|---|---|---|---|
| | IgA | | | IgG1 | | | IgG2A | | | Total IgG | | | | | |
| Virus | 0 | 28 | 56 | 0 | 28 | 56 | 0 | 28 | 56 | 0 | 28 | 56 | 0 | 28 | 56 |
| rRSV/mGMCSF | 7.6 ± 0.2 | 12.6 ± 0.5 | 11.6 ± 0.6. | <5.3 | 11.3 ± 0.5 | 13.3 ± 0.5 | <5.3 | 9.8 ± 0.5 | 10.1 ± 0.4 | <5.3 | 11.1 ± 0.5 | 12.1 ± 0.4 | <3.3 | 9.9 ± 0.9 | 12.2 ± 0.6 |
| rRSV/CAT | 7.6 ± 0.2 | 12.1 ± 0.7 | 9.6 ± 0.9 | <5.3 | 11.3 ± 0.5 | 8.8 ± 0.6 | <5.3 | 9.1 ± 0.3 | 9.8 ± 0.5 | <5.3 | 10.8 ± 0.2 | 9.6 ± 0.5 | <3.3 | 9.9 ± 1.2 | 11.7 ± 0.7 |
| wt RSV | 7.3 ± 0 | 12.3 ± 0.9 | 11.3 ± 0.5 | <5.3 | 11.3 ± 0.8 | 10.1 ± | <5.3 | 9.6 ± 0.3 | 10.3 ± 0.4 | <5.3 | 11.6 ± 0.3 | 9.8 ± 0.3 | <3.3 | 9.8 ± 0.3 | 11.2 ± 0.5 |
| Mock | 7.3 ± 0 | 7.8 ± 0.3 | <5.3 | <5.3 | <5.3 | <5.3 | <5.3 | <5.3 | <5.3 | <5.3 | 6.6 ± 0.4 | <5.3 | <3.3 | <3.3 | <3.3 |

[a]Eight mice per group were used. Antibody titers on day 56 were determined in a separate assay. Note that the ELISA data for the IG subclasses cannot be compared exactly with those of animals that had received the rRSV/IFNγ or RSV/mIL-2 viruses in previous examples because different ELISA cut-offs were used. However, qualitative comparison can be made.

The mice in each group were then challenged on day 56 by the intranasal inoculation of 10$^6$ PFU of wt RSV per animal. Four days later, on day 60, the mice were sacrificed and virus titers in the upper and lower respiratory tract were determined (not shown). All of the previously-infected animals exhibited a high level of resistance to challenge virus replication. Replication of the challenge virus was undetectable in animals which had been previously infected with rRSV/CAT or rRSV/mGMCSF (mean titers of <2.0 log$_{10}$ PFU/g in the nasal turbinates and <1.7 log$_{10}$ PFU/g in the lungs), whereas a low level of RSV was detected in animals which had been immunized with wt rRSV (mean titers of 2.3 log$_{10}$ PFU/g in the nasal turbinates and <1.7 log$_{10}$ PFU/g in the lungs). In contrast, animals which had not been previously infected had mean titers of 4.7 log$_{10}$ PFU/g in the nasal turbinates and lungs. Thus, the three viruses were indistinguishable with regard to the ability to induce a high level of resistance to reinfection.

The total pulmonary CD4+ T lymphocyte response to rRSV/mGMCSF versus wt rRSV was measured. Mice were infected with 10$^6$ PFU of rRSV/mGMCSF or wt rRSV, or were mock-infected. 4 animals from each group were sacrificed each on days 4 and 10, and lungs were harvested and processed to isolate total pulmonary mononuclear cells. The remaining mice in each group were challenged intranasally on day 28 with 10$^6$ PFU of wt RSV, and 4 mice from each group were sacrificed 4 and 10 days later (days 32 and 38) and their lungs were harvested and mononuclear cells were isolated. Using methods described above for the rRSV/mIL-2 virus, total pulmonary mononuclear cells were analyzed by flow cytometry with immunostaining for the CD4+ marker, for the intracellular expression of the Th2 marker cytokine IL-4, or the Th1 marker cytokine IFN-γ. Cells from each individual animal were processed separately.

On day 4 following the initial infection, animals that received rRSV/mGMCSF or wt rRSV exhibited increased percentages of CD4+ lymphocytes that were IFNγ-positive, IL-4-positive, or double-positive (Table 6), but the magnitude of the response was very similar for the two viruses and was not very high (3.43-3.79% IFNγ-positive, compared to 1.04% for the uninfected control). In contrast, on day 10, animals that had received rRSV/mGMCSF exhibited a very high level of CD4+ lymphocytes that were IFNγ-positive (21.4% compared to 6.7% for wt rRSV-infected animals and 2.4% for the uninfected control). The percentage of CD4+ cells that were positive for IL-4 was much smaller and exhibited a relatively small increase on either day (values for day 10 were: 1.72% for rRSV/mGMCSF, 1.08% for RSV-infected animals, and 1.15% for the uninfected control). When the mice were challenged, animals that had received either wt rRSV or rRSV/mGMCSF had a strong secondary response, with approximately 20.5% of cells positive for IFNγ on day 38. In contrast, the percentage of CD4+ lymphocytes expressing IL-4 was approximately the same as for animals that were not infected with RSV. Thus, the expression of mGM-CSF from the RSV genome during infection resulted in a strong stimulation of Th1 CD4+ lymphocytes, with the percentage of IFNγ-positive cells being more than three-fold that achieved during a primary RSV infection and being comparable to that achieved during the secondary response associated with a secondary RSV infection.

TABLE 6

Flow cytometric analysis of total pulmonary CD4+ cells
isolated from mice infected with wild type RSV or rRSV/GMCSF[a]

| | wt rRSV | | | rRSV/mGMCSF | | | Mock | | |
|---|---|---|---|---|---|---|---|---|---|
| Day | IFNγ+ | IL-4+ | Dbl+ | IFNγ+ | IL-4+ | Dbl+ | IFNγ+ | IL-4+ | Dbl+ |
| 4 | 3.43 ± 0.51 | 1.28 ± 0.33 | 0.40 ± 0.11 | 3.79 ± 0.63 | 1.91 ± 0.16 | 0.30 ± 0.09 | 1.04 ± 0.04 | 0.45 ± 0.03 | 0.11 ± 0.01 |
| 10 | 6.69 ± 1.27 | 1.08 ± 0.37 | 0.23 ± 0.06 | 21.43 ± 1.49 | 1.72 ± 0.26 | 0.95 ± 0.11 | 2.42 ± 0.25 | 1.15 ± 0.13 | 0.47 ± 0.10 |

TABLE 6-continued

Flow cytometric analysis of total pulmonary CD4+ cells
isolated from mice infected with wild type RSV or rRSV/GMCSF[a]

|  | wt rRSV | | | rRSV/mGMCSF | | | Mock | | |
| --- | --- | --- | --- | --- | --- | --- | --- | --- | --- |
| Day | IFNγ+ | IL-4+ | Dbl+ | IFNγ+ | IL-4+ | Dbl+ | IFNγ+ | IL-4+ | Dbl+ |
| 32 | 6.87 ± 0.11 | 1.15 ± 0.13 | 0.17 ± 0.03 | 6.88 ± 0.56 | 1.06 ± 0.13 | 0.19 ± 0.01 | 2.48 | 0.79 | 0.06 |
| 38 | 20.50 ± 1.56 | 0.46 ± 0.05 | 0.16 ± 0.01 | 20.21 ± 1.69 | 0.60 ± 0.05 | 0.32 ± 0.04 | 8.07 ± 0.16 | 0.78 ± 0.12 | 0.15 ± 0.03 |

[a]Mice were infected intranasally on day 0 with $10^6$ PFU per animal of the indicated virus, or were mock-infected. Animals from each group were harvested on days 4 and 10 (in most cases, 4 animals were sacrificed per group per day). The remaining animals were challenged on day 28 with $10^6$ PFU of wt RSV per animal, and 4 animals per group were sacrificed on days 32 and 38. Total pulmonary mononuclear cells were analyzed by flow cytometry using immunostaining for CD4, IFNγ and IL-4. Values are expressed as the percentage of CD4+ lymphocytes, with the standard error indicated. Dbl+ indicates positive for both IFNγ and IL-4.

It is widely thought that a Th1-biased T lymphocyte response is a marker of a protective immune response to RSV versus an immunopathologic response (Connors et al., *J. Virol.* 68:5321-5325, 1994; Waris et al., *J. Virol.* 70:2852-2860, 1996; Hussell et al., *Eur. J. Immunol.* 27:3341-3349, 1997; Fischer, J. E, *J. Virol.* 71:8672-8677; incorporated herein by reference). The increased level of CD4+ lymphocytes secreting IFN indicated that the rRSV/mGMCSF virus stimulated an immune response that was strongly biased towards the Th1 subset. Indeed, RSV infection itself stimulates a Th1-biased response, which probably is due to IFN produced by natural killer and CD8+ T lymphocytes (Hussell et al., *Eur. J. Immunol.* 27:3341-3349, 1997; Srikiatkhachorn et al., *J. Exp. Med.* 186:421-432, 1997; Spender et al., *J. Gen. Virol.* 79:1751-1758, 1998; incorporated herein by reference). Thus, the immune response to the rRSV/mGMCSF virus resembled that of natural infection but was greatly enhanced. Analysis of total pulmonary mRNA by an RNAse protection assay showed that infection with wt rRSV or rRSV/mGMCSF resulted in increases in mRNA for IFN and the p40 subunit of IL-12, consistent with a Th1-biased response, and that the response was greater for the rRSV/mGMCSF virus.

In summary, coexpression of mGM-CSF by recombinant RSV in the BALB/c mouse model (i) resulted in a modest attenuation of virus growth, (ii) increased the expression of RSV-specific serum IgG1 and total IgG, and (iii) increased the response of total pulmonary CD4+ T lymphocytes expressing IFNγ during the initial infection. This increase appeared to depend on the ongoing expression of mGM-CSF, because it was not recapitulated during the subsequent challenge with wt rRSV. Attenuation of virus growth might be a consequence of the observed increase in the CD4+ T lymphocyte response, the increase in IFNγ production, the increase in RSV-specific antibodies, or might involve other factors that were not monitored here such as activation and proliferation of CD8+ or NK cells, or stimulation of the secretion of other antiviral cytokines such as type I IFNs or TNF alpha. Thus, coexpression of GM-CSF during RSV infection increased the magnitude of the immune response and maintained a strong bias towards the Th1 subset of CD4+ lymphocytes. These are characteristics that are highly favorable for an RSV vaccine and could not have been predicted.

EXAMPLE IV

Construction of Recombinant RSV Encoding Murine IL-4

Human IL-4 is 153 amino acids in length and is processed into a 129-amino acid secreted form. IL-4 is produced by activated T lymphocytes, mast cells and basophils and acts on a wide variety of cells (Chopart et al., The Cytokine Handbook, A. W. Thomson (ed.), p 133-174, Academic Press, 1998, incorporated herein by reference). An important effect of IL-4 is to induce differentiation of T helper cell precursors into the Th2 subclass, whereas IFNγ and IL-12 have the effect of promoting differentiation into the Th1 subclass. The Th1 and Th2 subclasses have been characterized in mice and, to a lesser extent, humans, and as a generalization are associated with cell-mediated cytotoxic and inflammatory responses (Th1) versus responses biased towards the production of antibody, especially IgE, and eosinophil proliferation and function (Th2) (Mosmann and Sad, *Immunol. Today* 17:138-146, 1996, incorporated herein by reference).

Following the general strategy described above for the rRSV/mIFNγ, rRSV/mIL-2, and rRSV/mGM-CSF viruses, an antigenomic cDNA was constructed which contained the mIL-4 gene under the control of RSV gene-start and gene-end signals inserted in the G-F intergenic region. This antigenomic cDNA was used to recover the rRSV/mIL-4 virus. This recombinant virus was moderately attenuated for growth in cell culture and replicated with an efficiency which was essentially indistinguishable from that of the other rRSV viruses containing the CAT, mIFNγ, mIL-2, mGM-CSF inserts. When cultured cells were infected with the rRSV/mIL-4 virus, high levels of IL-4 were secreted into the culture medium. When inoculated into BALB/c mice, the rRSV/mIL4 virus replicated with an efficiency which was essentially indistinguishable from that of the rRSV/CAT and wild type RSV viruses, which were not attenuated in vivo. Thus, the coexpression of mIL-4 did not attenuate the replication of RSV. Mice which were immunized with the rRSV/mIL-4 virus were highly resistant to subsequent challenge with wild type RSV.

These foregoing examples illustrate the expression of individual murine cytokines by rRSV, and their evaluation in BALB/c mice. The results demonstrate that expression of one exemplary cytokine, namely mIFNγ, is highly attenuating for RSV. Expression of mIL-2 was moderately attenuating, mGM-CSF was slightly attenuating, and mIL-4 was not attenuating. Despite the high level of attenuation of the rRSV/mIFNγ virus, its level of immunogenicity was not reduced. This likely reflects the biological activity of its expressed cytokine, mIFNγ. Evidence for enhanced immunogenicity was also observed for the rRSV/mGM-CSF virus. Thus, two benefits were observed for the coexpression of immune modulators by rRSV: namely, attenuation and increased immunogenicity. Both of these are highly desirable phenotypic characteristics for an RSV vaccine.

Based on these demonstrated effects in the murine model, additional recombinant RSVs containing the corresponding human cytokine genes can be readily implemented and evaluated for vaccine use in a primate model. Since mice are only semi-permissive for RSV infection, it is expected that the effects observed in the mouse model will actually be enhanced in primates, where higher levels of RSV replication and gene expression will yield higher levels of RSV antigen and cytokine. In addition to these aspects of the invention, a variety of other immune modulatory molecules will be introduced into recombinant RSV in accordance with the teachings herein. Among numerous attractive candidates is IL-18, which is a Th1-type cytokine which plays an important role in stimulating the production of IFNγ and stimulating NK cells and cytotoxic T cells (Dinarello, *J. Allergy Clin. Immunol.* 103:11-24, 1999, incorporated herein by reference).

Microorganism Deposit Information

The following materials have been deposited with the American Type Culture Collection, 10801 University Boulevard, Manassas, Va. 20110-2209, under the conditions of the Budapest Treaty and designated as follows:

Although the foregoing invention has been described in detail by way of example for purposes of clarity of understanding, it will be apparent to the artisan that certain changes and modifications may be practice within the scope of the appended claims which are presented by way of illustration not limitation.

| Plasmid | Accession No. | Deposit Date |
|---|---|---|
| cpts RSV 248 | ATCC VR 2450 | Mar. 22, 1994 |
| cpts RSV 248/404 | ATCC VR 2454 | Mar. 22, 1994 |
| cpts RSV 248/955 | ATCC VR 2453 | Mar. 22, 1994 |
| cpts RSV 530 | ATCC VR 2452 | Mar. 22, 1994 |
| cpts RSV 520/1009 | ATCC VR 2451 | Mar. 22, 1994 |
| cpts RSV 530/1030 | ATCC VR 2455 | Mar. 22, 1994 |
| RSV B-1cp 52/2B5 | ATCC VR 2542 | Sep. 26, 1996 |
| RSV B-1 cp-23 | ATCC VR 2579 | Jul. 15, 1997 |
| p3/7(131) | ATCC 97990 | Apr. 18, 1997 |
| p3/7(131)2G | ATCC 97989 | Apr. 18, 1997 |
| p218(131) | ATCC 97991 | Apr. 18, 1997 |

What is claimed is:

1. An isolated polynucleotide molecule comprising a recombinant respiratory syncytial virus (RSV) genome or antigenome comprising polynucleotide sequences encoding a major nucleocapsid (N) protein, a nucleocapsid phosphoprotein (P), a large polymerase protein (L), and a M2(ORF1) polymerase elongation factor, and wherein said recombinant RSV genome or antigenome is modified to incorporate a heterologous polynucleotide sequence encoding an immune modulatory molecule selected from the group consisting of interleukin 2 (IL-2), interleukin 4 (IL-4), interferon gamma (IFNλ) and granulocyte-macrophage colony stimulating factor (GM-CSF), BlyS ligand, Flt3 and CD40.

2. The isolated polynucleotide molecule of claim 1, wherein the cytokine is interferon gamma (IFNλ).

3. The isolated polynucleotide molecule of claim 1, wherein the cytokine is granulocyte-macrophage colony stimulating factor (GM-CSF).

4. The isolated polynucleotide molecule of claim 1, wherein the cytokine is interleukin 2 (IL-2).

5. The isolated polynucleotide molecule of claim 1, wherein the cytokine is interleukin 4 (IL-4).

6. The isolated polynucleotide molecule of claim 1, wherein growth of a recombinant RSV encoded by said recombinant genome or antigenome in cell culture is attenuated by approximately 10-15 fold or greater compared to growth of a corresponding wild-type or mutant parental RSV strain.

7. The isolated polynucleotide molecule of claim 1, wherein a recombinant RSV encoded by said recombinant genome or antigenome expresses the immune modulatory molecule in cell culture medium at a level of between about 10-20 micrograms per $10^6$ cells or greater.

8. The isolated polynucleotide molecule of claim 1, wherein a recombinant RSV encoded by said recombinant genome or antigenome is attenuated for growth in cell culture and for replication in both the upper and lower respiratory tracts of a mammalian host, and wherein the virus induces an immune response to RSV in an immunized host.

9. The isolated polynucleotide molecule of claim 1, wherein a recombinant RSV encoded by said recombinant genome or antigenome is attenuated by the activity of the immune modulatory molecule expressed in infected cells.

10. The isolated polynucleotide molecule of claim 1, wherein a recombinant RSV encoded by said recombinant genome or antigenome induces titers of serum IgG that are 2 to 10-fold higher or more than levels of serum IgG induced by wild type RSV.

11. The isolated polynucleotide molecule of claim 1, wherein the recombinant genome or antigenome incorporates one or more attenuating mutations from a human RSV.

12. The isolated polynucleotide molecule of claim 11, wherein the recombinant genome or antigenome incorporates at least one and up to a full complement of attenuating mutations present within a panel of mutant human RSV strains, said panel comprising cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579).

13. The isolated polynucleotide molecule of claim 11, wherein the recombinant genome or antigenome incorporates at least one and up to a full complement of attenuating mutations specifying an amino acid substitution at Val267 in the RSV N gene, Glu218 and/or Thr523 in the RSV F gene, Asn43, Cys319, Phe 521, Gln831, Met1169, Tyr1321 and/or His 1690 in the RSV polymerase gene L, and a nucleotide substitution in the gene-start sequence of gene M2.

14. The isolated polynucleotide molecule of claim 11, wherein the recombinant genome or antigenome incorporates at least two attenuating mutations.

15. The isolated polynucleotide molecule of claim 11, wherein the recombinant genome or antigenome includes at least one attenuating mutation stabilized by multiple nucleotide changes in a codon specifying the mutation.

16. The isolated polynucleotide molecule of claim 1, wherein the recombinant genome or antigenome incorporates a nucleotide modification specifying a phenotypic change selected from the group consisting of a change in growth in cell culture, attenuation, temperature-sensitivity, cold-adaptation, plaque size, host-range restriction, antigen expression and a change in immunogenicity.

17. The isolated polynucleotide molecule of claim 16, wherein the nucleotide modification specifying the phenotypic change alters a SH, NS1, NS2, M2 ORF2, or G gene of the recombinant RSV.

18. The isolated polynucleotide molecule of claim 17, wherein a SH, NS1, NS2, M2 ORF2, or G gene is deleted from said recombinant genome or antigenome in whole or in part or expression of the gene is reduced or ablated by a frame shift or introduction of one or more stop codons in an open reading frame of the gene or a modification of a translational start site.

19. The isolated polynucleotide molecule of claim 16, wherein the nucleotide modification specifying the phenotypic change comprises a nucleotide deletion, insertion, substitution, addition or rearrangement of a cis-acting regulatory sequence of a selected gene within the recombinant RSV genome or antigenome.

20. The isolated polynucleotide molecule of claim 16, wherein a gene end (GE) signal of the NS1 or NS2 gene is modified.

21. The isolated polynucleotide molecule of claim 16, wherein the nucleotide modification specifying the phenotypic change comprises an insertion, deletion, substitution, or rearrangement of a translational start site within the recombinant RSV genome or antigenome.

22. The isolated polynucleotide molecule of claim 21, wherein the translational start site for a secreted form of the RSV G glycoprotein is ablated.

23. The isolated polynucleotide molecule of claim 16, wherein the recombinant genome or antigenome is modified to encode a non-RSV molecule selected from the group consisting of one or more T-helper epitope(s), a restriction site marker, or a protein of a microbial pathogen capable of eliciting a protective immune response in a mammalian host.

24. The isolated polynucleotide molecule of claim 16, wherein the recombinant genome or antigenome incorporates a gene or genome segment from parainfluenza virus (PIV).

25. The isolated polynucleotide molecule of claim 24, wherein the gene or genome segment encodes a PIV HN or F glycoprotein or immunogenic domain or epitope thereof.

26. The isolated polynucleotide molecule of claim 24, wherein the genome segment encodes an ectodomain or immunogenic epitope of HN or F of PIV1, PIV2, or PIV3.

27. The isolated polynucleotide molecule of claim 1, wherein the recombinant genome or antigenome comprises a partial or complete RSV background genome or antigenome of a human or bovine RSV combined with a heterologous gene or genome segment of a different RSV to form a human-bovine chimeric RSV genome or antigenome.

28. The isolated polynucleotide molecule of claim 27, wherein the heterologous gene or genome segment encodes a RSV F, G or SH glycoprotein or an immunogenic domain or epitope thereof.

29. The isolated polynucleotide molecule of claim 27, wherein the heterologous gene or genome segment is substituted for a counterpart gene or genome segment in a partial RSV background genome or antigenome.

30. The isolated polynucleotide molecule of claim 27, wherein the heterologous gene or genome segment is added adjacent to or within a noncoding region of the partial or complete RSV background genome or antigenome.

31. The isolated polynucleotide molecule of claim 27, wherein the chimeric genome or antigenome comprises a partial or complete human RSV background genome or antigenome combined with a heterologous gene or genome segment from a bovine RSV.

32. The isolated polynucleotide molecule of claim 27, wherein the chimeric genome or antigenome comprises a partial or complete bovine RSV background genome or antigenome combined with a heterologous gene or genome segment from a human RSV.

33. The isolated polynucleotide molecule of claim 32, wherein one or more human RSV glycoprotein genes F, G and SH or a genome segment encoding a cytoplasmic domain, transmembrane domain, ectodomain or immunogenic epitope thereof is substituted for a counterpart gene or genome segment within the bovine RSV background genome or antigenome.

34. The isolated polynucleotide molecule of claim 33, wherein one or both human RSV glycoprotein genes F and G is substituted to replace one or both counterpart F and G glycoprotein genes in the bovine RSV background genome or antigenome.

35. The isolated polynucleotide molecule of claim 34, wherein both human RSV glycoprotein genes F and G are substituted to replace counterpart F and G glycoprotein genes in the bovine RSV background genome or antigenome.

36. The isolated polynucleotide molecule of claim 35, wherein the heterologous gene or genome segment is from a subgroup A or subgroup B human RSV.

37. The isolated polynucleotide molecule of claim 35, wherein the human-bovine chimeric genome or antigenome incorporates antigenic determinants from both subgroup A and subgroup B human RSV.

38. The isolated polynucleotide molecule of claim 1, wherein the recombinant genome or antigenome encodes a RSV that is a complete virus.

39. The isolated polynucleotide molecule of claim 1, wherein the recombinant genome or antigenome encodes a RSV that is a subviral particle.

40. The isolated polynucleotide molecule of claim 1, wherein the recombinant genome or antigenome comprises a partial or complete RSV vector genome or antigenome combined with one or more heterologous genes or genome segments encoding one or more antigenic determinants of one or more heterologous pathogens.

41. The isolated polynucleotide molecule of claim 40, wherein said one or more heterologous pathogens is a heterologous RSV and said heterologous gene(s) or genome segment(s) encode(s) one or more RSV NS1, NS2, N, P, M, SH, M2(ORF1), M2(ORF2), L, F or G protein(s) or fragment(s) thereof.

42. The isolated polynucleotide molecule of claim 40, wherein the vector genome or antigenome is a partial or complete RSV A genome or antigenome and the heterologous gene(s) or genome segment(s) encoding the antigenic determinant(s) is/are of a RSV B subgroup virus.

43. The isolated polynucleotide molecule of claim 40, wherein the chimeric genome or antigenome incorporates one or more gene(s) or genome segment(s) of a BRSV that specifies attenuation.

44. The isolated polynucleotide molecule of claim 40, wherein one or more HPIV1, HPIV2, or HPIV3 gene(s) or genome segment(s) encoding one or more HN and/or F glycoprotein(s) or antigenic domain(s), fragment(s) or epitope(s) thereof is/are added to or incorporated within the partial or complete HRSV vector genome or antigenome.

45. The isolated polynucleotide molecule of claim 40, wherein the vector genome or antigenome is a partial or complete BRSV genome or antigenome and the heterologous gene(s) or genome segment(s) encoding the antigenic determinant(s) is/are of one or more HRSV(s).

46. The isolated polynucleotide molecule of claim 45, wherein the partial or complete BRSV genome or antigenome incorporates one or more gene(s) or genome segment(s) encoding one or more HRSV glycoprotein genes selected from the group consisting of F, G and SH and one or more genome segment(s) encoding cytoplasmic domain, transmembrane domain, ectodomain or immunogenic epitope portion(s) of F, G, and SH of HRSV.

47. The isolated polynucleotide molecule of claim 40, wherein the vector genome or antigenome is a partial or complete HRSV or BRSV genome or antigenome and the heterologous pathogen is selected from the group consisting of measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses.

48. The isolated polynucleotide molecule of claim 47, wherein said one or more heterologous antigenic determinant(s) is/are selected from the group consisting of measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, Flavivirus E and NS1 proteins, and alphavirus B protein, and antigenic domains, fragments and epitopes thereof.

49. The isolated polynucleotide molecule of claim 47, wherein the heterologous pathogen is measles virus and the heterologous antigenic determinant(s) is/are selected from the group consisting of the measles virus HA and F proteins, and antigenic domains, fragments and epitopes thereof.

50. The isolated polynucleotide molecule of claim 49, wherein a transcription unit comprising an open reading frame (ORF) of a measles virus HA gene is added to or incorporated within a HRSV vector genome or antigenome.

51. The isolated polynucleotide molecule of claim 1, wherein the recombinant genome or antigenome has one or more shifted RSV gene(s) or genome segment(s) within said recombinant genome or antigenome that is/are positionally shifted to a more promoter-proximal or promoter-distal position relative to a position of said RSV gene(s) or genome segment(s) within a wild type RSV genome or antigenome.

52. The isolated polynucleotide molecule of claim 51, wherein said one or more shifted gene(s) or genome segment(s) is/are shifted to a more promoter-proximal or promoter-distal position by deletion, insertion or rearrangement of one or more displacement polynucleotide(s) within said partial or complete recombinant RSV genome or antigenome.

53. The isolated polynucleotide molecule of claim 52, wherein said displacement polynucleotide(s) comprise(s) one or more polynucleotide insert(s) of between 150 nucleotides (nts) and 4,000 nucleotides in length which is inserted in a non-coding region (NCR) of the genome or antigenome or as a separate gene unit (GU), said polynucleotide insert lacking a complete open reading frame (ORF) and specifying an attenuated phenotype in said recombinant RSV.

54. The isolated polynucleotide molecule of claim 52, wherein said displacement polynucleotide(s) comprise(s) one or more RSV gene(s) or genome segment(s) selected from the group consisting of RSV NS1, NS2, N, P, M, SH, M2(ORF1), M2(ORF2), L, F and G genes and genome segments thereof and leader, trailer and intergenic regions of the RSV genome and segments thereof.

55. The isolated polynucleotide molecule of claim 52, wherein said displacement polynucleotide(s) comprise(s) one or more bovine RSV (BRSV) or human RSV (HRSV) gene(s) or genome segment(s) selected from RSV NS1, NS2, N, P, M, SH, M2(ORF1), M2(ORF2), L, F and G gene(s) or genome segment(s) and leader, trailer and intergenic regions of the RSV genome or segments thereof.

56. The isolated polynucleotide molecule of claim 55, wherein said displacement polynucleotide(s) is/are deleted to form the recombinant RSV genome or antigenome to cause a positional shift of said one or more shifted RSV gene(s) or genome segment(s) within said recombinant genome or antigenome to a more promoter-proximal position relative to a position of said RSV gene(s) or genome segment(s) within a wild type RSV genome or antigenome.

57. The isolated polynucleotide molecule of claim 56, wherein said displacement polynucleotide(s) that is/are deleted to form the recombinant RSV genome or antigenome comprise one or more RSV NS1, NS2, SH, M2(ORF2), or G gene(s) or genome segment(s) thereof.

58. The isolated polynucleotide molecule of claim 51, wherein the RSV glycoprotein gene G is rearranged within said recombinant RSV genome or antigenome to a gene order position that is more promoter-proximal compared to the wild type gene order position of G.

59. The isolated polynucleotide molecule of claim 51, wherein the RSV glycoprotein gene F is rearranged within said recombinant RSV genome or antigenome to a gene order position that is more promoter-proximal compared to the wild type gene order position of F.

60. The isolated polynucleotide molecule of claim 51, wherein both RSV glycoprotein genes G and F are rearranged within said recombinant RSV genome or antigenome to gene order positions that are more promoter-proximal compared to the wild type gene order positions of G and F.

61. The isolated polynucleotide molecule of claim 60, wherein the RSV glycoprotein gene G is shifted to gene order position 1 and the RSV glycoprotein gene F is shifted to gene order position 2 within said recombinant RSV genome or antigenome.

62. The isolated polynucleotide molecule of claim 51, wherein the RSV SH and NS2 genes are both deleted to form the recombinant RSV genome.

63. The isolated polynucleotide molecule of claim 51, wherein the RSV SH, NS1 and NS2 genes are all deleted to form the recombinant RSV genome.

* * * * *

```
SEQUENCE LISTING

<160> NUMBER OF SEQ ID NOS: 10

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Gene start
      attachment oligonucleotide for MIFNy

<400> SEQUENCE: 1
tatacccggg atggggcaaa tatgaacgct acacactgca t                          41

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Gene end
      attachment oligonucleotide for MIFNy

<400> SEQUENCE: 2
attacccggg aatttttaat aacttcagca gcgactcctt ttcc                       44

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: PCR primer
      for IL-2 with gene start sequence

<400> SEQUENCE: 3
tatacccggg atggggcaaa tatgtacagc atgcagctcg c                          41

<210> SEQ ID NO 4
<211> LENGTH: 44
<212> TYPE: DNA
<213> ORGANISM: Artificial Sequence
<220> FEATURE:
```

```
<223> OTHER INFORMATION: Description of Artificial Sequence: PCR primer
      for IL-2 with gene end sequence

<400> SEQUENCE: 4
attacccggg aattttaat aactttattg agggcttgtt gaga                    44

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Sequence
      flanking IFNy insert with gene start

<400> SEQUENCE: 5
cccgggatgg ggaaataatg                                              20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Sequence
      flanking IFNy insert with gene end

<400> SEQUENCE: 6
tgaagttatt aaaaattccc ggg                                          23

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence:Detail of
      XmaI linked sequences

<400> SEQUENCE: 7
aggccccggg gcct                                                    14

<210> SEQ ID NO 8
<211> LENGTH: 83
<212> TYPE: DNA
<213> ORGANISM: Artificial Sequence
<220> FEATURE:
<223> OTHER INFORMATION: Description of Artificial Sequence: Sequence
      flanking GMLSF insert with gene start

<400> SEQUENCE: 8
agttacttaa aaacatatta tcacaaaagg ccccggggcc ttgaccaaac ttaaacagaa   60
tcaaaataaa ctctggggca aat                                          83

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Sequence
      flanking GMLSF insert with gene end

<400> SEQUENCE: 9
cccgggatgg ggcaaatatg                                              20

<210> SEQ ID NO 10
<211> LENGTH: 23
<212> TYPE: DNA
<213> ORGANISM: Artificial Sequence
```

```
<220> FEATURE:
<223> OTHER INFORMATION: Description of Artificial Sequence: Detail of
      XmaI linked sequences

<400> SEQUENCE: 10
taaagttatt aaaaattccc ggg                                            23
```